US007855201B2

(12) United States Patent
Thompson et al.

(10) Patent No.: US 7,855,201 B2
(45) Date of Patent: Dec. 21, 2010

(54) MORPHOLINE CARBOXAMIDE PROKINETICIN RECEPTOR ANTAGONISTS

(75) Inventors: Wayne J. Thompson, Lansdale, PA (US); Jeffrey Y. Melamed, North Wales, PA (US)

(73) Assignee: Merck Sharp & Dohme. Corp., Rahway, NJ (US)

( * ) Notice: Subject to any disclaimer, the term of this patent is extended or adjusted under 35 U.S.C. 154(b) by 365 days.

(21) Appl. No.: 12/085,978

(22) PCT Filed: Dec. 4, 2006

(86) PCT No.: PCT/US2006/046330

§ 371 (c)(1),
(2), (4) Date: Jun. 3, 2008

(87) PCT Pub. No.: WO2007/067511

PCT Pub. Date: Jun. 14, 2007

(65) Prior Publication Data

US 2009/0306076 A1   Dec. 10, 2009

Related U.S. Application Data

(60) Provisional application No. 60/742,770, filed on Dec. 6, 2005, provisional application No. 60/830,242, filed on Jul. 12, 2006, provisional application No. 60/856,984, filed on Nov. 6, 2006.

(51) Int. Cl.
*A61K 31/5377* (2006.01)
*C07D 413/14* (2006.01)

(52) U.S. Cl. .................. 514/233.8; 514/235.2; 544/125; 544/140; 544/147; 544/148

(58) Field of Classification Search .............. 514/233.8, 514/235.2; 544/125, 140, 147, 148
See application file for complete search history.

(56) References Cited

U.S. PATENT DOCUMENTS

| 6,645,939 | B1 | 11/2003 | Durette et al. |
| 7,361,666 | B2 | 4/2008 | Aquila et al. |
| 2006/0235018 | A1 | 10/2006 | Coats et al. |
| 2007/0021422 | A1 | 1/2007 | Mabus et al. |
| 2008/0045535 | A1 | 2/2008 | Coats et al. |

OTHER PUBLICATIONS

F. D. King et al., "The Synthesis of 2-Morpholine Carboxylic Acid Derivatives and Their Elaboration to 1-AZA-4-Oxabicyclo[3.3.1]Nonan-6-One", Tetrahedron Letters, vol. 32, No. 20, pp. 2281-2284, 1991.

A. F. Abdel-Magid et al., "Reductive Amination of Aldehydes and Ketones by Using Sodium Triacetoxyborohydride", Tetrahhedron Letters, vol. 31, No. 39, pp. 5595-5598, 1990.

*Primary Examiner*—Kamal A Saeed
*Assistant Examiner*—Samantha L Shterengarts
(74) *Attorney, Agent, or Firm*—J. Eric Thies; Gerard M. Devlin

(57) ABSTRACT

The present invention is directed to morpholine carboxamide compounds which are antagonists of prokineticin receptors, in particular antagonists of prokineticin 2 receptors, and which are useful in the treatment or prevention of neurological and psychiatric disorders and diseases in which prokineticin receptors are involved. The invention is also directed to pharmaceutical compositions comprising these compounds and the use of these compounds and compositions in the prevention or treatment of such diseases in which prokineticin receptors are involved.

19 Claims, No Drawings

MORPHOLINE CARBOXAMIDE PROKINETICIN RECEPTOR ANTAGONISTS

CROSS REFERENCE TO RELATED APPLICATIONS

This application is a U.S. National Phase application under 35 U.S.C. §371 of PCT Application No. PCT/US2006/46330, filed Dec. 4, 2006, which claims priority under 35 U.S.C. §119 from U.S. Application No. 60/742,770, filed Dec. 6, 2005, U.S. Application No. 60/830,242, filed Jul. 12, 2006, and U.S. Application No. 60/856,984, filed Nov. 6, 2006.

BACKGROUND OF THE INVENTION

Circadian rhythms are exhibited by all eukaryotic plants and animals, including man. Biological rhythms are periodic fluctuations in biological processes over time, including circadian as well as seasonal variations. Circadian, or approximately 24-hour, rhythms include the production of biological molecules such as hormones, the regulation of body temperature, and behavior such as wakefulness, alertness, sleep and periods of activity. Circadian rhythms are endogenous, self-sustained oscillations over 24-hour periods found in organisms ranging from prokaryotes to humans (J S Takahashi, et al. Science, 217, 1104-1111 (1982)).

In nature, circadian rhythms are closely tied to environmental cues that impose a 24-hour pattern on many of these fluctuations. The regulation of circadian rhythms by signals from the environment involves "entrainment" of the circadian rhythm. The environmental signals which affect entrainment of the circadian rhythm are termed "zeitgebers", an example of which is the light-dark cycle. The control of many circadian rhythms in mammals is mediated by the portion of the brain called the suprachiasmatic nuclei (SCN). In humans as well as other mammals, the circadian clock, which controls all endogenous circadian rhythms, is located in the SCN of the hypothalamus. Activity, alertness, core body temperature, and many hormones all have endogenous circadian rhythms controlled by the SCN. The SCN is the primary pacemaker for circadian rhythms in mammals. Circadian rhythms are primarily entrained by the light-dark cycle. One of the most important and reproducible characteristics of a circadian clock is that it can respond to exogenous light/dark signals. The circadian clock is composed of three parts: light-input pathways, a clock, and effector pathways. Light signals are conveyed by the retina to the SCN, and the pineal gland produces melatonin (N-acetyl-5-methoxytryptamine), which is regulated by the SCN. Information regarding light is conveyed from the retina to the SCN via the direct retinohypothalamic tract (RHT), as well as indirectly via the lateral geniculate nucleus (LGN).

Although sleep is necessary for survival, its precise homeostatic contribution is unknown. Sleep is not a uniform state, but rather involves several stages that can be monitored by examining an individual's EEG. A non rapid eye movement (NREM) type (75 to 80% of total sleep time) sleep is characterized by 4 different stages, 1 to 4 (deepest level). Stage 1 sleep is drowsiness, in which the EEG displays a lower voltage, more mixed frequencies and deterioration of alpha rhythm relative to the EEG when the individual is awake. In stage 2, background activity similar to that of stage 1 is experienced, with bursts of slightly higher frequency "sleep spindles" and sporadic higher amplitude slow wave complexes. The third and fourth stages of sleep display increasing high amplitude slow wave activity. The separate sleep stage in which the individual undergoes rapid eye movement (REM) occupies the remainder of the sleep time and occurs 5 to 6 times during a normal nights sleep. REM sleep is characterized by a lower voltage, higher frequency EEG and other characteristics similar to those which occur when the individual is awake, whereas the other four sleep stages are categorized as NREM sleep.

Individuals vary widely in their requirements for sleep, which is influenced by a number of factors including their current emotional state. The natural aging process is associated with changes in a variety of circadian and diurnal rhythms. Age-related changes in the timing and structure of sleep are surprisingly common problems for older people, and are often associated with significant morbidity. With advancing age, the total amount of sleep tends to shorten. Stage 4 can decrease or disappear and sleep may become more fragmented and interrupted. Evaluation of sleep patterns in elderly people shows that the timing of sleep is also phase advanced, especially in women. This tendency to go to sleep and wake up earlier is very frustrating to older people who feel that they are out of step with the rest of the world. In addition, the quality of sleep in the elderly is diminished with a marked reduction in slow wave sleep, a reduction in the deep stages of sleep (especially stage 4), fragmentation of sleep and more frequent awakenings. Similarly, non-elderly people may exhibit disturbances in the normal sleep process. These changes in the structure of sleep have been correlated to more frequent napping, decreased daytime alertness and declining intellectual function and cognitive ability. Deprivation of REM sleep has been suggested to interfere with the memory consolidation involved in learning skills through repetitive activity, and slow wave sleep has been implicated as being important in consolidation of events into long term memory. Likewise, decreases in the length of REM stages of sleep may be associated with a decrease in cognitive function and learning, especially diminished retention of memory.

Numerous compounds are employed in the art to facilitate normal sleep and to treat sleep disorders and sleep disturbances, including e.g., sedatives, hypnotics, anxiolytics, antipsychotics, antianxiety agents, minor tranquilizers, melatonin agonists and antagonists, melatonergic agents, benzodiazepines, barbiturates, 5HT-2 antagonists, and the like. Similarly, physical methods have been employed to treat patients with sleep disorders such as the use of light therapy, constant positive airway pressure (CPAP) or the application of modulated electrical signals to selected nerves or nerve bundles.

Nevertheless, the known therapeutic regimens suffer from numerous problems, including residual sleepiness and related detrimental effects in daytime function, impairment of memory, potential for addiction, rebound insomnia, "REM rebound" which may be associated with increased dream intensity and the occurrence of nightmares, seizure induction, interaction with other medicines and alcohol to cause severe impairment and other health problems, and the like. Accordingly, a more physiological way to enhance sleep, and treat other neurological and psychiatric disorders and diseases would be highly desirable.

Prokineticins are secreted proteins that have roles in several biological functions, including circadian rhythm; sleep; angiogenesis; gastric contractility and motility; gastric acid and pepsinogen secretion; pain; and neurogenesis (see e.g., Bullock, et al., Mol. Pharmacol., 65(3):582-8 (2004); Cheng, et al., Nature., 417 (6887):405-10 (2002); Cheng, et al., BMC Neurosci., 6(1):17 (2005); Cottrell, et al., J. Neurosci., 24(10):2375-9 (2004); Li, et al., Mol. Pharmacol., 59(4): 692-8 (2001), Negri, et. al., Brit. Journal of Pharmacology, 137, 1147-1154 (2002), Zhou, Q.-Y. and Cheng, M. Y., FEBS Journal, 272, (2005), 5703-5709). Prokineticin 1 (PK1) and prokineticin 2 (PK2) induce cellular responses by binding to G-protein coupled receptors termed prokineticin receptor 1 (PKR1) and prokineticin receptor 2 (PKR2), resulting in activation of receptor signaling. Normal prokineticin receptor signaling contributes to the development and function of a variety of tissues in humans. If this normal signaling is disrupted, for example, due to disease or environmental conditions, unwanted changes can occur at the cellular, tissue and whole organism level. These changes can be manifested in a variety of conditions and diseases associated with improper prokineticin receptor signaling.

SUMMARY OF THE INVENTION

The present invention is directed to morpholine carboxamide compounds which are antagonists of prokineticin receptors, in particular antagonists of prokineticin 2 receptors, and which are useful in the treatment or prevention of neurological and psychiatric disorders and diseases in which prokineticin receptors are involved. The invention is also directed to pharmaceutical compositions comprising these compounds and the use of these compounds and compositions in the prevention or treatment of such diseases in which prokineticin receptors are involved.

DETAILED DESCRIPTION OF THE INVENTION

The present invention is directed to compounds of the formula I:

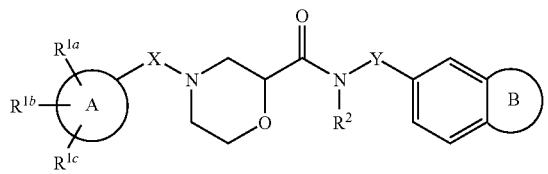

I wherein:

A is selected from the group consisting of phenyl, napthyl and heteroaryl;

B is selected from the group consisting of:

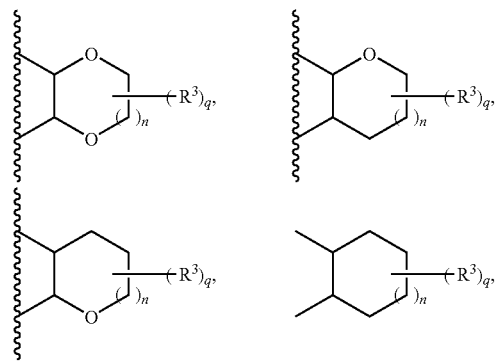

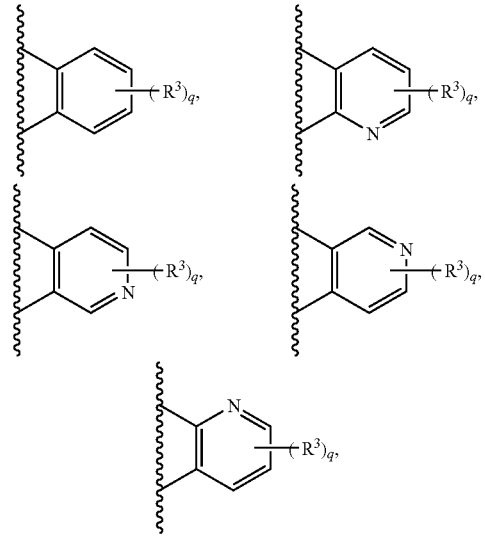

X and Y are independently —($C_{1-6}$alkylene)-, which is unsubstituted or substituted with one or more substituents selected from $R^{13}$, $R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —(C=O)$_m$—O$_p$—$C_{1-6}$alkyl, where m is 0 or 1, p is 0 or 1 (wherein if m is 0 or p is 0, a bond is present) and where the alkyl is unsubstituted or substituted with one or more substituents selected from $R^{13}$,
(5) —(C=O)$_m$—O$_p$—$C_{3-6}$cycloalkyl, where the cycloalkyl is unsubstituted or substituted with one or more substituents selected from $R^{13}$,
(6) —(C=O)$_m$—$C_{2-4}$alkenyl, where the alkenyl is unsubstituted or substituted with one or more substituents selected from $R^{13}$,
(7) —(C=O)$_m$—O$_p$-phenyl or —(C=O)$_m$—O$_p$-napthyl, where the phenyl or napthyl is unsubstituted or substituted with one or more substituents selected from $R^{13}$,
(8) —(C=O)$_m$—O$_p$-heterocycle, where the heterocycle is unsubstituted or substituted with one or more substituents selected from $R^{13}$,
(9) —(C=O)$_m$—NR$^{10}$R$^{11}$, wherein $R^{10}$ and $R^{11}$ are independently selected from the group consisting of:
(a) hydrogen,
(b) $C_{1-6}$alkyl, which is unsubstituted or substituted with $R^{13}$,
(c) $C_{3-6}$alkenyl, which is unsubstituted or substituted with $R^{13}$,
(d) cycloalkyl which is unsubstituted or substituted with $R^{13}$,
(e) phenyl, which is unsubstituted or substituted with $R^{13}$, and
(f) heterocycle, which is unsubstituted or substituted with $R^{13}$,
(10) —S(O)$_2$—NR$^{10}$R$^{11}$,
(11) —S(O)$_t$—R$^{12}$, where t is 0, 1 or 2 and where $R^{12}$ is selected from the definitions of $R^{10}$ and $R^{11}$,
(12) —CO$_2$H,

(13) —CN, and
(14) —NO$_2$;

R$^2$ is selected from the group consisting of:
(1) hydrogen,
(2) C$_{1-6}$alkyl, which is unsubstituted or substituted with one or more substituents selected from R$^{13}$,
(3) —C$_{3-6}$cycloalkyl, which is unsubstituted or substituted with one or more substituents selected from R$^{13}$,
(4) -phenyl which is unsubstituted or substituted with one or more substituents selected from R$^{13}$;

R$^3$ is independently selected from:
(1) hydrogen,
(2) halogen,
(3) hydroxy, and
(4) C$_{1-6}$alkyl, which is unsubstituted or substituted with one or more substituents selected from R$^{13}$,
or two R$^3$ at the same position are joined to form a furan, oxetane or pyran ring,
or two R$^3$ at adjacent positions are joined to form a phenyl ring;

R$^{13}$ is selected from the group consisting of:
(1) halogen,
(2) hydroxyl,
(3) —(C=O)$_m$—O$_p$—C$_{1-6}$alkyl, where the alkyl is unsubstituted or substituted with one or more substituents selected from R$^{14}$,
(4) —O$_n$—(C$_{1-3}$)perfluoroalkyl,
(5) —(C=O)$_m$—O$_p$—C$_{3-6}$cycloalkyl, where the cycloalkyl is unsubstituted or substituted with one or more substituents selected from R$^{14}$,
(6) —(C=O)$_m$—C$_{2-4}$alkenyl, where the alkenyl is unsubstituted or substituted with one or more substituents selected from R$^{14}$,
(7) —(C=O)$_m$—O$_p$-phenyl or —(C=O)$_m$—O$_p$-napthyl, where the phenyl or napthyl is unsubstituted or substituted with one or more substituents selected from R$^{14}$,
(8) —(C=O)$_m$—O$_p$-heterocycle, where the heterocycle is unsubstituted or substituted with one or more substituents selected from R$^{14}$,
(9) —(C=O)$_m$—NR$^{10}$R$^{11}$,
(10) —S(O)$_2$—NR$^{10}$R$^{11}$,
(11) —S(O)$_t$—R$^{12}$,
(12) —CO$_2$H,
(13) —CN, and
(14) —NO$_2$;

R$^{14}$ is selected from the group consisting of:
(1) hydroxyl,
(2) halogen,
(3) C$_{1-6}$alkyl,
(4) —C$_{3-6}$cycloalkyl,
(5) —O—C$_{1-6}$alkyl,
(6) —O(C=O)—C$_{1-6}$alkyl,
(7) —NH—C$_{1-6}$alkyl,
(8) phenyl,
(9) heterocycle,
(10) —CO$_2$H, and
(11) —CN;

n is 0, 1, 2, 3, 4, 5 or 6;
q is 0, 1, 2, 3 or 4;
or an N-oxide thereof or an individual enantiomer or diastereomer thereof or a pharmaceutically acceptable salt thereof.

An embodiment of the present invention includes compounds of the formula Ia':

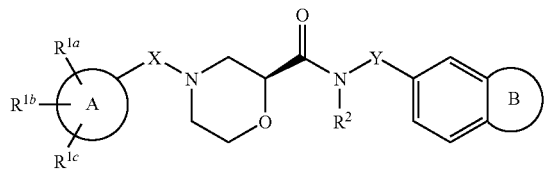

wherein R$^{1a}$, R$^{1b}$, R$^{1c}$, R$^2$, R$^3$, A, X, Y, n and q are defined herein; or an individual enantiomer or diastereomer thereof or a pharmaceutically acceptable salt thereof.

An embodiment of the present invention includes compounds of the formula Ia":

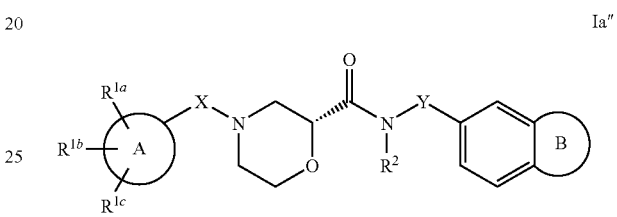

wherein R$^{1a}$, R$^{1b}$, R$^{1c}$, R$^2$, R$^3$, A, X, Y, n and q are defined herein; or an individual enantiomer or diastereomer thereof or a pharmaceutically acceptable salt thereof.

An embodiment of the present invention includes compounds of the formula Ib:

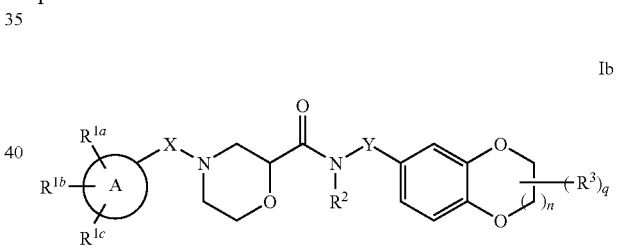

wherein R$^{1a}$, R$^{1b}$, R$^{1c}$, R$^2$, R$^3$, A, X, Y, n and q are defined herein; or an individual enantiomer or diastereomer thereof or a pharmaceutically acceptable salt thereof.

An embodiment of the present invention includes compounds of the formula Ic:

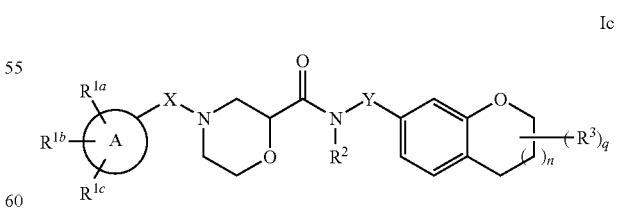

wherein R$^{1a}$, R$^{1b}$, R$^{1c}$, R$^2$, R$^3$, A, X, Y, n and q are defined herein; or an individual enantiomer or diastereomer thereof or a pharmaceutically acceptable salt thereof.

An embodiment of the present invention includes compounds of the formula Id:

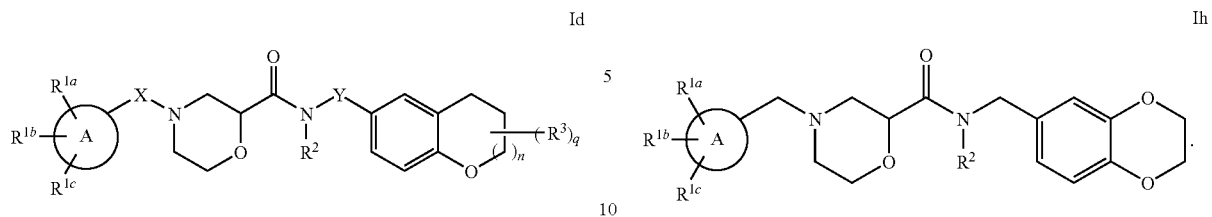

Id wherein $R^{1a}$, $R^{1b}$, $R^{1c}$, $R^2$, $R^3$, A, X, Y, n and q are defined herein; or an individual enantiomer or diastereomer thereof or a pharmaceutically acceptable salt thereof.

An embodiment of the present invention includes compounds of the formula Ie:

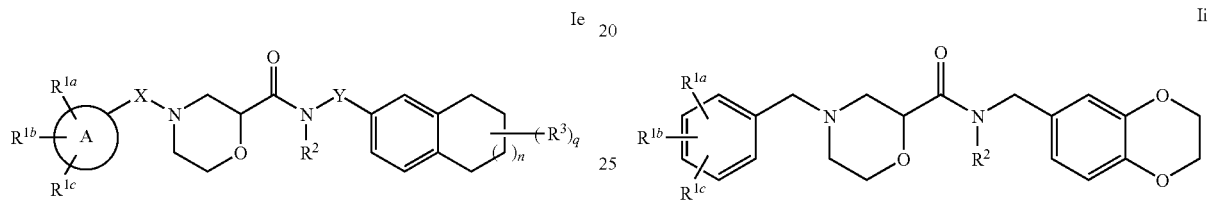

Ie wherein $R^{1a}$, $R^{1b}$, $R^{1c}$, $R^2$, $R^3$, A, X, Y, n and q are defined herein; or an individual enantiomer or diastereomer thereof or a pharmaceutically acceptable salt thereof.

An embodiment of the present invention includes compounds of the formula If:

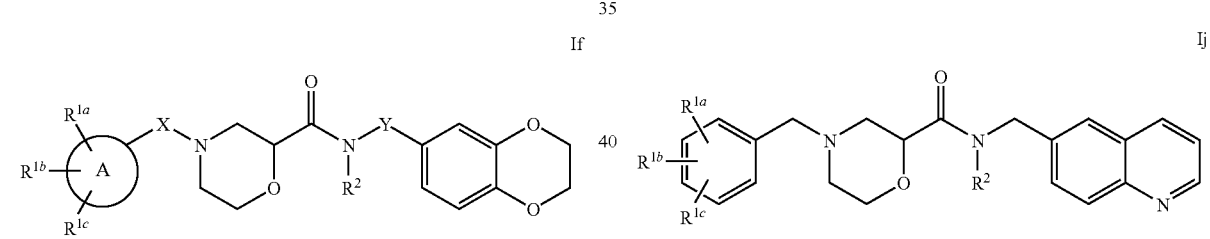

If wherein $R^{1a}$, $R^{1b}$, $R^{1c}$, $R^2$, A, X and Y are defined herein; or an individual enantiomer or diastereomer thereof or a pharmaceutically acceptable salt thereof.

An embodiment of the present invention includes compounds of the formula Ig:

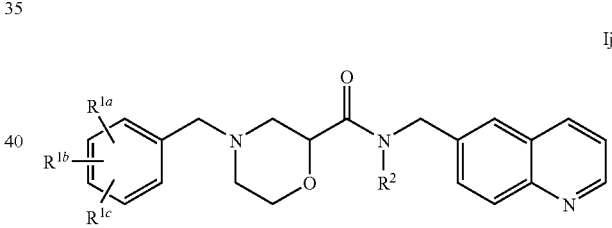

Ig wherein $R^{1a}$, $R^{1b}$, $R^{1c}$, $R^2$, $R^3$, A, X, Y and q are defined herein; or an individual enantiomer or diastereomer thereof or a pharmaceutically acceptable salt thereof.

An embodiment of the present invention includes compounds of the formula Ihg:

Ih wherein $R^{1a}$, $R^{1b}$, $R^{1c}$ and $R^2$ are defined herein; or an individual enantiomer or diastereomer thereof or a pharmaceutically acceptable salt thereof.

An embodiment of the present invention includes compounds of the formula Ii:

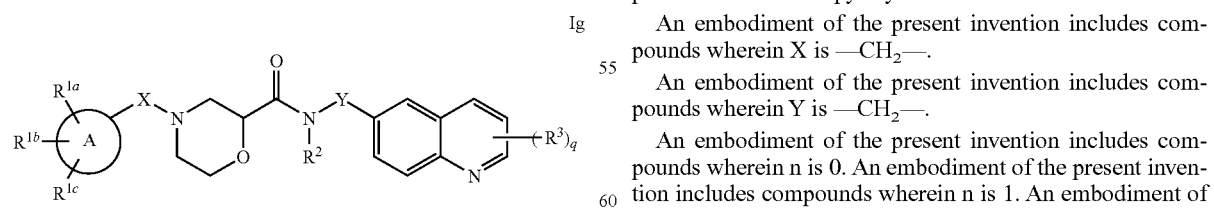

Ii wherein $R^{1a}$, $R^{1b}$, $R^{1c}$ and $R^2$ are defined herein; or an individual enantiomer or diastereomer thereof or a pharmaceutically acceptable salt thereof.

An embodiment of the present invention includes compounds of the formula Ij:

Ij wherein $R^{1a}$, $R^{1b}$, $R^{1c}$ and $R^2$ are defined herein; or an individual enantiomer or diastereomer thereof or a pharmaceutically acceptable salt thereof.

An embodiment of the present invention includes compounds wherein A is phenyl.

An embodiment of the present invention includes compounds wherein A is pyridyl.

An embodiment of the present invention includes compounds wherein X is —$CH_2$—.

An embodiment of the present invention includes compounds wherein Y is —$CH_2$—.

An embodiment of the present invention includes compounds wherein n is 0. An embodiment of the present invention includes compounds wherein n is 1. An embodiment of the present invention includes compounds wherein n is 2. An embodiment of the present invention includes compounds wherein n is 3. An embodiment of the present invention includes compounds wherein n is 5.

An embodiment of the present invention includes compounds wherein $R^{1a}$, $R^{1b}$ and $R^{1c}$ are independently selected from the group consisting of:

(1) hydrogen,
(2) halogen,
(3) $C_{1-6}$alkyl, which is unsubstituted or substituted with halogen, hydroxyl, phenyl or —O—$C_{1-6}$alkyl,
(4) $C_{2-4}$alkenyl, which is unsubstituted or substituted with $C_{3-6}$cycloalkyl or phenyl,
(5) —O—$C_{1-6}$alkyl, which is unsubstituted or substituted with halogen, hydroxyl, phenyl or —O—$C_{1-6}$alkyl,
(6) phenyl, which is unsubstituted or substituted with halogen, hydroxyl, $C_{1-6}$alkyl, —O—$C_{1-6}$alkyl, —SH, —S—$C_{1-6}$alkyl, —NO$_2$, —CO$_2$H, or —CN,
(7) —NR$^{10}$R$^{11}$, wherein R$^{10}$ and R$^{11}$ are independently selected from hydrogen and $C_{1-6}$alkyl,
(8) tetrazolyl,
(9) thienyl,
(10) triazolyl,
(11) benzothienyl,
(12) pyrazolyl,
(13) imidazolyl,
(14) —NO$_2$,
(15) hydroxyl, and
(16) —CN.

Within this embodiment, the present invention includes compounds wherein R$^{1b}$ is hydrogen, R$^{1c}$ is hydrogen and R$^{1a}$ is selected from the group consisting of:
(1) hydrogen,
(2) halogen,
(3) $C_{1-6}$alkyl, which is unsubstituted or substituted with halogen, hydroxyl or phenyl,
(4) $C_{2-4}$alkenyl, which is unsubstituted or substituted with $C_{3-6}$cycloalkyl or phenyl,
(5) —O—$C_{1-6}$alkyl, which is unsubstituted or substituted with halogen, hydroxyl, phenyl or —O—$C_{1-6}$alkyl,
(6) phenyl, which is unsubstituted or substituted with halogen, hydroxyl, $C_{1-6}$alkyl, —O—$C_{1-6}$alkyl, —SH, —S—$C_{1-6}$alkyl, —NO$_2$, —CO$_2$H, or —CN,
(7) —NR$^{10}$R$^{11}$, wherein R$^{10}$ and R$^{11}$ are independently selected from hydrogen and $C_{1-6}$alkyl,
(8) tetrazolyl,
(9) thienyl,
(10) triazolyl,
(11) benzothienyl,
(12) pyrazolyl,
(13) imidazolyl,
(14) —NO$_2$,
(15) hydroxyl, and
(16) —CN.

Within this embodiment, the present invention includes compounds wherein R$^{1b}$ is hydrogen, R$^{1c}$ is hydrogen and R$^{1a}$ selected from the group consisting of:
(1) hydrogen,
(2) fluoro,
(3) —O—$C_{1-6}$alkyl, and
(4) phenyl.

Within this embodiment, the present invention includes compounds wherein A is phenyl, R$^{1b}$ is hydrogen, R$^{1c}$ is hydrogen and R$^{1a}$ selected from the group consisting of:
(1) hydrogen,
(2) fluoro,
(3) —O—$C_{1-6}$alkyl, and
(4) phenyl.

Further within this embodiment, the present invention includes compounds wherein A is phenyl, R$^{1b}$ is hydrogen, R$^{1c}$ is hydrogen and R$^{1a}$ selected from the group consisting of:
(1) hydrogen,
(2) fluoro, and
(3) —O—CH$_3$.

An embodiment of the present invention includes compounds wherein R$^2$ is $C_{1-6}$alkyl, which is unsubstituted or substituted with one or more substituents selected from R$^{13}$.

Within this embodiment, the present invention includes compounds wherein R$^2$ is selected from the group consisting of:
(1) $C_{1-6}$alkyl, and
(2) $C_{1-6}$alkyl-$C_{3-6}$cycloalkyl.

Further within this embodiment, the present invention includes compounds wherein R$^2$ is $C_{1-6}$alkyl.

Further within this embodiment, the present invention includes compounds wherein R$^2$ is isopropyl.

An embodiment of the present invention includes compounds wherein R$^3$ is independently selected from:
(1) hydrogen,
(2) halogen, and
(3) $C_{1-6}$alkyl.

Within this embodiment, the present invention includes compounds wherein R$^3$ is independently selected from:
(1) hydrogen,
(2) fluoro, and
(3) methyl.

An embodiment of the present invention includes compounds wherein q is 0 and R$^3$ is absent.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to embrace all such isomeric forms of these compounds. Formula I shows the structure of the class of compounds without preferred stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halo or halogen as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (termed "heteroaryl" herein) include benzoimidazolyl, benzimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The subject compounds are useful in a method of antagonizing prokineticin receptor activity in a patient such as a mammal in need of such inhibition comprising the administration of an effective amount of the compound. The present invention is directed to the use of the compounds disclosed herein as antagonists of prokineticin receptors activity. In addition to primates, especially humans, a variety of other mammals can be treated according to the method of the present invention.

The present invention is further directed to the use of a compound of the present invention, or a pharmaceutically acceptable salt thereof, for the manufacture of a medicament for human therapy or for antagonizing prokineticin receptors activity or treating the disorders and diseases noted herein in humans and animals.

The subject treated in the present methods is generally a mammal, preferably a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as prokineticin receptor antagonists may be readily determined without undue experimentation by methodology well known in the art, including the prokineticin receptor assay. The Fluorometric Imaging Plate Reader (FLIPR) assay for prokineticin 2 receptor activity was conducted as follows. CHONFAT cells expressing chimp PKR2 receptors were plated at 20 K cells/well in clear-bottomed, poly-D-lysine coated 384-well plates from Becton-Dickinson using a Labsystems Multidrop. The plated cells were grown overnight at 37° C. in the presence of 6% $CO_2$. The following day, the cells were washed with 3×100 µl assay buffer (Hanks Balanced Salt Solution containing 20 mM HEPES, 2.5 mM probenecid, and 0.1% bovine serum albumin) using a Skatron Embla cell washer. The cells were incubated with 1 µM Fluo-4AM (Molecular Probes) for 1 h at 37° C. and 6% $CO_2$. The extracellular dye was removed by washing as described above. $Ca^{2+}$ flux was measured using Molecular Devices $FLIPR_{384}$, fluorometric imaging plate reader. For antagonist determination, the cells were incubated with various concentrations of compound for 5 min prior to the addition of synthetic rhesus PK2 (1 nM final concentration)

The intrinsic prokineticin receptor antagonist activity of a compound which may be used in the present invention may be determined by this and other assays. In particular, the compounds of the following examples had activity in antagonizing the prokineticin receptor in the aforementioned assays, generally with an $IC_{50}$ of less than about 10 µM. Preferred compounds within the present invention had activity in antagonizing the prokineticin receptor in the aforementioned assays with an $IC_{50}$ of less than about 1 µM. Such a result is indicative of the intrinsic activity of the compounds in use as antagonists of prokineticin receptor activity. With respect to other morpholinyl compounds, the present compounds exhibit unexpected properties, such as with respect to increased selectivity with respect to other receptors and/or ion channels.

Prokineticin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with prokineticin receptors, including one or more of the following conditions or diseases: modulating circadian rhythm; treating conditions associated with circadian rhythmicity as well as mental and physical disorders associated with travel across time zones and with rotating shift-work schedules, conditions due to drugs which cause reductions in REM sleep as a side effect, non-24-hour sleep-wake syndrome, rapid time-zone change syndrome, work-shift syndrome, delayed phase sleep syndrome, advanced sleep phase syndrome, irregular sleep-wake pattern syndrome, syndrome associated with decreased amplitude, seasonal affective disorder; sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing the amount of Delta sleep early in the sleep cycle, increasing REM sleep late in the sleep cycle; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, obstructive sleep apnea, wakefulness, nocturnal myoclonus, REM sleep interruptions, jet-lag, shift workers' sleep disturbances, dyssomnias, night terror, insomnia's associated with depression, emotional/mood disorders, Alzheimer's disease or cognitive impairment, as well as sleep walking and enuresis, and sleep disorders which accompany aging; fibromyalgia; syndromes which are manifested by non-restorative sleep and muscle pain or sleep apnea which is associated with respiratory disturbances during sleep; conditions which result from a diminished quality of sleep; heart disease, abnormal heart rhythms and arrythmias, myocardial infarction, congestive heart failure, coronary heart disease, sudden death, stroke, sexual and reproductive dysfunction, such as impaired fertility, infertility, diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing trained performance; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, seizure disorders, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute pain, chronic pain, visceral pain, inflammatory pain, neuropathic pain, severe pain, intractable pain, post-traumatic pain, bone and joint pain (osteoarthritis), repetitive motion pain, dental pain, cancer pain, myofascial pain (muscular injury, fibromyalgia), perioperative pain (general surgery, gynecological), migraine, migraine headache, pain resulting from traumatic nerve injury, nerve compression or entrapment, postherpetic neuralgia, trigeminal neuralgia, diabetic neuropathy, chronic lower back pain, phantom limb pain, pelvic pain, chronic pelvic pain, neuroma pain, complex regional pain syndrome, chronic arthritic pain and related neuralgias, pain associated with or resulting from cancer, chemotherapy, HIV and HIV treatment-induced neuropathy; as a local anesthetic; gastrointestinal (GI) diseases; irritable bowel syndrome (IBS, including diarrhea-predominant, as well as alternating diarrhea/constipation forms of IBS); inflammatory bowel disease (IBD, including ulcerative colitis, and Crohn's disease); gastroesophogeal reflux disease (GERD); secretory diarrhea; secretory bowel disorders induced by pathogens; visceral pain or hyperalgesia such as associated with IBS or IBD; cancers of the gastrointestinal tract, cancers of the reproductive organs, testicular cancer, ovarian cancer, Leydig cell carcinoma, cancers of the small or large bowel; and polycystic ovary syndrome.

Thus, in preferred embodiments the present invention provides methods for: enhancing the quality of sleep; augmenting sleep maintenance; increasing REM sleep; increasing slow wave sleep; decreasing fragmentation of sleep patterns; treating insomnia; modulating circadian rhythm; treating conditions associated with circadian rhythmicity as well as mental and physical disorders associated with travel across time zones and with rotating shift-work schedules, conditions due to drugs which cause reductions in REM sleep as a side effect; enhancing cognition; increasing memory retention; treating or controlling depression; treating, controlling, ameliorating or reducing the risk of epilepsy, including absence epilepsy; treating essential tremor; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of the compound of the present invention.

The subject compounds are further useful in a method for the prevention, treatment, control, amelioration, or reduction of risk of the diseases, disorders and conditions noted herein.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of prokineticin receptor. The dosage range will generally be about 0.5 mg to 1.0 g. per patient per day which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Pharmaceutical compositions of the present invention may be provided in a solid dosage formulation preferably comprising about 0.5 mg to 500 mg active ingredient, more preferably comprising about 1 mg to 250 mg active ingredient. The pharmaceutical composition is preferably provided in a solid dosage formulation comprising about 1 mg, 5 mg, 10 mg, 25 mg, 50 mg, 100 mg, 200 mg or 250 mg active ingredient.

For oral administration, the compositions are preferably provided in the form of tablets containing 1.0 to 1000 milligrams of the active ingredient, particularly 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in conjunction with other compounds which are known in the art to be useful for enhancing sleep quality and preventing and treating sleep disorders and sleep disturbances, including e.g., sedatives, hypnotics, antidepressants, anxiolytics, antipsychotics, antianxiety agents, benzodiazepines, barbiturates, cyclopyrrolones, 5HT-2 antagonists, histamine antagonists, histamine H3 inverse agonists, imidazopyridines, pyrazolopyrimidines, minor tranquilizers, melatonin agonists and antagonists, melatonergic agents, orexin antagonists, orexin agonists, and the like, such as: adinazolam, allobarbital, alonimid, alprazolam, amitriptyline, amobarbital, amoxapine, armodafinil, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, eplivanserin, estazolam, esopiclone, ethanol, ethchlorvynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, maprotiline, mecloqualone, melatonin, mephobarbital, meprobamate, methaqualone, midaflur, midazolam, modafinil, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, pruvanserin, quazepam, rameleton, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, zopiclone, and salts thereof, and combinations thereof, and the like, or the compound of the present invention may be administered in conjunction with the use of physical methods such as with light therapy or electrical stimulation.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT$_{1A}$ agonists or antagonists, especially 5-HT$_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H$_3$ antagonists; AMPA agonists; PDE IV inhibitors; GABA$_A$ inverse agonists; or neuronal nicotinic agonists.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with an anti-seizure agent such as carbamazepine, clonazepam, divalproex, ethosuximide, felbamate, fosphenytoin, gabapentin, lamotrigine, levetiracetam, lorazepam, midazolam, oxcarbazepine, phenobarbital, phenyloin, primidone, tiagabine, topiramate, valproate, vigabatrin or zonisamide. In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene, trifluoperazine or valproic acid.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an opiate agonist or antagonist, a calcium channel antagonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, gabapentin, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DMSO: dimethylsulfoxide; EDC: N-(3-Dimethylaminopropyl)-N'-ethylcarbodiimide; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; $SOCl_2$: thionyl chloride; CDI: carbonyl diimidazole; rt: room temperature; HPLC: high performance liquid chromatography. The compounds of the present invention can be prepared in a variety of fashions.

SCHEME 1

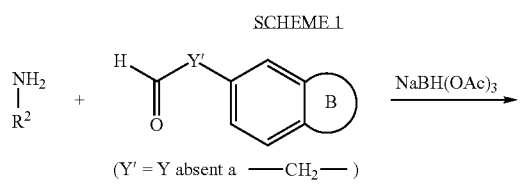

($Y' = Y$ absent a —$CH_2$—)

-continued

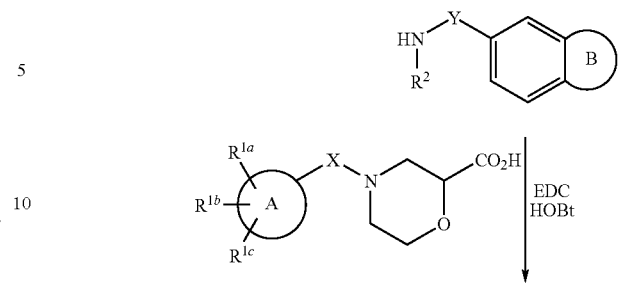

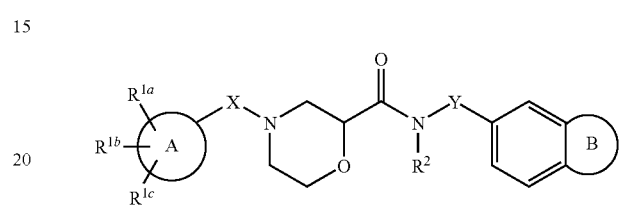

Compounds of the formula I can be prepared as depicted in Scheme 1. In the first step, an aryl aldehyde is reductively aminated with an excess of an alkyl amine in a suitable organic solvent such as 1,2-dichloroethane using sodium triacetoxy borohydride in the presence of acetic acid (A. F. Abdel-Magid, C. A. Maryanoff and K. G. Carson, Tetrahedron Letters, 1990, 5595-5598). The resulting secondary amine is coupled with a 4-alkyl morpholine-2-carboxylic acid such as 4-benzylmorpholine-2-carboxylic acid using standard amide coupling reagents such as EDC with HOAt or HOBt in a suitable organic solvent such as dichloromethane, THF or DMF. The 4-alkylmorpholine-2-carboxylic acids may be prepared as described in the literature (cf. F. D. King and R. T. Martin, Tetrahedron Letters, 1991, 2281-2284) or purchased from commercial sources.

SCHEME 2

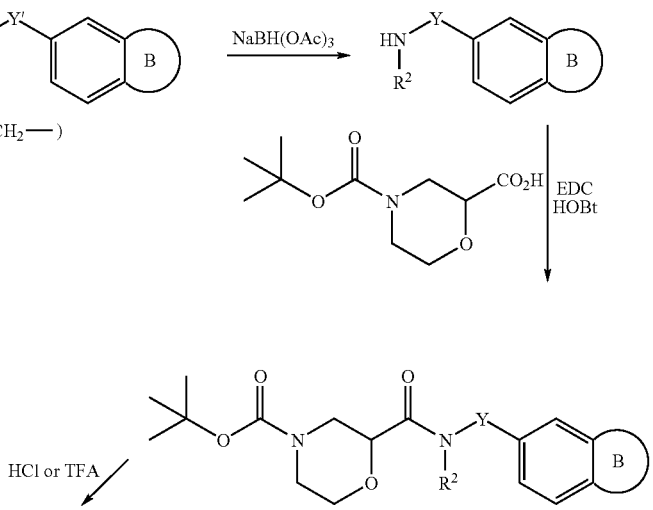

($Y' = Y$ absent a —$CH_2$—)

HCl or TFA

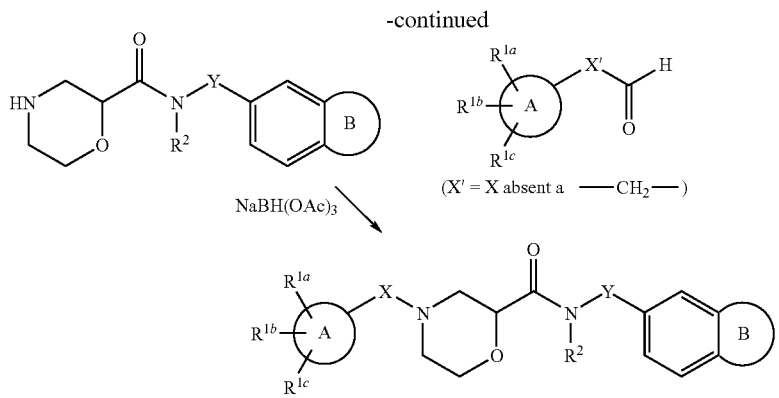

Compounds of the formula I can alternatively be prepared as depicted in Scheme 2. In the first step, an aryl aldehyde is reductively aminated with an excess of an alkyl amine in a suitable organic solvent such as 1,2-dichloroethane using sodium triacetoxy borohydride in the presence of acetic acid (A. F. Abdel-Magid, C. A. Maryanoff and K. G. Carson, Tetrahedron Letters, 1990, 5595-5598). The resulting secondary amine is coupled with an N-protected morpholine-2-carboxylic acid such as 4-(tert-butoxycarbonyl)morpholine-2-carboxylic acid using standard amide coupling reagents such as EDC with HOAt or HOBt in a suitable organic solvent such as dichloromethane, THF or DMF. The tert-butoxycarbonyl type of protecting group is easily removed by brief treatment with acid such as TFA or HCl in dioxane. The resulting morpholine-2-carboxamide intermediate is reductively alkylated in a suitable organic solvent such as THF or 1,4-dioxane with an aryl, heteroaryl or alkyl aldehyde using sodium triacetoxy borohydride in the presence of acetic acid (A. F. Abdel-Magid, C. A. Maryanoff and K. G. Carson, Tetrahedron Letters, 1990, 5595-5598).

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Example 1

(±)-4-Benzyl-N-(3,4-dihydro-2H-1,5-benzodioxepin-7-ylmethyl)-N-isobutylmorpholine-2-carboxamide

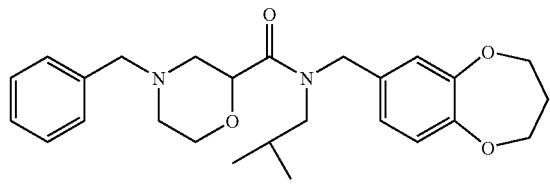

Step 1:
3,4-dihydro-2H-1,5-benzodioxepine-7-carbaldehyde

A mixture of 35 g of 3,5-dihydroxybenzaldehyde, 50 g (0.97 equiv) of 1,3-dibromopropane and 127 g (1.5 equiv) of cesium carbonate in 1 L of anhydrous acetonitrile was heated under nitrogen to 60° C. overnight. The mixture was allowed to cool, then filtered and concentrated under reduced pressure. The residue was partitioned between 500 mL of ethyl acetate and 100 mL of saturated sodium carbonate then dried over magnesium sulfate and concentrated under reduced pressure. Purification by flash chromatography (0-20% ethyl acetate in hexanes) gave the product as clear oil. MS (m+1)= 179.1; 1H NMR (400 MHz, CDCl3) 9.82 (s, 1H), 7.42 (m, 2H), 7.02 (m, 1H), 4.32 (t, 2H), 4.24 (t, 2H), 2.22 (m, 2H).

Step 2: N-(3,4-dihydro-2H-1,5-benzodioxepin-7-ylmethyl)-2-methylpropan-1-amine

To an ice cold mixture of 15 g of 3,4-dihydro-2H-1,5-benzodioxepine-7-carbaldehyde and 67 mL (8 equiv) of isobutylamine in 100 mL of 1,2-dichloroethane was added 50 mL (10 equiv) of acetic acid and 25 g (1.4 equiv) of sodium triacetoxyborohydride. The mixture was allowed to warm and stir overnight then diluted with 500 mL of chloroform and washed with 500 mL of 5N NaOH. The aqueous layer was extracted with 4 additional 100 mL portions of chloroform and the combined extracts dried over magnesium sulfate and concentrated under reduced pressure. After drying under vacuum the product was obtained as clear oil: MS (m+1)= 236.2; 1H NMR (400 MHz, CDCl3) 7.0-6.8 (m, 3H), 4.2 (q, 4H), 3.65 (s, 2H), 2.42 (d, 2H), 2.2 (m, 2H), 1.8 (m, 1H), 0.9 (d, 6H).

Step 3: (±)-4-Benzyl-N-(3,4-dihydro-2H-1,5-benzodioxepin-7-ylmethyl)-N-isobutylmorpholine-2-carboxamide A mixture of 0.1 g of N-(3,4-dihydro-2H-1,5-benzodioxepin-7-ylmethyl)-2-methylpropan-1-amine, 0.1 g of (±)-4-benzylmorpholine-2-carboxylic acid hydrochloride, 0.05 g of 1-hydroxybenzotriazole hydrate and 0.1 g of 1-ethyl-3-(3-dimethylaminopropyl)carbodiimide hydrochloride and 0.1 mL of triethylamine in 10 mL of dichloromethane was stirred overnight. The mixture was concentrated under educed pressure and partitioned between 25 mL of ethyl acetate and 25 mL of saturated sodium carbonate, dried over magnesium sulfate and concentrated under reduced pressure. Preparative TLC (75% ethyl acetate/hexanes) gave the product as a resin: MS (m+1)=439.3; H NMR (400 MHz, CDCl3) 7.3-7.2 (m, 5H), 6.9 (m, 1H), 6.8-6.7 (m, 2H), 4.62 (m, 1H), 4.4-4.3 (m, 1H), 4.2 (m, 4H), 3.9 (t, 3H), 3.7-3.22 (overlapping m, 3H), 3.3 (m, 1H), 3.2 (m, 1H), 3.0 (m, 1H), 2.9 (m, 2H), 2.62 (t, 1H) 2.5 (t, 1H), 2.3-2.1 (overlapping m, 3H), 2.0 (m, 1H), 0.85 (m, 6H).

Step 4: (S)-(+)-4-benzyl-N-(3,4-dihydro-2H-1,5-benzodioxepin-7-ylmethyl)-N-isobutylmorpholine-2-carboxamide and (R)-(−)-4-benzyl-N-(3,4-dihydro-2H-1,5-benzodioxepin-7-ylmethyl)-N-isobutylmorpholine-2-carboxamide. Resolution into the pure enantiomers was performed by preparative HPLC using isocratic elution on ChiralPak AD at 1 mL/min, eluting with 100% ethanol. Under these conditions, the (R)-(−)-isomer elutes second after the (S)-(+)-isomer. (S)-(+)-4-benzyl-N-(3,4-dihydro-2H-1,5-benzodioxepin-7-ylmethyl)-N-isobutylmorpholine-2-carboxamide: $[\alpha]_D^{25°\ C.}=+10°$ (c=1, MeOH), (R)-(−)-4-benzyl-N-(3,4-dihydro-2H-1,5-benzodioxepin-7-ylmethyl)-N-isobutylmorpholine-2-carboxamide: $[\alpha]_D^{25°\ C.}=-10°$ (c=1, MeOH)

Example 2

(−)-(2R)—N-(3,4-dihydro-2H-1,5-benzodioxepin-7-ylmethyl)-N-isobutyl-4-(2-methoxybenzyl)morpholine-2-carboxamide

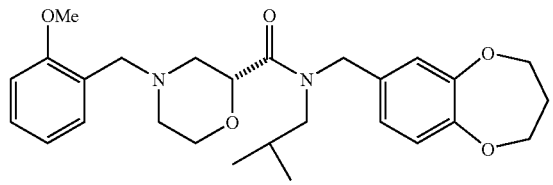

Step 1: ethyl (2R)-4-benzylmorpholine-2-carboxylate

Resolution into the pure enantiomers was performed by preparative HPLC using isocratic elution on Chiralcel OJ at 60 mL/min, eluting with 20% ethanol, 20% methanol and 60% hexanes with 1 mL/L diethylamine as modifier. Under these conditions, the (R)-(−)-isomer elutes first. (−)-Ethyl (2R)-4-benzylmorpholine-2-carboxylate: $[\alpha]_D^{25°\ C.}=-31.75°$ (c 2.0, MeOH) MS (m+1)=179.1; 1H NMR (400 MHz, CDCl3) 7.3 (m, 5H), 4.22 (q, 2H), 4.02 (dt, 1H), 3.7 (td, 1H), 3.5 (dd, 1H), 2.22 (m, 2H), 2.95 (d, 1H), 2.6 (d, 1H), 2.4-2.3 (m, 2H), 1.3 (t, 3H). (+)-Ethyl (2S)-4-benzylmorpholine-2-carboxylate: $[\alpha]_D^{25°\ C.}=+32.1°$ (c=2.3, MeOH).

Step 2: (−)-(2R)-2,4-morpholinedicarboxylic acid, 4-(1,1-dimethylethyl) 2-ethyl ester A mixture of 10 g of ethyl (2R)-4-benzylmorpholine-2-carboxylate, 9 g (1.05 equiv) of ditertbutyldicarbonate, and 1 g of 10% palladium on carbon catalyst in 100 mL of ethanol was shaken under 55 psi of hydrogen overnight. The mixture was filtered and concentrated under reduced pressure. Drying under vacuum gave the product as a white solid (10.5 g) suitable for the next step. Further purification could be effected by trituration with hexane: $[\alpha]_D^{25°\ C.}=-50°$ (c=1.1, MeOH); 1H NMR (400 MHz, CDCl3) 4.25 (q, 2H), 4.08 (d, 1H), 4.0 (d, 1H), 3.8 (d, 1H), 3.7 (t, 1H), 3.1 (m, 2H), 2.95 (d, 1H), 1.5 (s, 9H) 1.3 (t, 3H).

Step 3: (−)-(2R)-4-(tert-butoxycarbonyl)morpholine-2-carboxylic acid

A mixture of 10 g of (−)-(2R)-2,4-morpholinedicarboxylic acid, 4-(1,1-dimethylethyl) 2-ethyl ester, 150 mL of dioxane, 40 mL of water and 6.8 g of lithium hydroxide monohydrate was stirred at room temperature for 3 hrs then under reduced pressure. The residue was partitioned between 3×50 mL of ethyl acetate and 200 mL of ice cold 1N hydrochloric acid. The extracts were dried over magnesium sulfate and concentrated under reduced pressure. Drying under vacuum gave the product as a white solid (96%): $[\alpha]_D^{25°\ C.}=-44.7°$ (c=1.0, MeOH); 1H NMR (400 MHz, CDCl3) 4.08 (d, 1H), 4.0 (d, 1H), 3.8 (d, 1H), 3.6 (t, 1H), 3.08 (t, 2H), 2.95 (d, 1H), 1.45 (s, 9H).

Step 4: (−)-4-Benzyl-N-(3,4-dihydro-2H-1,5-benzodioxepin-7-ylmethyl)-N-isobutylmorpholine-2-carboxamide A mixture of 5.6 g of N-(3,4-dihydro-2H-1,5-benzodioxepin-7-ylmethyl)-2-methylpropan-1-amine, 5.0 g of (−)-(2R)-4-(tert-butoxycarbonyl)morpholine-2-carboxylic acid, 0.8 g of 1-hydroxybenzotriazole hydrate and 5 g of 1-ethyl-3-(3-dimethylaminopropyl)carbodiimide hydrochloride and 3 mL of triethylamine in 100 mL in dichloromethane was stirred overnight. The mixture was concentrated under reduced pressure and partitioned between 100 mL of ethyl acetate and 100 mL of saturated sodium carbonate, dried over magnesium sulfate and concentrated under reduced pressure. Flash chromatography (20%-50% ethyl acetate/hexanes gradient elution) gave the product as a resin: MS (m+1)=449.3; H NMR (400 MHz, CDCl3) 7.3-6.7 (complex m, 5H), 4.6 (br d, 1H), 6.8-6.7 (m, 2H), 4.4 (d, 1H), 4.2 (m, 4H), 4.15 (q, 1H), 4.08 (br d, 1H), 3.95 (m, 1H), 3.5 (m, 1H), 3.2 (m, 1H), 3.0 (dd, 1H), 2.2 (m, 1H), 2.0 (m, 1H) 1.45 (2×s, 9H), 0.9 (dd, 6H).

Step 5: (−)-((2R)—N-(3,4-dihydro-2H-1,5-benzodioxepin-7-ylmethyl)-N-isobutylmorpholine-2-carboxamide A mixture of 8.79 g of (−)-4-benzyl-N-(3,4-dihydro-2H-1,5-benzodioxepin-7-ylmethyl)-N-isobutylmorpholine-2-carboxamide and 50 mL of 4N HCl in dioxane was stirred for 3 hrs at room temperature, then concentrated under reduced pressure. The residue was partitioned between 3×50 mL of chloroform and 20 mL of saturated sodium carbonate, dried over magnesium sulfate and concentrated under reduced pressure. Drying under vacuum gave the product as a resin: MS (m+1)=349.3; H NMR (400 MHz, CDCl3) 7.3-6.7 (complex m, 5H), 4.6 (br d, 1H), 6.8-6.7 (m, 2H), 4.4 (d, 1H), 4.2 (m, 4H), 4.15 (q, 1H), 4.08 (br d, 1H), 3.95 (m, 1H), 3.5 (m, 1H), 3.2 (m, 1H), 3.0 (dd, 1H), 2.2 (m, 1H), 2.0 (m, 1H) 1.45 (2×s, 9H), 0.9 (dd, 6H).

Step 6: (−)-(2R)—N-(3,4-dihydro-2H-1,5-benzodioxepin-7-ylmethyl)-N-isobutyl-4-(2-methoxybenzyl)morpholine-2-carboxamide A mixture of 0.1 g of (−)-(2R)—N-(3,4-dihydro-2H-1,5-benzodioxepin-7-ylmethyl)-N-isobutylmorpholine-2-carboxamide, 0.05 g of 2-methoxybenzaldehyde, 0.1 g of sodium triacetoxyborohydride, 0.1 mL of acetic acid and 5 mL of THF was stirred overnight room temperature, then concentrated under reduced pressure. The residue was partitioned between 3×10 mL of ethyl acetate and 10 mL of saturated sodium carbonate, dried over magnesium sulfate and concentrated under reduced pressure. Preparative TLC eluting with 25% ethyl acetate in hexanes gave the product as a resin: $[\alpha]_D^{23°\ C.}$=5.7° (c=1.0, MeOH); MS (m+1)=469.3; 1H NMR (500 MHz, CDCl3) 7.34-7.21 (m, 2H), 6.93-6.85 (m, 3H), 6.81-6.71 (m, 2H), 4.64 (m, 1H), 4.41-4.17 (m, 6H), 3.3 (m, 1H), 3.81 (d, 3H), 3.73-3.60 (m, 3H), 3.33-3.16 (m, 1H), 3.01-2.88 (m, 2H), 2.71 (m, 1H), 2.53 (t, 1H) 2.39-2.28 (m, 1H), 2.18 (m, 2H), 1.97 (m, 1H), 0.87 (m, 6H).

Example 3

(±)-4-Benzyl-N-isobutyl-N-(2,3,4,5-tetrahydro-1,6-benzodioxocin-8-ylmethyl)morpholine-2-carboxamide

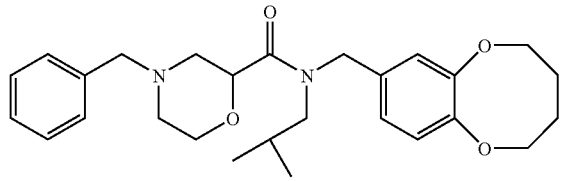

Prepared in the same manner as described for Example 1 from 2,3,4,5-tetrahydro-1,6-benzodioxocine-8-carbaldehyde.

Step 1: 2,3,4,5-tetrahydro-1,6-benzodioxocine-8-carbaldehyde

A mixture of 10 g of 3,5-dihydroxybenzaldehyde, 16 g (0.97 equiv) of 1,4-dibromopropane and 58 g of cesium carbonate in 1 L of anhydrous acetonitrile was heated under nitrogen to 60° C. overnight. The mixture was allowed to cool, then filtered and concentrated under reduced pressure. The residue was partitioned between 500 mL of ethyl acetate and 100 mL of saturated sodium carbonate then dried over magnesium sulfate and concentrated under reduced pressure. Purification by flash chromatography (0-10% methyl tert-butyl ether in hexanes) gave the product as clear oil. MS (m+1)=193.2; 1H NMR (400 MHz, CDCl3) 9.8 (s, 1H), 7.45 (m, 2H), 7.0 (m, 1H), 4.6 (t, 2H), 4.22 (t, 2H), 2.0 (m, 2H), 1.82 (m, 2H).

Example 4

(±)-4-Benzyl-N-isobutyl-N-[(3,3,4,4-tetrafluoro-2,3,4,5-tetrahydro-1,6-benzodioxocin-8-yl)methyl]morpholine-2-carboxamide

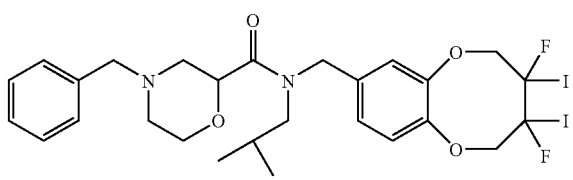

Prepared in the same manner as described for Example 1 from 3,3,4,4-tetrafluoro-2,3,4,5-tetrahydro-1,6-benzodioxocine-8-carbaldehyde.

Step 1: 2,2,3,3-tetrafluorobutane-1,4-diyl bis(trifluoromethanesulfonate)

To an ice cold solution (0° C. internal temp) of 5 g of 2,2,3,3-tetrafluoro-1,4-butanediol and 9 mL of anhydrous pyridine (3.5 equiv) in 100 mL of anhydrous ether was added dropwise 15.4 mL of triflic anhydride (3 equiv) dropwise, keeping the internal temperature below 115° C. After 20 min stirring in the ice bath, the mixture was allowed to warm to room temperature and stirred for 3 h. The mixture was then filtered, concentrated on the rotovap, redissolved in anhydrous ether, refiltered and concentrated again on the rotovap. Drying under vacuum gave an air stable, white crystalline solid: 1H NMR (400 MHz, CDCl3) 4.8 (complex symmetrical multiplet).

Step 2: 3,3,4,4-tetrafluoro-2,3,4,5-tetrahydro-1,6-benzodioxocine-8-carbaldehyde A mixture of 2 g of 3,5-dihydroxybenzaldehyde, 10 g of 2,2,3,3-tetrafluorobutane-1,4-diyl bis(trifluoromethanesulfonate) and 12 g of cesium carbonate in 100 mL of anhydrous acetonitrile was heated under nitrogen to 50° C. overnight. The mixture was allowed to cool, then filtered and concentrated under reduced pressure. The residue was partitioned between 250 mL of ethyl acetate and 100 mL of saturated sodium carbonate then dried over magnesium sulfate and concentrated under reduced pressure. Purification by flash chromatography (0-35% ethyl acetate in hexanes) gave the product as crystalline solid. MS (m+1)=265.1; 1H NMR (400 MHz, CDCl3) 9.85 (s, 1H), 7.6 (m, 2H), 7.2 (d, 1H), 4.64 (t, 2H), 4.45 (t, 2H).

Example 5

(±)-4-Benzyl-N-[(3,3-difluoro-3,4-dihydro-2H-1,5-benzodioxepin-7-yl)methyl]-N-isobutylmorpholine-2-carboxamide

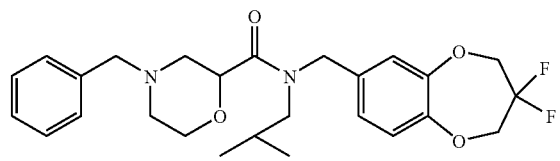

Prepared in the same manner as described for Example 1 from 3,3-difluoro-3,4-dihydro-2H-1,5-benzodioxepine-7-carbaldehyde.

Step 1: 2,2-difluoropropane-1,3-diyl bis(trifluoromethanesulfonate)

To an ice cold solution (0° C. internal temp) of 1.6 g of 2,2-difluoro-1,3-propanediol and 5 mL of anhydrous pyridine in 100 mL of anhydrous ether was added dropwise 7.2 mL of triflic anhydride dropwise, keeping the internal temperature below 15° C. After 20 min stirring in the ice bath, the mixture was allowed to warm to room temperature and stirred for 3 h. The mixture was then filtered, concentrated on the rotovap, redissolved in anhydrous ether, refiltered and concentrated again on the rotovap. Drying under vacuum gave a brown oil.

Step 2: 3,3-difluoro-3,4-dihydro-2H-1,5-benzodioxepine-7-carbaldehyde

A mixture of 2 g of 3,5-dihydroxybenzaldehyde, 6 g of 2,2-difluoropropane-1,3-diyl bis(trifluoromethanesulfonate) and 12 g of cesium carbonate in 100 mL of anhydrous acetonitrile was heated under nitrogen to 50° C. overnight. The mixture was allowed to cool, then filtered and concentrated under reduced pressure. The residue was partitioned between 250 mL of ethyl acetate and 100 mL of saturated sodium carbonate then dried over magnesium sulfate and concentrated under reduced pressure. Purification by flash chromatography (0-25% ethyl acetate in hexanes) gave the product as colorless oil. MS (m+1)=215.1; 1H NMR (400 MHz, CDCl3) 9.85 (s, 1H), 7.6 (m, 2H), 7.1 (d, 1H), 4.48 (m, 4H).

Example 6

(2R)—N-[(3-fluoro-3,4-dihydro-2H-1,5-benzodioxepin-7-yl)methyl]-N-isobutyl-4-(2-methoxybenzyl)morpholine-2-carboxamide

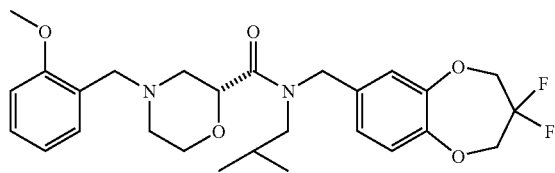

Prepared in the same manner as described for Example 2 from 2,3,4,5-tetrahydro-1,6-benzodioxocine-8-carbaldehyde.

Step 1: 2-fluoropropane-1,3-diyl bis(trifluoromethanesulfonate)

To an ice cold solution (0° C. internal temp) of 1 g of 2-fluoro-1,3-propanediol and 3 mL of anhydrous pyridine in 50 mL of anhydrous ether was added dropwise 5.5 mL of triflic anhydride dropwise, keeping the internal temperature below 15° C. After 20 min stirring in the ice bath, the mixture was allowed to warm to room temperature and stirred for 3 h. The mixture was then filtered, concentrated on the rotovap, redissolved in anhydrous ether, refiltered and concentrated again on the rotovap. Drying under vacuum gave an oil.

Step 2: 3-fluoro-3,4-dihydro-2H-1,5-benzodioxepine-7-carbaldehyde

A mixture of 2 g of 3,5-dihydroxybenzaldehyde, 2.6 g of 2,2-difluoropropane-1,3-diyl bis(trifluoromethanesulfonate) and 10 g of cesium carbonate in 100 mL of anhydrous acetonitrile was heated under nitrogen to 50° C. overnight. The mixture was allowed to cool, then filtered and concentrated under reduced pressure. The residue was partitioned between 250 mL of ethyl acetate and 100 mL of saturated sodium carbonate then dried over magnesium sulfate and concentrated under reduced pressure. Purification by flash chromatography (0-25% ethyl acetate in hexanes) gave the product as white crystalline solid. MS (m+1)=197.1; 1H NMR (400 MHz, CDCl3) 9.82 (s, 1H), 7.45 (m, 2H), 7.05 (d, 1H), 5.1 (doublet of mutliplets, JHF=58 Hz, 1H), 4.5 (m, 4H).

Example 7

(±)-4-benzyl-N-(2,3-dihydro-1-benzofuran-5-ylmethyl)-N-isobutylmorpholine-2-carboxamide

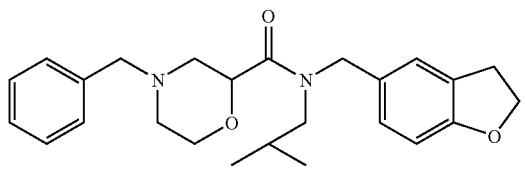

Prepared in the same manner as described for Example 1 from 2,3-dihydro-1-benzofuran-6-carbaldehyde.

Step 1: 2,3-dihydro-1-benzofuran-6-carbaldehyde

To an cooled solution (−78° C. internal temp) of 1 g of 6-bromo-2,3-dihydro-1-benzofuran (prepared as described by Z. J. Song, M. Zhao, L. Frey, J. Li, L. Tan, C. Y. Chen, D. M. Tschaen, R. Tillyer, E. J. J. Grabowski, R. Volante, P. J. Reider, Y. Kato, S. Okada, T. Nemoto, H. Sato, A. Akao, T. Mase, Organic Letters, 2001, Vol. 3, No. 21, 3357-3360) in 20 mL of anhydrous THF was added 4 mL of 2.5 M n-butyllithium in hexane. After stirring 10 min at −78° C., 0.5 mL of anhydrous DMF was added and the mixture allowed to warm to −20° C., quenched with 20 mL of 3N HCl and extracted into 2×50 mL of ether. Combined extracts dried over MgSO4 and concentrated under reduced pressure. Purification by flash chromatography (0-20% ethyl acetate in hexanes) gave the product as white crystalline solid. MS (m+1)=149.1; 1H NMR (400 MHz, CDCl3) 9.9 (s, 1H), 7.4 (m, 2H), 7.3 (s, 1H), 4.62 (t, 2H), 3.28 (t, 4H).

Example 8

(±)-4-benzyl-N-[(5,5-dimethyl-2,3,4,5-tetrahydro-1-benzoxepin-7-yl)methyl]-N-isobutylmorpholine-2-carboxamide

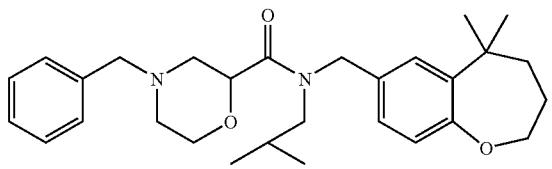

Prepared in the same manner as described for Example 1 from 5,5-dimethyl-2,3,4,5-tetrahydro-1-benzoxepine-7-carbaldehyde.

Step 1: 5,5-dimethyl-2,3,4,5-tetrahydro-1-benzoxepine-7-carbaldehyde

To an cooled solution (0° C. internal temp) of 0.6 g of 5,5-dimethyl-2,3,4,5-tetrahydro-1-benzoxepine (prepared as described by H. Hart, J. L. Corbin, C. R. Wagner, C.-Y., Wu, J. Am. Chem. Soc., 1963, 85, 3269-73) in 10 mL of anhydrous dichloromethane was added 6 mL of 1 M SnCl4 in dichloromethane. After stirring 10 min the ice bath was removed and reaction quenched with 10 mL of water and diluted with 25 mL of dichloromethane. The organic layer was washed with 3×10 mL of water, 3×10 mL of 3N HCl, dried over MgSO$_4$ and concentrated under reduced pressure. Purification by flash chromatography (0-8% methyl tert-butyl ether in hexanes) gave first isomeric 5,5-dimethyl-2,3,4,5-tetrahydro-1-benzoxepine-9-carbaldehyde [$^1$H NMR (400 MHz, CDCl3) 10.45 (s, 1H)], then 0.3 g of 5,5-dimethyl-2,3,4,5-tetrahydro-1-benzoxepine-7-carbaldehyde as an oil. MS (m+1)=205.2; $^1$H NMR (400 MHz, CDCl3) 9.9 (s, 1H), 7.85 (s, 1H), 7.65 (d, 1H), 7.5 (d, 1H), 4.0 (dd, 2H), 2.1 (m, 2H), 1.7 (m, 2H), 1.4 (s, 4H).

Example 9

(−)-(2R)—N-(3,4-dihydro-2H-1,5-benzodioxepin-7-ylmethyl)-N-isobutyl-4-[(3-methoxypyrazin-2-yl)methyl]morpholine-2-carboxamide

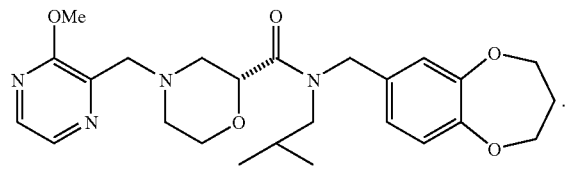

Prepared in the same manner as described for Example 2 using 3-methoxypyrazine-2-carbaldehyde as substitute for 2-methoxybenzaldehyde.

Step 1: methyl 3-methoxypyrazine-2-carboxylate

To a solution of 2 g of methyl 3-bromopyrazine-2-carboxylate (prepared as described by J. H. Jones, W. H. Holtz, E. J. C. Cragoe, J. Med. Chem., 1969, 12, 285-287) in 50 mL of methanol was added 4 mL of 30% NaOMe in methanol. After stirring 30 min the reaction was quenched with 6 mL of acetic acid and concentrated under reduced pressure. The residue was partitioned between 50 mL ethyl acetate and 50 mL saturated NaHCO$_3$, the extract dried over MgSO$_4$. Concentration under reduced pressure gave a white crystalline solid: MS (m+1)=169.1; $^1$H NMR (400 MHz, CDCl3) 8.3 (m, 2H), 4.1 (s, 3H), 4.0 (s, 3H).

Step 2: 3-methoxypyrazine-2-carbaldehyde

To an cooled solution (−78° C. internal temp) of 1 g of methyl 3-methoxypyrazine-2-carboxylate in 50 mL of toluene was added 6 mL of 1 M diisobutyl aluminum hydride in toluene. After stirring 10 min the reaction was quenched with 5 mL of methanol and concentrated under reduced pressure. To a stirred solution of the residue in 100 mL of dichloromethane was added 10 mL of water, then 10 g of MgSO$_4$. The mixture was filtered and 1.5 g of activated MnO$_2$ was added. The mixture was heated to reflux under nitrogen for 5 h, then cooled and filtered. Concentration under reduced pressure gave the product as an odiferous solid: MS (m+1)=139.1; $^1$H NMR (400 MHz, CDCl3) 10.25 (s, 1H), 8.4 (m, 2H), 4.15 (s, 3H).

Example 10

(−)-(2R)—N-(3,4-dihydro-2H-1,5-benzodioxepin-7-ylmethyl)-N-isobutyl-4-[(5-methoxypyridin-3-yl)methyl]morpholine-2-carboxamide

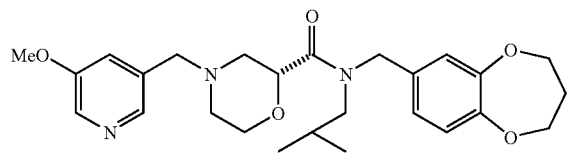

Prepared in the same manner as described for Example 2 using 5-methoxynicotinaldehyde as substitute for 2-methoxybenzaldehyde.

Step 1: methyl 5-hydroxynicotinate

A mixture of 1 g of 5-hydroxynicotinic acid, 2 g Amberlyst 15 ion-exchange resin and 150 mL of methanol was heated to reflux with stirring for 24 hrs, cooled, basified with 10% ammonia in methanol, filtered and concentrated under reduced pressure. The residue was taken up in 50 mL of chloroform and dried over MgSO$_4$. Concentration under reduced pressure gave a tan crystalline solid: MS (m+1)= 154.1; $^1$H NMR (400 MHz, CDCl3) 8.68 (s, 1H), 8.32 (s, 1H), 7.72 (s, 1H), 3.94 (s, 3H).

Step 2: methyl 5-methoxynicotinate

A mixture of 0.5 g of methyl 5-hydroxynicotinate, 1.2 g (2 equiv) of phenyltrimethylammonium chloride, 4.8 g (3 equiv) of cesium carbonate, and 5 mL of anhydrous acetonitrile was heated to 80° C. for 6 h, cooled, filtered and concentrated under reduced pressure. The residue was taken up in 25 mL of ethyl acetate, filtered and concentrated. Purification by flash chromatography (0-50% ethyl acetate in hexane) gave the product as white crystalline solid: MS (m+1)=168.1; $^1$H NMR (400 MHz, CDCl3) 8.72 (s, 1H), 8.4 (s, 1H), 7.67 (s, 1H), 3.83 (s, 3H), 3.82 (s, 3H).

Step 3: 5-methoxynicotinaldehyde

To an cooled solution (−78° C. internal temp) of 0.2 g of methyl 3-methoxypyrazine-2-carboxylate in 25 mL of toluene was added 3 mL of 1 M diisobutyl aluminum hydride in toluene. After stirring 10 min the reaction was quenched with 5 mL of water, allowed to warm to room temperature and dried with 5 g of MgSO$_4$. Concentration under reduced pressure gave 0.2 g of (5-methoxypyridin-3-yl)methanol as an resin (MS (m+1)=140.1). The (5-methoxypyridin-3-yl)methanol (0.2 g) was taken up 10 mL of anhydrous acetonitrile and added to a stirred mixture of 0.5 g of periodic acid and 0.05 g of chromium (III) acetylacetonate in 10 mL of acetonitrile. After stirring for 5 hrs at room temperature, the mixture was concentrated on the rotovap and partitioned between 20 mL of saturated sodium carbonate and 3×50 mL of ethyl acetate. The combined extracts were dried over MgSO$_4$ and concentrated under reduced pressure. The product was obtained as an orange-brown oil and was used without further purification: MS (m+1)=138.1.

Example 11

(−)-(2R)—N-(3,4-dihydro-2H-1,5-benzodioxepin-7-ylmethyl)-N-isobutyl-4-[(2-methoxy-6-methylpyrimidin-4-yl)methyl]morpholine-2-carboxamide

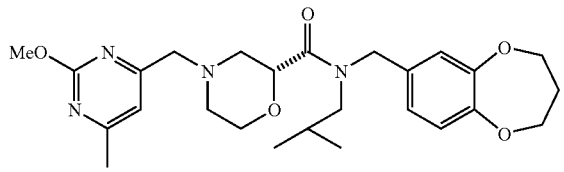

Prepared in the same manner as described for Example 2 using 2-methoxy-6-methylpyrimidine-4-carbaldehyde as substitute for 2-methoxybenzaldehyde.

Step 1: methyl 2-methoxy-6-methylpyrimidine-4-carboxylate

A mixture of 1 g of methyl 2-chloro-6-methylpyrimidine-4-carboxylate, 20 mL of methanol and 2 mL of 30% sodium methoxide in methanol was stirred under nitrogen at room temperature for 3 hrs, quenched with 3 mL of acetic acid and concentrated under reduced pressure. The residue was partitioned between 25 mL of saturated sodium bicarbonate and 3×20 mL of ethyl acetate and the extracts dried over $MgSO_4$. Concentration under reduced pressure gave a white crystalline solid: MS (m+1)=183.1; $^1$H NMR (400 MHz, CDCl3) 7.5 (s, 1H), 4.1 (s, 3H), 4.0 (s, 3H), 2.58 (s, 3H).

Step 2: 2-methoxy-6-methylpyrimidine-4-carbaldehyde

To an cooled solution (−78° C. internal temp) of 0.5 g of methyl 2-methoxy-6-methylpyrimidine-4-carboxylate in 15 mL of toluene and 15 mL of dichloromethane was added 6 mL of 1 M diisobutyl aluminum hydride in toluene. After stirring 10 min the reaction was quenched with 5 mL of water, allowed to warm to room temperature and dried with 5 g of $MgSO_4$. Concentration of the filtrate under reduced pressure gave the product as an resin and was used without further purification: MS (m+1)=153.1 and 171.1 (hydrate).

Example 12

(−)-(2R)—N-(3,4-dihydro-2H-1,5-benzodioxepin-7-ylmethyl)-N-isobutyl-4-[(3-methoxypyridin-4-yl)methyl]morpholine-2-carboxamide

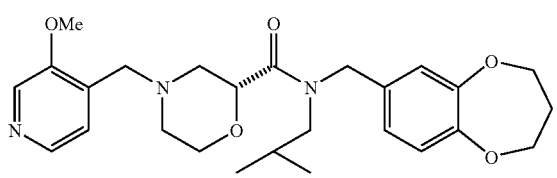

Prepared in the same manner as described for Example 2 using 3-methoxyisonicotinaldehyde as substitute for 2-methoxybenzaldehyde.

Step 1: 3-methoxyisonicotinaldehyde

To an cooled solution (−78° C. internal temp) of 0.192 g of methyl 3-methoxyisonicotinate in 10 mL of toluene was added 2 mL of 1 M diisobutyl aluminum hydride in toluene. After stirring 10 min the reaction was quenched with 5 mL of methanol and concentrated under reduced pressure. To a stirred solution of the residue (0.15 g) in 50 mL of dichloromethane was added 1 mL of water, then 1 g of $MgSO_4$. The mixture was filtered and 0.75 g of activated $MnO_2$ was added. The mixture was heated to reflux under nitrogen for 5 h, then cooled and filtered. Concentration under reduced pressure gave a resin: MS (m+1)=138.1.

Example 13

(−)-(2R)—N-(3,4-dihydro-2H-1,5-benzodioxepin-7-ylmethyl)-N-isobutyl-4-[(4-methoxypyrimidin-5-yl)methyl]morpholine-2-carboxamide

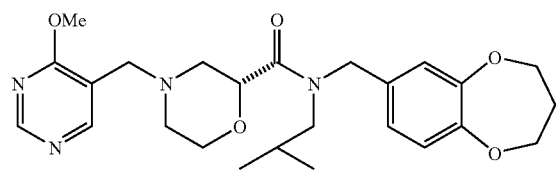

Prepared in the same manner as described for Example 2 using 4-methoxypyrimidine-5-carbaldehyde as substitute for 2-methoxybenzaldehyde.

Step 1: methyl 4-methoxy-2-(methylthio)pyrimidine-5-carboxylate

A mixture of 5 g of ethyl 4-chloro-2-(methylthio)pyrimidine-5-carboxylate, 250 mL of methanol and 5 mL of 30% sodium methoxide in methanol was stirred under nitrogen at room temperature for 5 hrs, quenched with 10 mL of acetic acid and concentrated under reduced pressure. The residue was partitioned between 100 mL of saturated sodium bicarbonate and 200 mL of ethyl acetate and the extracts dried over $MgSO_4$. Concentration under reduced pressure gave a white crystalline solid: MS (m+1)=215.1; $^1$H NMR (400 MHz, CDCl3) 8.85 (s, 1H), 4.1 (s, 3H), 4.05 (s, 3H), 3.85 (s, 3H).

Step 2: methyl 4-methoxypyrimidine-5-carboxylate

A mixture of 2.2 g of methyl 4-methoxy-2-(methylthio)pyrimidine-5-carboxylate, 15 g of Raney nickel (washed with methanol to remove water) and 200 mL of methanol was stirred under 1 atm hydrogen overnight. Conversion was incomplete by LCMS so the mixture was filtered and treated with 15 g of fresh Raney nickel under hydrogen overnight. After filtration and concentration under reduced pressure, purification by flash chromatography (0%-10% ethyl acetate in hexanes) gave the product as white crystalline solid: MS (m+1)=169.1; ¹H NMR (400 MHz, CDCl3) 9.0 (s, 1H), 8.82 (s, 1H), 4.1 (s, 3H), 3.9 (s, 3H).

Step 3: 4-methoxypyrimidine-5-carbaldehyde

To an cooled solution (−78° C. internal temp) of 0.3 g of methyl 4-methoxypyrimidine-5-carboxylate in 20 mL of dichloromethane was added 2 mL of 1 M diisobutyl aluminum hydride in toluene. After stirring 10 min the reaction was quenched with 5 mL of water, allowed to warm to room temperature and dried with 5 g of MgSO$_4$. Concentration of the filtrate under reduced pressure gave the product as a resin and was used without further purification: MS (m+1)=171.1 (hydrate).

Example 14

(−)-(2R)—N-(2,3-dihydro-1,4-benzodioxin-6-ylmethyl)-N-isobutyl-4-(2-methoxybenzyl)morpholine-2-carboxamide

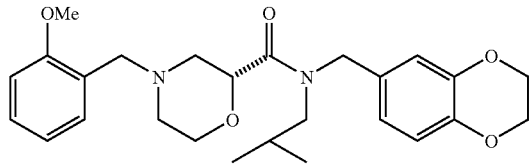

Prepared in the same manner as described for Example 2 from commercially available 1,4-Benzodixan-6-carboxaldehyde. [α]$_D^{23°\,C}$=5.0° (c=1.0, MeOH); MS (m+1)=455.3; H NMR (500 MHz, CDCl3) 7.34-7.21 (m, 2H), 6.93-6.85 (m, 2H), 6.80 (m, 1H), 6.72-6.63 (m, 2H) 4.63 (t, 1H), 4.41-4.21 (m, 6H), 3.92 (m, 1H), 3.81 (d, 3H), 3.72-3.60 (m, 3H), 3.31-3.15 (m, 1H), 3.00-2.90 (m, 2H), 2.70 (t, 1H), 2.53 (t, 1H) 2.39-2.28 (m, 1H), 1.97 (m, 1H), 0.87 (m, 6H).

Example 15

(±)-N-Isobutyl-4-(2-methoxybenzyl)-N-(2,3,4,5-tetrahydro-1-benzoxepin-8-ylmethyl)morpholine-2-carboxamide

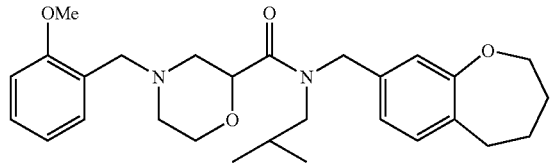

Step 1: 4-(2,5-Dibromophenoxy)butan-1-ol

To a stirred mixture of 25 g (99 mmol) of 2,4-dibromo-1-fluorobenzene, 127 mL of 1,4-butanediol, and 12.7 mL of 1-methyl-2-pyrrolidinone under nitrogen at ambient temperature was added 38.9 g (347 mmol, 3.5 equiv) of potassium tert-butoxide in portions over five minutes. The resulting dark mixture was stirred at 100° C. overnight. The mixture was cooled to ambient temperature and 50 mL of water was added over 30 minutes. The mixture was filtered and insoluble solids were washed with 2×6 mL of 1,3-propanediol. To the combined filtrate was added over 30 minutes 440 mL of water. The mixture was cooled in an ice-bath for 1.5 hours. An orange oil separated, and the supernatant was decanted. The oil was dissolved in 100 mL of ether, washed with 3×20 mL of water, dried over sodium sulfate, filtered, and concentrated under reduced pressure to give the product as an orange oil. MS (m+1)=325.0; 1H NMR (400 MHz, CDCl3) 7.38 (d, 1H, J 8 Hz), 7.01 (d, 1H, J 2 Hz), 6.96 (m, 1H), 4.06 (t, 2H, J 6 Hz), 3.76 (t, 2H, J 6 Hz), 1.96 (m, 2H), 1.80 (m, 2H), 1.52 (s, 1H). Extraction of the aqueous layers with 3×10 mL of ether gave additional as a yellow oil.

Step 2: 1,4-Dibromo-2-(4-bromobutoxy)benzene

To a solution of 12.63 g (39 mmol) of 4-(2,5-dibromophenoxy)butan-1-ol in 83 mL of toluene was added 1.65 mL (17.6 mmol, 0.45 equiv) of phosphorous tribromide. The solution was stirred under nitrogen at 90° C. for 2.5 hours. Additional phosphorous tribromide (0.37 mL, 3.9 mmol, 0.10 equiv) and 0.21 ml (11.5 mmol, 0.3 equiv) of water were added, and the mixture was stirred under nitrogen at 90° C. for 8 hours. The mixture was allowed to cool to ambient temperature, 69 mL of 1N NaOH was added dropwise over 30 minutes, and the layers were separated. The aqueous layer was extracted with 25 mL of toluene. The combined organic layer was washed with 25 mL each of water and brine, dried over sodium sulfate, filtered, and concentrated under reduced pressure to give the product as a cloudy yellow oil suitable for the next step. MS (m+1)=386.1, 385.1, 381.0; 1H NMR (400 MHz, CDCl3) 7.38 (d, 1H, J 8 Hz), 6.98 (m, 2H), 4.05 (t, 2H, J 6 Hz), 3.53 (t, 2H, J 6 Hz), 2.12 (m, 2H), 2.03 (m, 2H).

Step 3: 8-Bromo-2,3,4,5-tetrahydro-1-benzoxepine

To a solution of 12.7 g (33 mmol) of 1,4-dibromo-2-(4-bromobutoxy)benzene in 220 mL of anhydrous tetrahydrofuran and 55 mL of hexane under nitrogen cooled in a dry ice/acetone bath was added dropwise 14.5 mL (36.3 mmol, 1.1 equiv) of 2.5M n-butyllithium in tetrahydrofuran, keeping the internal temperature <−70° C. The mixture was stirred with cooling for 30 minutes, then at ambient temperature. After 5 hours, 220 mL of water was added and the layers were separated. The aqueous layer was extracted with 2×160 mL of ether. The combined organic layer was dried over sodium sulfate, filtered, and concentrated under reduced pressure to give 7.7 g of a yellow oil. Purification by flash chromatography (5-20% ethyl acetate in hexanes) gave the product as a yellow oil. MS (m+1)=228.1; 1H NMR (400 MHz, CDCl3) 7.15 (d, 1H, J 2 Hz), 7.09 (m, 1H), 6.99 (d, 1H, J 8 Hz), 4.01 (m, 2H), 2.76 (m, 2H), 1.96 (m, 2H), 1.71 (m, 2H).

Step 4: 2,3,4,5-Tetrahydro-1-benzoxepine-8-carbaldehyde

To a solution of 2.01 g (8.8 mmol) of 8-bromo-2,3,4,5-tetrahydro-1-benzoxepine in 54 mL of anhydrous tetrahydrofuran and 13.5 mL of hexane under nitrogen cooled in a dry ice/acetone bath was added dropwise 4.1 mL (10.2 mmol, 1.15 equiv) of 2.5M n-butyllithium in tetrahydrofuran, keeping the internal temperature <−65° C. The mixture was stirred with cooling for 45 minutes. A solution of 1.03 mL (13.3 mmol, 1.5 equiv) dimethylformamide in 9 mL of anhydrous tetrahydrofuran was added dropwise over 5 minutes. The mixture was stirred overnight while warming to ambient temperature. The reaction mixture was poured into 81 mL of 2N HCl, and the layers were separated. The aqueous layer was extracted with 3×85 mL of ether. The combined organic layer was washed with 75 mL each of water and brine, dried over sodium sulfate, filtered, and concentrated under reduced pressure to give 1.64 g of a yellow oil. Purification by flash chromatography (5-40% ethyl acetate in hexanes) gave the product as a colorless oil. MS (m+1)=177.2; 1H NMR (400 MHz, CDCl3) 9.92 (s, 1H), 7.49 (m, 2H), 7.29 (d, 1H, J 7.5 Hz), 4.03 (m, 2H), 2.89 (m, 2H), 2.00 (m, 2H), 1.76 (m, 2H).

Step 5: 2-Methyl-N-(2,3,4,5-tetrahydro-1-benzoxepin-8-ylmethyl)propan-1-amine

To a mixture of 0.48 g (2.7 mmol) of 2,3,4,5-tetrahydro-1-benzoxepine-8-carbaldehyde and 1.33 mL (13.5 mmol, 5 equiv) of isobutylamine in 22 mL of 1,2-dichloroethane was added 0.86 mL (15.0 mmol, 5.5 equiv) of acetic acid. The mixture was stirred under nitrogen at ambient temperature for 20 minutes and 0.64 g (3.0 mmol, 1.1 equiv) of sodium triacetoxyborohydride was added. The mixture was stirred overnight then diluted with 125 mL of ethyl acetate and washed with 60 mL each of saturated sodium bicarbonate solution, water and brine, dried over sodium sulfate, filtered, and concentrated under reduced pressure to give 0.67 g of a yellow oil. Purification by flash chromatography (0-10% methanol in ethyl acetate) gave the product as a colorless oil. MS (m+1)=234.2; 1H NMR (400 MHz, CDCl3) 7.07 (d, 1H, J 8 Hz), 7.09 (d, 1H, J 1.5 Hz), 6.99 (m, 1H), 3.99 (m, 2H), 3.72 (s, 2H), 2.70 (m, 2H), 2.43 (d, 2H, J 7 Hz), 1.95 (m, 2H), 1.77 (m, 1H), 1.71 (m, 2H), 1.5 (br s, 1H), 0.91 (d, 6H, J 7 Hz).

Step 6: (±)-tert-Butyl 2-{[isobutyl(2,3,4,5-tetrahydro-1-benzoxepin-8-ylmethyl)amino]carbonyl}-morpholine-4-carboxylate A mixture of 0.51 g (2.2 mmol) of 2-methyl-N-(2,3,4,5-tetrahydro-1-benzoxepin-8-ylmethyl)propan-1-amine, 0.51 g (2.2 mmol) of (±)-4-(tert-butoxycarbonyl)morpholine-2-carboxylic acid (Chem-Impex International), 0.59 g (4.4 mmol) of 1-hydroxybenzotriazole hydrate, 0.84 g (4.4 mmol) of 1-ethyl-3-(3-dimethylaminopropyl)carbodiimide hydrochloride and 0.71 mL (5.1 mmol) of triethylamine in 15 mL in dichloromethane was stirred overnight. The mixture was concentrated under reduced pressure, partitioned between 90 mL of ethyl acetate and 30 mL of saturated sodium bicarbonate, and the layers were separated. The organic layer was washed with 30 mL each of water and brine, dried over sodium sulfate, filtered, and concentrated under reduced pressure to give a yellow oil. Purification by flash chromatography (10-70% ethyl acetate in hexanes) gave 0.84 g (86%) of product as a solid white foam. MS (m+1)=447.4; H NMR (400 MHz, CDCl3) 7.09 (m, 1H), 6.8 (m, 2H), 4.7 (m, 1H), 4.44 (d, 1H, J 17 Hz), 4.2-3.8 (m, 6H), 3.50 (m, 1H), 3.21 (m, 2H), 3.02 (m, 2H), 2.79 (m, 2H), 1.96 (m, 3H), 1.72 (m, 2H), 1.45 (d, 9H, J 13 Hz), 0.85 (m, 6H).

Step 7: (±)-N-isobutyl-N-(2,3,4,5-tetrahydro-1-benzoxepin-8-ylmethyl)morpholine-2-carboxamide hydrochloride To a solution of 0.798 g (1.79 mmol) of (±)-tert-butyl 2-{[isobutyl(2,3,4,5-tetrahydro-1-benzoxepin-8-ylmethyl) amino]carbonyl}morpholine-4-carboxylate in 3.6 mL of dioxane cooled in an ice-bath was added 3.6 mL (14.4 mmol, 8 equiv) of 4M HCl in dioxane. The solution was stirred 30 minutes with cooling, then for 3.5 hours at ambient temperature. The solution was concentrated under reduced pressure, the residue triturated with ether, and dried under vacuum to give the product as a white solid. MS (m+1)=347.3; H NMR (400 MHz, CD3OD) 7.12 (m, 1H), 6.84 (m, 2H), 4.8-4.6 (m, 2H), 4.58-4.39 (m, 1H), 4.1-3.85 (m, 4H), 3.5-3.35 (m, 3H), 3.24 (m, 2H), 3.15-2.92 (m, 1H), 2.78 (m, 2H), 2.02 (m, 1H), 1.95 (m, 2H), 1.71 (m, 2H), 0.89 (m, 6H).

Step 8: (±)-N-Isobutyl-4-(2-methoxybenzyl)-N-(2,3,4,5-tetrahydro-1-benzoxepin-8-ylmethyl)morpholine-2-carboxamide hydrochloride A mixture of 31 mg (0.080 mmol) of (±)-N-isobutyl-N-(2,3,4,5-tetrahydro-1-benzoxepin-8-ylmethyl)morpholine-2-carboxamide hydrochloride, 0.0106 mL (0.088 mmol) of o-anisaldehyde, and 6.6 mg (0.080 mmol) of sodium acetate in 0.5 mL of 1,2-dichloroethane was stirred under nitrogen at ambient temperature for 10 minutes and 19 mg (0.088 mmol) of sodium triacetoxyborohydride was added. The mixture was stirred overnight then diluted with 5 mL of ethyl acetate and washed with 2 mL each of saturated sodium bicarbonate solution, water and brine, dried over sodium sulfate, filtered, and concentrated under reduced pressure to give 41 mg of a colorless gum. Preparative TLC (60% ethyl acetate/hexanes) gave 25 mg (68%) of product free-base as a gum. The gum was taken up in 1 mL of methanol, treated with 5 drops of 4M HCl in dioxane, and the mixture was concentrated. The residue was triturated with ether, and dried under vacuum to give the hydrochloride salt as a solid white foam. MS (m+1)= 467.3; H NMR (400 MHz, CD3OD) 7.45 (m, 2H), 7.10 (m, 3H), 6.85 (m, 2H), 4.97 (m, 1H), 4.81 (m, 1H), 4.56-4.39 (m, 3H), 4.1-3.7 (m, 8H), 3.6-3.2 (m, 3H), 3.2-2.85 (m, 2H), 2.77 (d, 2H, J 6 Hz), 2.04 (m, 1H), 1.94 (m, 2H), 1.70 (m, 2H), 0.90 (m, 6H).

Example 16

(±)-4-Benzyl-N-isobutyl-N-(2,3,4,5-tetrahydro-1-benzoxepin-8-ylmethyl)morpholine-2-carboxamide

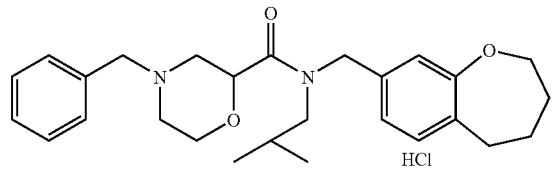

Employing the procedure as described for Example 15, Step 8, but substituting benzaldehyde for o-anisaldehyde, product was obtained as the hydrochloride salt. MS (m+1)= 437.3; H NMR (400 MHz, CD3OD) 7.53 (m, 5H), 7.10 (m, 1H), 6.82 (m, 2H), 4.96 (m, 1H), 4.75 (m, 1H), 4.58-4.3 (m, 3H), 4.18 (m, 2H), 3.94 (m, 3H), 3.57-3.20 (m, 3H), 3.18-2.90 (m, 2H), 2.77 (d, 2H, J 10 Hz), 2.02 (m, 1H), 1.94 (m, 2H), 1.69 (m, 2H), 0.87 (m, 6H).

Example 17

(±)-N-Isobutyl-4-(2-methoxybenzyl)-N-(2,3,4,5-tetrahydro-1-benzoxepin-7-ylmethyl)morpholine-2-carboxamide

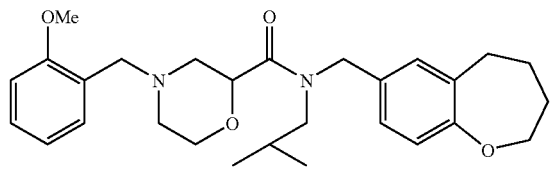

Step 1: 2,4-dibromo-1-(4-bromobutoxy)benzene

A mixture of 5 g of 2,4-didibromophenol, 21.5 g (5 equiv) of 1,4-dibromobutane and 8 g (1.2 equiv) of cesium carbonate in 50 mL of anhydrous acetonitrile was heated under nitrogen to 50° C. overnight. The mixture was allowed to cool, then filtered and concentrated under reduced pressure. The residue was partitioned between 100 mL of ether and 100 mL of saturated sodium carbonate then dried over magnesium sulfate and concentrated under reduced pressure. Purification by flash chromatography (0-10% ethyl acetate in hexanes) gave the product as crystalline solid. $^1$H NMR (400 MHz, CDCl3) 7.65 (d, 1H), 7.38 (dd, 1H), 6.88 (d, 1H), 4.05 (m, 2H), 3.5 (m, 2H), 2.5 (m, 2H), 2.0 (m, 2H).

Step 2: 7-Bromo-2,3,4,5-tetrahydro-1-benzoxepine

Employing the procedure as described for Example 15, Step 3, but substituting 2,4-dibromo-1-(4-bromobutoxy)benzene for 1,4-dibromo-2-(4-bromobutoxy)benzene, product was obtained as a colorless oil. MS (m+1)=229.1; 1H NMR (400 MHz, CDCl3) 7.22 (m, 1H), 6.85 (d, 1H, J 8 Hz), 6.77 (d, 1H, J 9 Hz), 3.96 (m, 2H), 2.75 (m, 2H), 1.95 (m, 2H), 1.71 (m, 2H).

Step 3: 2,3,4,5-Tetrahydro-1-benzoxepine-7-carbaldehyde

Employing the procedure as described for Example 15, Step 4, but substituting 7-bromo-2,3,4,5-tetrahydro-1-benzoxepine for 8-bromo-2,3,4,5-tetrahydro-1-benzoxepine, product was obtained as a colorless oil. MS (m+1)=177.1; 1H NMR (400 MHz, CDCl3) 9.90 (s, 1H), 7.67 (m, 2H), 7.09 (d, 1H, J 8 Hz), 4.09 (t, 2H, J 5 Hz), 2.90 (m, 2H), 2.00 (m, 2H), 1.78 (m, 2H).

Step 4: 2-Methyl-N-(2,3,4,5-tetrahydro-1-benzoxepin-7-ylmethyl)propan-1-amine Employing the procedure as described for Example 15, Step 5, but substituting 2,3,4,5-tetrahydro-1-benzoxepine-7-carbaldehyde for 2,3,4,5-tetrahydro-1-benzoxepine-8-carbaldehyde, product was obtained as a colorless oil. MS (m+1)= 234.2; 1H NMR (400 MHz, CDCl3) 7.09 (d, 1H, J 2 Hz), 7.07 (m, 1H), 6.93 (d, 1H, J 8 Hz), 3.98 (t, 2H, J 5 Hz), 3.70 (s, 2H), 2.80 (m, 2H), 2.45 (d, 2H, J 7 Hz), 1.95 (m, 2H), 1.78 (m, 1H), 1.71 (m, 2H), 1.5 (br s, 1H), 0.91 (d, 6H, J 7 Hz).

Step 5: (±)-tert-Butyl 2-{[isobutyl(2,3,4,5-tetrahydro-1-benzoxepin-7-ylmethyl)amino]carbonyl}morpholine-4-carboxylate Employing the procedure as described for Example 15, Step 6, but substituting 2-methyl-N-(2,3,4,5-tetrahydro-1-benzoxepin-7-ylmethyl)propan-1-amine for 2-methyl-N-(2,3,4,5-tetrahydro-1-benzoxepin-8-ylmethyl)propan-1-amine, product was obtained as a solid white foam. MS (m+1)= 447.3; 1H NMR (400 MHz, CDCl3) 6.93 (m, 3H), 4.6 (m, 1H), 4.46 (d, 1H, J 17 Hz), 4.2-3.8 (m, 6H), 3.51 (m, 1H), 3.23 (m, 2H), 3.02 (m, 2H), 2.78 (m, 2H), 1.97 (m, 3H), 1.72 (m, 2H), 1.46 (d, 9H, J 13 Hz), 0.90 (m, 6H).

Step 6: (±)-N-isobutyl-N-(2,3,4,5-tetrahydro-1-benzoxepin-7-ylmethyl)morpholine-2-carboxamide hydrochloride Employing the procedure as described for Example 15, Step 7, but substituting (±)-tert-butyl 2-{[isobutyl(2,3,4,5-tetrahydro-1-benzoxepin-7-ylmethyl)amino]carbonyl}morpholine-4-carboxylate for (±)-tert-butyl 2-{[isobutyl(2,3,4,5-tetrahydro-1-benzoxepin-8-ylmethyl)amino]carbonyl}morpholine-4-carboxylate, product was obtained as a solid white foam. MS (m+1)=347.3; 1H NMR (400 MHz, CD3OD) 7.00 (m, 2H), 6.96 (m, 1H), 4.78-4.65 (m, 2H), 4.57-4.38 (m, 1H), 4.09-3.85 (m, 4H), 3.51-3.35 (m, 3H), 3.26 (m, 2H), 3.14-2.92 (m, 1H), 2.78 (m, 2H), 2.03 (m, 1H), 1.95 (m, 2H), 1.70 (m, 2H), 0.90 (m, 6H).

Step 7: (±)-N-Isobutyl-4-(2-methoxybenzyl)-N-(2,3,4,5-tetrahydro-1-benzoxepin-7-ylmethyl)morpholine-2-carboxamide hydrochloride Employing the procedure as described for Example 15, Step 8, but substituting (±)-N-isobutyl-N-(2,3,4,5-tetrahydro-1-benzoxepin-7-ylmethyl)morpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)=467.3; H NMR (400 MHz, CD3OD) 7.51 (m, 1H), 7.41 (d, 2H, J 7 Hz), 7.15 (m, 1H), 7.03 (m, 2H), 6.93 (m, 2H), 5.01 (m, 1H), 4.71 (m, 1H), 4.55-4.36 (m, 3H), 4.2-3.75 (m, 8H), 3.6-3.25 (m, 4H), 3.18-2.90 (m, 1H), 2.77 (m, 2H), 2.05 (m, 1H), 1.94 (m, 2H), 1.69 (m, 2H), 0.90 (m, 6H).

Example 18

(±)-4-Benzyl-N-isobutyl-N-(2,3,4,5-tetrahydro-1-benzoxepin-8-ylmethyl)morpholine-2-carboxamide

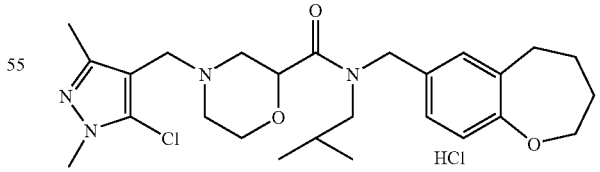

Employing the procedure as described for Example 17, Step 8, but substituting 5-chloro-1,3-dimethyl-1H-pyrazole-4-carbaldehyde for o-anisaldehyde, product was obtained as the hydrochloride salt. MS (m+1)=490.3; H NMR (400 MHz, CD3OD) 7.07-6.87 (m, 3H), 5.03 (m, 0.5H), 4.72 (m, 1H), 4.51 (m, 1.5H), 4.32 (m, 2H), 4.00 (d, 1H, J 14 Hz), 4.12-3.90 (m, 3H), 3.83 (s, 3H), 3.71-3.58 (m, 1H), 3.53-3.54 (m, 3H), 3.30 (m, 1H, obscured by CH3OD peak), 3.15-2.87 (m, 1H), 2.77 (m, 2H), 2.33 (d, 3H, J 9 Hz), 2.05 (m, 1H), 1.94 (m, 2H), 1.70 (m, 2H), 0.89 (m, 6H).

Example 19

(±)-N-(3,4-Dihydro-2H-chromen-7-ylmethyl)-N-isobutyl-4-(2-methoxybenzyl)morpholine-2-carboxamide

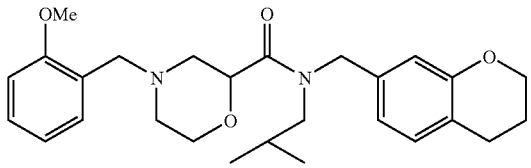

Step 1: 3-(2,5-Dibromophenoxy)propan-1-ol

Employing the procedure as described for Example 15, Step 1, but substituting 1,3-propanediol for 1,4-butanediol, product was obtained as a solid.

Step 2: 1,4-Dibromo-2-(3-bromopropoxy)benzene

Employing the procedure as described for Example 15, Step 2, but substituting 3-(2,5-dibromophenoxy)propan-1-ol for 4-(2,5-dibromophenoxy)butan-1-ol, product was obtained as an oil.

Step 3: 7-Bromochromane

Employing the procedure substantially as described for Example 15, Step 3, but substituting 1,4-dibromo-2-(3-bromopropoxy)benzene for 1,4-dibromo-2-(4-bromobutoxy)benzene, product was obtained as a pale yellow oil. MS (m+1)=214; 1H NMR (400 MHz, CDCl3) 6.93 (m, 2H), 6.88 (m, 1H), 4.16 (t, 2H, J 5 Hz), 2.72 (t, 2H, J 6 Hz), 1.99 (m, 2H).

Step 4: Chromane-7-carbaldehyde

Employing the procedure as described for Example 15, Step 4, but substituting 7-bromochromane for 8-bromo-2,3,4,5-tetrahydro-1-benzoxepine, product was obtained as a pale yellow oil. MS (m+1)=163.2; 1H NMR (400 MHz, CDCl3) 9.90 (s, 1H), 7.35 (m, 1H), 7.28 (d, 1H, J 2 Hz), 7.18 (m, 1H), 4.23 (t, 2H, J 5 Hz), 2.86 (t, 2H, J 6 Hz), 2.04 (m, 2H).

Step 5

N-(3,4-dihydro-2H-chromen-7-ylmethyl)-2-methylpropan-1-amine

Employing the procedure as described for Example 15, Step 5, but substituting chromane-7-carbaldehyde for 2,3,4,5-tetrahydro-1-benzoxepine-8-carbaldehyde, product was obtained as a colorless oil. MS (m+1)=220.3; 1H NMR (400 MHz, CDCl3) 6.98 (d, 1H, J 8 Hz), 6.78 (m, 1H), 6.75 (s, 1H), 4.17 (t, 2H, J 5 Hz), 3.70 (s, 2H), 2.77 (d, 2H, J 6 Hz), 2.42 (d, 2H, J 7 Hz), 1.99 (m, 2H), 1.76 (m, 1H), 1.42 (br s, 1H), 0.90 (d, 6H, J 7 Hz).

Step 6: (±)-tert-Butyl 2-{[(3,4-dihydro-2H-chromen-7-ylmethyl)(isobutyl)amino]carbonyl}morpholine-4-carboxylate Employing the procedure as described for Example 15, Step 6, but substituting N-(3,4-dihydro-2H-chromen-7-ylmethyl)-2-methylpropan-1-amine for 2-methyl-N-(2,3,4,5-tetrahydro-1-benzoxepin-8-ylmethyl)propan-1-amine, product was obtained as a solid white foam. MS (m+1)=433.3; H NMR (400 MHz, CDCl3) 7.00 (m, 1H), 6.63 (m, 2H), 4.7 (m, 1H), 4.42 (d, 1H, J 18 Hz), 4.19-3.72 (m, 6H), 3.49 (m, 1H), 3.21 (m, 2H), 3.01 (m, 2H), 2.77 (m, 2H), 1.99 (m, 3H), 1.46 (d, 9H, J 13 Hz), 0.88 (m, 6H).

Step 7: (±)-N-(3,4-dihydro-2H-chromen-7-ylmethyl)-N-isobutylmorpholine-2-carboxamide hydrochloride Employing the procedure as described for Example 15, Step 7, but substituting (±)-tert-butyl 2-{[(3,4-dihydro-2H-chromen-7-ylmethyl)(isobutyl)amino]carbonyl}morpholine-4-carboxylate for (±)-tert-butyl 2-{[isobutyl(2,3,4,5-tetrahydro-1-benzoxepin-8-ylmethyl)amino]carbonyl}morpholine-4-carboxylate, product was obtained as a white solid. MS (m+1)=333.3; H NMR (400 MHz, CD3OD) 7.01 (m, 1H), 6.70 (t, 1H, J 8 Hz), 6.61 (t, 1H, J 10 Hz), 4.80-4.61 (m, 2H), 4.54-4.35 (m, 1H), 4.14 (m, 2H), 4.04 (m, 1H), 3.89 (m, 1H), 3.51-3.34 (m, 3H), 3.25 (m, 2H), 3.13-2.92 (m, 1H), 2.77 (m, 2H), 2.00 (m, 3H), 0.90 (m, 6H).

Step 8

(±)-N-(3,4-Dihydro-2H-chromen-7-ylmethyl)-N-isobutyl-4-(2-methoxybenzyl)morpholine-2-carboxamide hydrochloride Employing the procedure as described for Example 15, Step 8, but substituting (±)-N-(3,4-dihydro-2H-chromen-7-ylmethyl)-N-isobutylmorpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)= 453.3; H NMR (400 MHz, CD3OD) 7.50 (m, 1H), 7.39 (m, 1H), 7.14 (m, 1H), 7.04 (m, 2H), 6.69 (m, 2H), 4.98 (m, 1H), 4.79 (m, 1H), 4.59 (m, 1H), 4.39 (s, 2H), 4.14 (t, 2H, J 5 Hz), 3.89-3.70 (m, 5H), 3.42 (m, 3H), 3.3-2.9 (m, 3H, obscured by CH3OD peak), 2.00 (m, 3), 1.94 (m, 2H), 0.89 (m, 6H).

Step 9: (S)-(+)-N-(3,4-dihydro-2H-chromen-7-ylmethyl)-N-isobutyl-4-(2-methoxybenzyl)morpholine-2-carboxamide and (R)-(−)—N-(3,4-dihydro-2H-chromen-7-ylmethyl)-N-isobutyl-4-(2-methoxybenzyl)morpholine-2-carboxamide Resolution into the pure enantiomers was performed by preparative HPLC using isocratic elution on ChiralPak AD at 80 mL/min, eluting with 20% isopropanol, and 80% hexanes with 1 mL/L diethylamine as modifier. Under these conditions, the (R)-(−)-isomer elutes first. (R)-(−)—N-(3,4-dihydro-2H-chromen-7-ylmethyl)-N-isobutyl-4-(2-methoxybenzyl)morpholine-2-carboxamide: $[\alpha]_D^{25°\,C}=-36°$ (c=0.25, MeOH). (S)-(+)-N-(3,4-dihydro-2H-chromen-7-ylmethyl)-N-isobutyl-4-(2-methoxybenzyl)morpholine-2-carboxamide: $[\alpha]_D^{25°\,C}=+36°$ (c=0.26, MeOH)

Example 20

(±)-4-Benzyl-N-(3,4-dihydro-2H-chromen-7-ylmethyl)-N-isobutylmorpholine-2-carboxamide

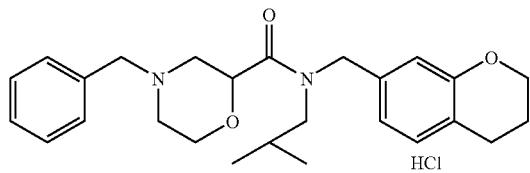

Employing the procedure as described for Example 19, Step 8, but substituting benzaldehyde for o-anisaldehyde, product was obtained as the hydrochloride salt. MS (m+1)= 423.3; H NMR (400 MHz, CD3OD) 7.54 (m, 5H), 7.00 (m, 1H), 6.64 (m, 2H), 4.95 (m, 1H), 4.72 (m, 1H), 4.6-4.3 (m, 3H), 4.13 (m, 3H), 3.82 (m, 1H), 3.39-3.30 (m, 3H, obscured by CH3OD peak), 3.21 (m, 2H), 3.08-2.89 (m, 1H), 2.75 (t, 2H, J 6 Hz), 1.98 (m, 3H), 0.87 (d, 6H, J 7 Hz).

Example 21

(±)-N-(3,4-Dihydro-2H-chromen-6-ylmethyl)-N-isobutyl-4-(2-methoxybenzyl)morpholine-2-carboxamide

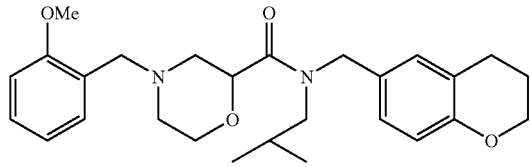

Step 1: (±)-tert-Butyl 2-{[(3,4-dihydro-2H-chromen-6-ylmethyl)(isobutyl)amino]carbonyl}morpholine-4-carboxylate Employing the procedure as described for Example 15, Step 6, but substituting N-(3,4-dihydro-2H-chromen-6-ylmethyl)-2-methylpropan-1-amine (prepared by formylation of chromane using the procedure described for Example 8, Step 1, followed by reductive amination with excess isobutylamine as described for Example 1, Step 2) for 2-methyl-N-(2,3,4,5-tetrahydro-1-benzoxepin-8-ylmethyl)propan-1-amine, product was obtained as a solid white foam. MS (m+1)= 433.4; H NMR (400 MHz, CDCl3) 6.88 (m, 2H), 6.74 (m, 1H), 4.6 (m, 1H), 4.43 (d, 1H, J 17 Hz), 4.19-4.00 (m, 4H), 3.96-3.84 (m, 2H), 3.51 (m, 1H), 3.22 (m, 2H), 3.01 (m, 2H), 2.76 (m, 2H), 2.00 (m, 3H), 1.46 (d, 9H, J 11 Hz), 0.90 (m, 6H).

Step 2: (±)-N-(3,4-dihydro-2H-chromen-6-ylmethyl)-N-isobutylmorpholine-2-carboxamide hydrochloride Employing the procedure as described for Example 15, Step 7, but substituting (±)-tert-butyl 2-{[(3,4-dihydro-2H-chromen-6-ylmethyl)(isobutyl)amino]carbonyl} morpholine-4-carboxylate for (±)-tert-butyl 2-{[isobutyl (2,3,4,5-tetrahydro-1-benzoxepin-8-ylmethyl)amino]carbonyl} morpholine-4-carboxylate, product was obtained as a solid white foam. MS (m+1)=333.3; H NMR (400 MHz, CD3OD) 6.93 (m, 2H), 6.69 (m, 1H), 4.76-4.66 (m, 2H), 4.52-4.34 (m, 1H), 4.14 (m, 2H), 4.04 (m, 1H), 3.89 (m, 1H), 3.49-3.33 (m, 3H), 3.25 (m, 2H), 3.12-2.92 (m, 1H), 2.75 (m, 2H), 2.01 (m, 1H), 1.97 (m, 2H), 0.90 (m, 6H).

Step 3: (±)-N-(3,4-Dihydro-2H-chromen-6-ylmethyl)-N-isobutyl-4-(2-methoxybenzyl)morpholine-2-carboxamide hydrochloride Employing the procedure as described for Example 15, Step 8, but substituting (±)-N-(3,4-dihydro-2H-chromen-6-ylmethyl)-N-isobutylmorpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)= 453.3; H NMR (400 MHz, CD3OD) 7.51 (t, 1H, J 8 Hz), 7.41 (m, 1H), 7.15 (m, 1H), 7.06 (t, 1H, J 7 Hz), 6.93 (m, 2H), 6.69 (m, 1H), 5.01 (m, 1H), 4.68 (m, 1H), 4.58-4.38 (m, 3H), 4.14 (m, 2H), 4.01-3.82 (m, 5H), 3.57-3.36 (m, 3H), 3.27-2.89 (m, 3H), 2.75 (t, 2H, J 6 Hz), 2.04 (m, 1H), 1.96 (m, 2H), 0.88 (m, 6H).

Example 22

(±)-N-[(9-Hydroxy-6,7,8,9-tetrahydro-5H-benzo[7]annulen-2-yl)methyl]-N-isobutyl-4-(2-methoxybenzyl)morpholine-2-carboxamide

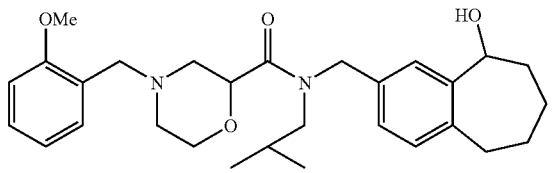

Step 1:
3-Bromo-6,7,8,9-tetrahydro-5H-benzo[7]annulen-5-ol

To a stirred solution of 1.91 g (8.0 mmol) of 3-bromo-6,7,8,9-tetrahydro-5H-benzo[7]annulen-5-one (J. Med. Chem. 2000, 43, 2049-2063) in 40 mL of ethanol under nitrogen cooled in an ice-bath was added 0.635 g (16.8 mmol, 2.1 equiv) of sodium borohydride. After three hours 32 mL of saturated sodium bicarbonate solution was added, and the mixture was concentrated under reduced pressure to remove the ethanol. The aqueous residue was diluted with 8 mL water and extracted with 2×80 mL of ethyl acetate. The combined extract was washed with 10 mL each of water and brine, dried over sodium sulfate, filtered, and concentrated to give product as a white crystalline solid. MS (m+1)=242.2; 1H NMR (400 MHz, CDCl3) 7.62 (s, 1H), 7.25 (m, 1H), 6.95 (d, 1H, J 8 Hz), 4.89 (d, 1H, J 9 Hz), 2.84 (m, 1H), 2.65 (d, 1H, J 12 Hz), 1.99 (m, 2H), 1.78 (m, 4H), 1.38 (m, 1H).

Step 2: (±)-2-[(3-Bromo-6,7,8,9-tetrahydro-5H-benzo[7]annulen-5-yl)oxy]tetrahydro-2H-pyran A mixture of 1.88 g (7.8 mmol) of (±)-3-bromo-6,7,8,9-tetrahydro-5H-benzo[7]annulen-5-ol, 1.07 mL (11.7 mmol, 1.5 equiv) of 3,4-dihydro-2H-pyran, and 0.20 g (0.80 mmol, 0.1 equiv) of pyridinium p-toluenesulfonate in 38 mL of methylene chloride was stirred under nitrogen at ambient temperature overnight. The mixture was diluted with 115 mL of ether, washed with 45 mL of half-saturated sodium chloride solution, dried over sodium sulfate, filtered, and concentrated to give 2.8 g of a cloudy oil. Purification by flash chromatography (5-30% ethyl acetate in hexanes) gave the product as a colorless oil. MS (m+1)=327.0; 1H NMR (400 MHz, CDCl3) 7.68 (s, 0.5H), 7.39 (d, 0.5H, J 2 Hz), 7.25 (m, 1H), 6.95 (m, 1H), 4.90 (t, 0.5H, J 3 Hz), 4.80 (m, 1H), 4.48 (t, 0.5H, J 3 Hz), 3.95 (m, 0.5H), 3.67 (m, 0.5H), 3.52 (m, 0.5H), 3.42 (m, 0.5H), 2.85 (m, 1H), 2.67 (m, 1H), 2.10-1.83 (m, 3.5H), 1.82-1.52 (m, 8H), 1.43 (m, 0.5H).

Step 3: (±)-9-(Tetrahydro-2H-pyran-2-yloxy)-6,7,8,9-tetrahydro-5H-benzo[7]annulene-2-carbaldehyde Employing the procedure as described for Example 1, Step 4, but substituting (±)-2-[(3-bromo-6,7,8,9-tetrahydro-5H-benzo[7]annulen-5-yl)oxy]tetrahydro-2H-pyran for 8-bromo-2,3,4,5-tetrahydro-1-benzoxepine, product was obtained as a colorless oil. MS (m+1)=275.2; 1H NMR (400 MHz, CDCl3) 9.98 (d, 1H, J 10 Hz), 8.06 (s, 0.5H), 7.78 (s, 0.5H), 7.67 (m, 1H), 7.25 (m, 1H), 4.93 (m, 1.5H), 4.48 (t, 0.5H, J 4 Hz), 3.97 (m, 0.5H), 3.65 (m, 0.5H), 3.52 (m, 0.5H), 3.41 (m, 0.5H), 3.04 (m, 1H), 2.79 (m, 1H), 2.12 (m, 1H), 1.93 (m, 2H), 1.84-1.66 (m, 4H), 1.62-1.45 (m, 5H).

Step 4: (±)-2-Methyl-N-{[9-(tetrahydro-2H-pyran-2-yloxy)-6,7,8,9-tetrahydro-5H-benzo[7]annulen-2-yl]methyl}propan-1-amine Employing the procedure as described for Example 15, Step 5, but substituting (±)-9-(tetrahydro-2H-pyran-2-yloxy)-6,7,8,9-tetrahydro-5H-benzo[7]annulene-2-carbaldehyde for 2,3,4,5-tetrahydro-1-benzoxepine-8-carbaldehyde, product was obtained as a colorless oil. MS (m+1)=332.3; 1H NMR (400 MHz, CDCl3) 7.46 (s, 0.5H), 7.18 (s, 0.5H), 7.10 (m, 1H), 7.05 (m, 1H), 4.92 (t, 0.5H, J 3 Hz), 4.85 (m, 1H), 4.47 (t, 0.5H, J 4 Hz), 3.96 (m, 0.5H), 3.75 (d, 2H, J 8 Hz), 3.70 (m, 0.5H), 3.50 (m, 0.5H), 3.40 (m, 0.5H), 2.95 (m, 1H), 2.68 (m, 1H), 2.44 (m, 2H), 2.15-1.95 (m, 2H), 1.91 (m, 2H), 1.76 (m, 4H), 1.62-1.56 (m, 6H), 0.91 (m, 6H).

Step 5: (±)-tert-Butyl 2-[(isobutyl {[9-(tetrahydro-2H-pyran-2-yloxy)-6,7,8,9-tetrahydro-5H-benzo[7]annulen-2-yl]methyl}amino)carbonyl]morpholine-4-carboxylate Employing the procedure as described for Example 15, Step 6, but substituting (±)-2-methyl-N-{[9-(tetrahydro-2H-pyran-2-yloxy)-6,7,8,9-tetrahydro-5H-benzo[7]annulen-2-yl]methyl}propan-1-amine for (±)-2-methyl-N-(2,3,4,5-tetrahydro-1-benzoxepin-8-ylmethyl)propan-1-amine, product was obtained as a solid white foam. MS (m+1)=545.4; 1H NMR (400 MHz, CDCl3) 7.39 (m, 0.5H), 7.10-6.94 (m, 2.5H), 4.91 (s, 0.5H), 4.85 (m, 1H), 4.72 (m, 1H), 4.52 (s, 0.5H), 4.48 (m, 1H), 4.06 (m, 2H), 3.93 (m, 3H), 3.65 (m, 0.5H), 3.56-3.35 (m, 2.5H), 3.21 (m, 2H), 3.06-2.88 (m, 3H), 2.70 (m, 1H), 2.12-1.88 (m, 4H), 1.82-1.65 (m, 5H), 1.56 (m, 3H, obscured by H2O peak), 1.45 (m, 9H), 0.89 (m, 6H).

Step 6: (±)-tert-Butyl 2-{[[(9-hydroxy-6,7,8,9-tetrahydro-5H-benzo[7]annulen-2-yl)methyl](isobutyl) amino]-carbonyl}morpholine-4-carboxylate A mixture of 1.91 g (3.5 mmol) of (±)-tert-butyl 2-[(isobutyl {[9-(tetrahydro-2H-pyran-2-yloxy)-6,7,8,9-tetrahydro-5H-benzo[7]annulen-2-yl]methyl}amino)carbonyl]morpholine-4-carboxylate and 0.088 g (0.35 mmol, 0.1 equiv) of pyridinium p-toluenesulfonate in 25 mL of ethanol was stirred under nitrogen at 55° C. overnight. The reaction mixture was concentrated under reduced pressure and the residue was purified by flash chromatography (10-50% ethyl acetate in hexanes) to give the product as a solid white foam. MS (m+1)=461.4; H NMR (400 MHz, CDCl3) 7.29 (m, 1H), 7.05 (m, 1H), 6.96 (m, 1H), 4.91 (t, 1H, J 8 Hz), 4.75 (m, 1H), 4.48 (d, 1H, J 16 Hz), 4.18-4.02 (m, 2H), 4.01-3.80 (m, 2H), 3.57-3.38 (m, 2H), 3.21 (m, 1H), 3.10-2.85 (m, 3H), 2.69 (m, 1H), 2.01 (m, 3H), 1.78 (m, 3H), 1.57 (m, 2H, obscured by H2O peak), 1.45 (d, 9H, J 15 Hz), 0.90 (m, 6H).

Step 7: N-[(9-hydroxy-6,7,8,9-tetrahydro-5H-benzo[7]annulen-2-yl)methyl]-N-isobutylmorpholine-2-carboxamide hydrochloride Employing the procedure as described for Example 15, Step 7, but substituting (±)-tert-butyl 2-{[[(9-hydroxy-6,7,8,9-tetrahydro-5H-benzo[7]annulen-2-yl)methyl](isobutyl)amino]-carbonyl}morpholine-4-carboxylate for (±)-tert-butyl 2-{[isobutyl(2,3,4,5-tetrahydro-1-benzoxepin-8-ylmethyl)amino]carbonyl}morpholine-4-carboxylate, product was obtained as a solid white foam. MS (m+1)= 361.3; H NMR (400 MHz, CD3OD) 7.35 (m, 1H), 7.09 (m, 1H), 7.00 (m, 1H), 4.85 (m, 2.5H, obscured by CD3OH peak), 4.66 (m, 0.5H), 4.60-4.44 (m, 1H), 4.05 (m, 1H), 3.87 (m, 1H), 3.44 (m, 2H), 3.39-3.20 (m, 3H, obscured by CH3OD peak), 3.16-2.92 (m, 1H), 2.86 (m, 1H), 2.72 (m, 1H), 2.00 (m, 3H), 1.82 (m, 2H), 1.62 (m, 1H), 1.33 (m, 1H), 0.91 (m, 6H).

Step 8: (±)-N-[(9-Hydroxy-6,7,8,9-tetrahydro-5H-benzo[7]annulen-2-yl)methyl]-N-isobutyl-4-(2-methoxybenzyl)morpholine-2-carboxamide hydrochloride Employing the procedure as described for Example 15, Step 8, but substituting (±)-N-[(9-hydroxy-6,7,8,9-tetrahydro-5H-benzo[7]annulen-2-yl)methyl]-N-isobutylmorpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)=481.3; H NMR (400 MHz, CD3OD) 7.51 (d, 1H, J 8 Hz), 7.48-7.30 (m, 2H), 7.15 (m, 1H), 7.08-6.95 (m, 3H), 5.01 (d, 0.5H, J 12 Hz), 4.78 (m, 0.5H), 4.61-4.50 (m, 1H), 4.42 (m, 2.5H), 4.20-4.05 (m, 0.5H), 4.01-3.89 (m, 5H), 3.56 (m, 1H), 3.49-3.39 (m, 3H), 3.3 (m, 2H, obscured by CH3OD peak), 3.16-2.95 (m, 1H), 2.86 (m, 1H), 2.71 (t, 1H, J 12 Hz), 1.99 (m, 3H), 1.81 (m, 2H), 1.59 (m, 1H), 1.31 (m, 1H), 0.89 (m, 6H).

Example 23

(±)-4-Benzyl-N-[(9-hydroxy-6,7,8,9-tetrahydro-5H-benzo[7]annulen-2-yl)methyl]-N-isobutylmorpholine-2-carboxamide

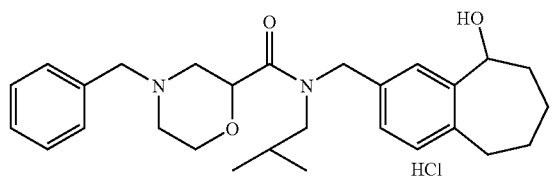

Employing the procedure as described for Example 22, Step 8, but substituting benzaldehyde for o-anisaldehyde, product was obtained as the hydrochloride salt. MS (m+1)= 451.4; H NMR (400 MHz, CD3OD) 7.54 (m, 5H), 7.32 (m, 1H), 7.09-6.92 (m, 2H), 4.97 (d, 0.5H, J 16 Hz), 4.8 (m, 0.5H, obscured by CD3OH peak), 4.70 (d, 0.5H, J 11 Hz), 4.55 (m, 1.5H), 4.41 (m, 1H), 4.19 (d, 1H, J 13 Hz), 4.1-3.8 (m, 1H), 3.54-3.3 (m, 6H), 3.22 (m, 1H), 3.12 (m, 0.5H), 2.88 (m, 1.5H), 2.71 (t, 1H, J 12 Hz), 1.99 (m, 3H), 1.82 (m, 2H), 1.60 (m, 1H), 1.29 (m, 1H), 0.87 (m, 6H).

Example 24

(±)-N-Isobutyl-4-(2-methoxybenzyl)-N-[(9-methoxy-6,7,8,9-tetrahydro-5H-benzo[7]annulen-2-yl)methyl]morpholine-2-carboxamide

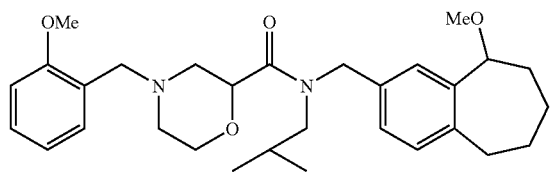

Step 1: (±)-tert-Butyl 2-({isobutyl[(9-methoxy-6,7,8,9-tetrahydro-5H-benzo[7]annulen-2-yl)methyl]amino}carbonyl)morpholine-4-carboxylate To a stirred mixture of 25 mg (0.62 mmol, 1.2 equiv) of 60% sodium hydride/mineral oil dispersion and 0.047 mL (0.75 mmol, 1.5 equiv) of iodomethane in 1 mL of anhydrous tetrahydrofuran under nitrogen was added a solution of 230 mg (0.50 mmol) of (±)-tert-butyl 2-{[[(9-hydroxy-6,7,8,9-tetrahydro-5H-benzo[7]annulen-2-yl)methyl](isobutyl)amino]-carbonyl}morpholine-4-carboxylate in 1 mL of anhydrous tetrahydrofuran over five minutes. The mixture was stirred at ambient temperature in a sealed flask for three days. The mixture was diluted with 2 mL of saturated sodium bicarbonate solution and extracted with 2×10 mL of ethyl acetate. The extract was washed with 3 mL each of water and brine, dried over sodium sulfate, filtered, and concentrated to give 263 mg of a gum. Purification by flash chromatography (10-50% ethyl acetate in hexanes) gave 171 mg (72%) of product as a solid white foam. MS (m+1)=475.4; H NMR (400 MHz, CDCl3) 7.06 (m, 2H), 6.96 (m, 1H), 4.7 (m, 1H), 4.50 (d, 1H, J 16 Hz), 4.28 (m, 1H), 4.18-4.02 (m, 2H), 3.97-3.80 (m, 2H), 3.50 (m, 1H), 3.31 (d, 3H, J 10 Hz), 3.22 (m, 2H), 2.99 (m, 3H), 2.65 (m, 1H), 2.01 (m, 2H), 1.86 (m, 2H), 1.75 (m, 1H), 1.60 (m, 2H), 1.45 (d, 9H, J 14 Hz), 0.89 (m, 6H).

Step 2: (±)-N-isobutyl-N-[(9-methoxy-6,7,8,9-tetrahydro-5H-benzo[7]annulen-2-yl)methyl]morpholine-2-carboxamide hydrochloride Employing the procedure as described for Example 15, Step 7, but substituting (±)-tert-butyl 2-({isobutyl[(9-methoxy-6,7,8,9-tetrahydro-5H-benzo[7]annulen-2-yl)methyl]amino}carbonyl)morpholine-4-carboxylate for (±)-tert-butyl 2-{[isobutyl(2,3,4,5-tetrahydro-1-benzoxepin-8-ylmethyl)amino]-carbonyl}morpholine-4-carboxylate, product was obtained as a solid white foam. MS (m+1)=375.3; H NMR (400 MHz, CD3OD) 7.16 (s, 1H), 7.00 (m, 2H), 4.81 (m, 1.5H), 4.80 (m, 0.5H), 4.63-4.41 (m, 1H), 4.33 (m, 1H), 4.03 (m, 1H), 3.89 (m, 1H), 3.38-3.22 (m, 8H, obscured by CH3OD peak), 3.12 (m, 0.5H), 2.97 (m, 1.5H), 2.68 (m, 1H), 2.00 (m, 2H), 1.80 (m, 3H), 1.59 (m, 2H), 0.92 (m, 6H).

Step 3: (±)-N-Isobutyl-4-(2-methoxybenzyl)-N-[(9-methoxy-6,7,8,9-tetrahydro-5H-benzo[7]annulen-2-yl)methyl]morpholine-2-carboxamide hydrochloride Employing the procedure as described for Example 15, Step 8, but substituting (±)-N-isobutyl-N-[(9-methoxy-6,7,8,9-tetrahydro-5H-benzo[7]annulen-2-yl)methyl]morpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)=495.4; N NMR (400 MHz, CD3OD) 7.51 (t, 1H, J 8 Hz), 7.41 (d, 1H, J 7 Hz), 7.20-6.99 (m, 5H), 5.02 (m, 0.5H), 4.74 (m, 1H), 4.59 (m, 0.5H), 4.40 (m, 2H), 4.32 (m, 1H), 4.20-4.04 (m, 1H), 4.01-3.80 (m, 4H), 3.57-3.38 (m, 3H), 3.3 (m, 6H, obscured by CH3OD peak), 3.16-2.92 (m, 2H), 2.68 (m, 1H), 2.02 (m, 2H), 1.88-1.72 (m, 3H), 1.59 (m, 2H), 0.88 (m, 6H).

Example 25

(±)-4-Benzyl-N-isobutyl-N-[(9-methoxy-6,7,8,9-tetrahydro-5H-benzo[7]annulen-2-yl)methyl]morpholine-2-carboxamide

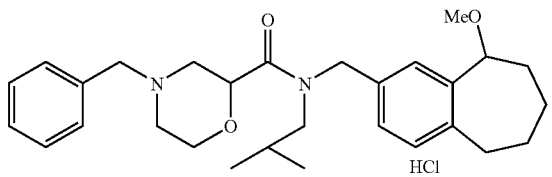

Employing the procedure as described for Example 24, Step 3, but substituting benzaldehyde for o-anisaldehyde, product was obtained as the hydrochloride salt. MS (m+1)= 465.4; H NMR (400 MHz, CD3OD) 7.54 (m, 5H), 7.16-6.95 (m, 3H), 4.97 (m, 0.5H), 4.73 (m, 1H), 4.56 (m, 1.5H), 4.41 (m, 1H), 4.31 (m, 1H), 4.17 (m, 1H), 4.12-3.75 (m, 1H), 3.55-3.20 (m, 9H, obscured by CH3OD peak), 3.10 (m, 0.5H), 2.95 (m, 1.5H), 2.67 (m, 1H), 2.03 (m, 2H), 1.80 (m, 3H), 1.61 (m, 2H), 0.87 (m, 6H).

Example 26

(±)-N-Isobutyl-4-(2-methoxybenzyl)-N-(6,7,8,9-tetrahydro-5H-benzo[7]annulen-2-ylmethyl)morpholine-2-carboxamide

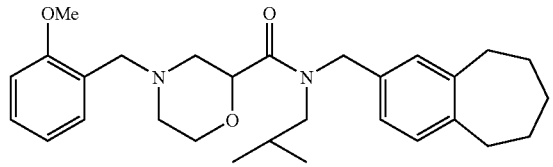

Step 1: (±)-tert-Butyl 2-{[isobutyl(6,7,8,9-tetrahydro-5H-benzo[7]annulen-2-ylmethyl)amino]carbonyl}morpholine-4-carboxylate A mixture of 230 mg 0.50 mmol) of (±)-tert-butyl 2-{[[(9-hydroxy-6,7,8,9-tetrahydro-5H-benzo[7]annulen-2-yl)methyl](isobutyl)amino]-carbonyl}morpholine-4-carboxylate, and 60 mg of 10% palladium on carbon catalyst in 5 mL of ethanol was stirred under of hydrogen (1 atmosphere) for four hours. The mixture was filtered and concentrated under reduced pressure. The residue was filtered through a pad of silica gel eluting with 33% ethyl acetate in hexanes. The filtrate was concentrated and the residue dried to give product as a gummy foam. MS (m+1)=445.4; H NMR (400 MHz, CDCl3) 7.04 (m, 1H), 6.89 (m, 2H), 4.7 (m, 1H), 4.45 (d, 1H, J 16 Hz), 4.18-4.02 (m, 2H), 3.90 (m, 2H), 3.51 (m, 1H), 3.22 (m, 2H), 3.03 (m, 2H), 2.77 (m, 4H), 2.00 (m, 1H), 1.82 (m, 2H), 1.63 (m, 4H), 1.45 (d, 9H, J 15 Hz), 0.91 (m, 6H).

Step 2: (±)-N-isobutyl-N-(6,7,8,9-tetrahydro-5H-benzo[7]annulen-2-ylmethyl)morpholine-2-carboxamide hydrochloride Employing the procedure as described for Example 15, Step 7, but substituting (±)-tert-butyl 2-{[isobutyl(6,7,8,9-tetrahydro-5H-benzo[7]annulen-2-ylmethyl)amino]carbonyl}morpholine-4-carboxylate for (±)-tert-butyl 2-{[isobutyl(2,3,4,5-tetrahydro-1-benzoxepin-8-ylmethyl)amino]carbonyl}morpholine-4-carboxylate, product was obtained as a solid white foam. MS (m+1)=345.3; H NMR (400 MHz, CD3OD) 7.05 (m, 1H), 6.95 (m, 2H), 4.78 (m, 1.5H), 4.65 (m, 0.5H), 4.56-4.38 (m, 1H), 4.03 (m, 1H), 3.88 (m, 1H), 3.50-3.31 (m, 2H), 3.3-3.21 (m, 3H, obscured by CH3OD peak), 3.14-2.92 (m, 1H), 2.78 (m, 4H), 2.02 (m, 1H), 1.85 (m, 2H), 1.61 (m, 4H), 0.91 (m, 6H).

Step 3: (±)-N-Isobutyl-4-(2-methoxybenzyl)-N-(6,7,8,9-tetrahydro-5H-benzo[7]annulen-2-ylmethyl)morpholine-2-carboxamide hydrochloride Employing the procedure as described for Example 15, Step 8, but substituting (±)-N-isobutyl-N-(6,7,8,9-tetrahydro-5H-benzo[7]annulen-2-ylmethyl)morpholine-2-carboxamide hydrochloride for (±)-N-isobutyl-N-(2,3,4,5-tetrahydro-1-benzoxepin-8-ylmethyl)morpholine-2-carboxamide hydrochloride, product was obtained as a solid white foam. MS (m+1)=465.3; H NMR (400 MHz, CD3OD) 7.51 (m, 1H), 7.41 (d, 1H, J 7 Hz), 7.15 (d, 1H, J 9 Hz), 7.07-6.88 (m, 4H), 5.00 (d, 0.5H, J 14 Hz), 4.73 (m, 1.5H), 4.55-4.35 (m, 3H), 4.18-3.75 (m, 5H), 3.56 (d, 1H, J 12 Hz), 3.49-3.37 (m, 2H), 3.3 (m, 2H, obscured by CH3OD peak), 3.18-2.89 (m, 1H), 2.78 (m, 4H), 2.05 (m, 1H), 1.85 (m, 2H), 1.60 (m, 4H), 0.90 (m, 6H).

Example 27

(±)-4-Benzyl-N-isobutyl-N-(6,7,8,9-tetrahydro-5H-benzo[7]annulen-2-ylmethyl)morpholine-2-carboxamide

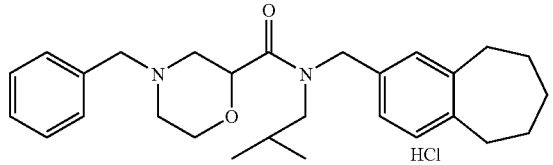

Employing the procedure as described for Example 26, Step 3, but substituting benzaldehyde for o-anisaldehyde, product was obtained as the hydrochloride salt. MS (m+1)=435.3; H NMR (400 MHz, CD3OD) 7.54 (m, 5H), 7.06-6.90 (m, 3H), 4.96 (d, 0.5H, J 16 Hz), 4.75 (m, 1.5H), 4.58 (m, 1H), 4.37 (d, 1H, J 15 Hz), 4.20-3.75 (m, 3H), 3.50 (m, 1H), 3.41 (m, 2H), 3.22 (m, 2H), 3.12-2.76 (m, 1H), 2.76 (m, 4H), 2.01 (m, 1H), 1.84 (m, 2H), 1.60 (m, 4H), 0.87 (m, 6H).

TABLE 1

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 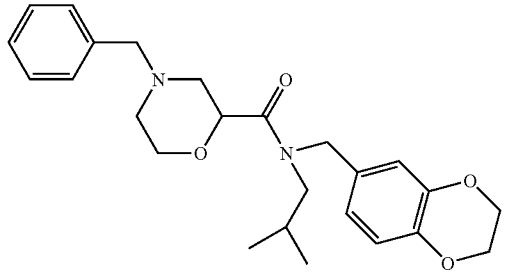 | (±)-4-benzyl-N-(2,3-dihydro-1,4-benzodioxin-6-ylmethyl)-N-isobutylmorpholine-2-carboxamide | 425.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 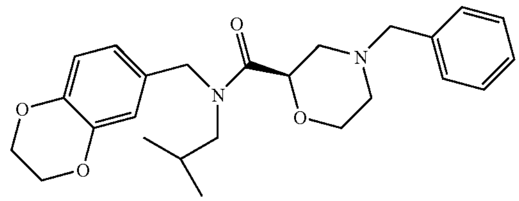 | (−)-(R)-4-benzyl-N-(2,3-dihydro-1,4-benzodioxin-6-ylmethyl)-N-isobutylmorpholine-2-carboxamide | 425.3 |
| 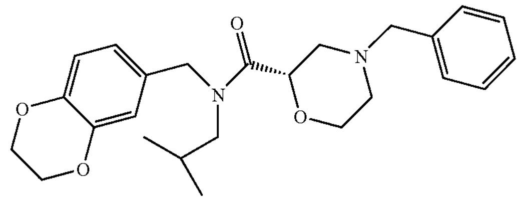 | (+)-(S)-4-benzyl-N-(2,3-dihydro-1,4-benzodioxin-6-ylmethyl)-N-isobutylmorpholine-2-carboxamide | 425.3 |
| 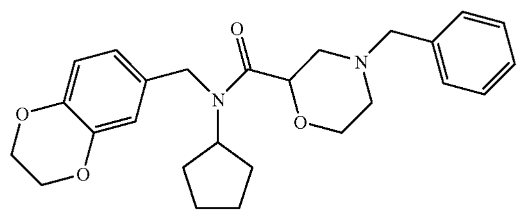 | (±)-4-benzyl-N-cyclopentyl-N-(2,3-dihydro-1,4-benzodioxin-6-ylmethyl)morpholine-2-carboxamide | 437.3 |
| 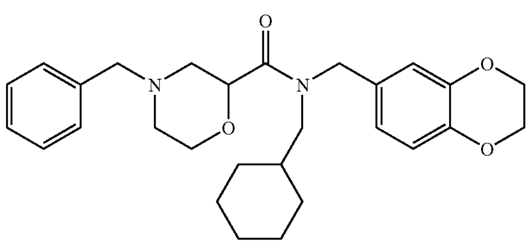 | (±)-4-benzyl-N-(cyclohexylmethyl)-N-(2,3-dihydro-1,4-benzodioxin-6-ylmethyl)morpholine-2-carboxamide | 465.2 |
| 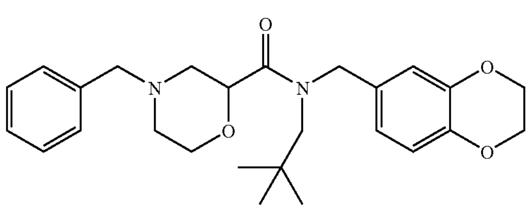 | (±)-4-benzyl-N-(2,3-dihydro-1,4-benzodioxin-6-ylmethyl)-N-(2,2-dimethylpropyl)morpholine-2-carboxamide | 439.2 |
| 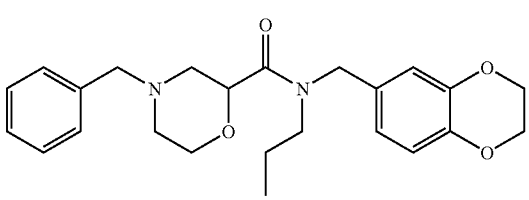 | 4-benzyl-N-(2,3-dihydro-1,4-benzodioxin-6-ylmethyl)-N-propylmorpholine-2-carboxamide | 411.2 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 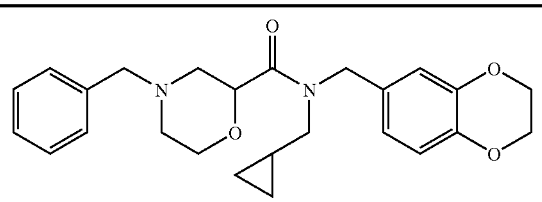 | 4-benzyl-N-(cyclopropylmethyl)-N-(2,3-dihydro-1,4-benzodioxin-6-ylmethyl)morpholine-2-carboxamide | 423.1 |
| 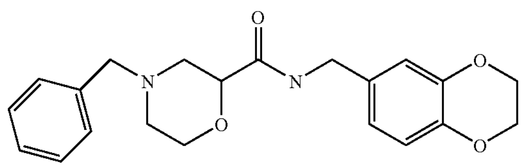 | (±)-4-benzyl-N-(2,3-dihydro-1,4-benzodioxin-6-ylmethyl)morpholine-2-carboxamide | 369.1807 |
| 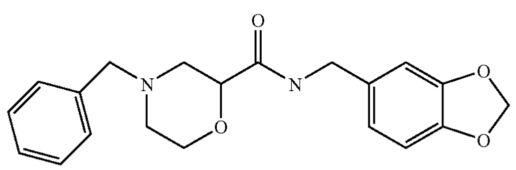 | (±)-N-(1,3-benzodioxol-5-ylmethyl)-4-benzylmorpholine-2-carboxamide | 355.1652 |
| 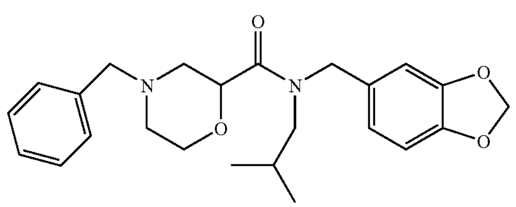 | (±)-N-(1,3-benzodioxol-5-ylmethyl)-4-benzyl-N-isobutylmorpholine-2-carboxamide | 411.2289 |
| 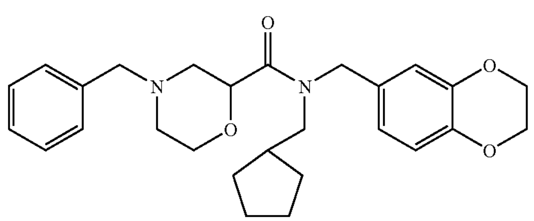 | (±)-4-benzyl-N-(cyclopentylmethyl)-N-(2,3-dihydro-1,4-benzodioxin-6-ylmethyl)morpholine-2-carboxamide | 451.2 |
| 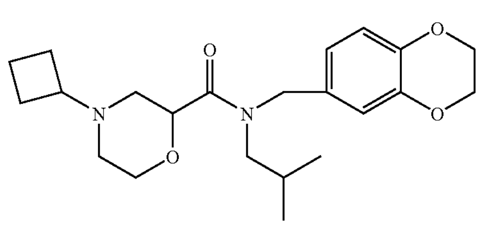 | (±)-4-cyclobutyl-N-(2,3-dihydro-1,4-benzodioxin-6-ylmethyl)-N-isobutylmorpholine-2-carboxamide | 389.2433 |
| 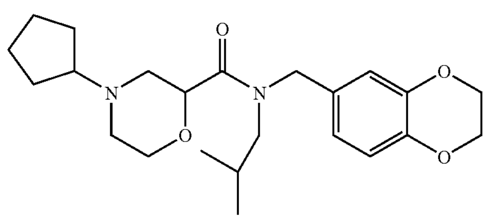 | (±)-4-cyclopentyl-N-(2,3-dihydro-1,4-benzodioxin-6-ylmethyl)-N-isobutylmorpholine-2-carboxamide | 403.2588 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 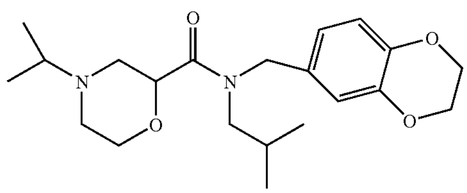 | (±)-N-(2,3-dihydro-1,4-benzodioxin-6-ylmethyl)-N-isobutyl-4-isopropylmorpholine-2-carboxamide | 377.2432 |
| 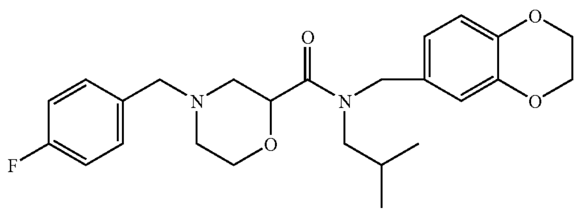 | (±)-N-(2,3-dihydro-1,4-benzodioxin-6-ylmethyl)-4-(4-fluorobenzyl)-N-isobutylmorpholine-2-carboxamide | 443.2338 |
| 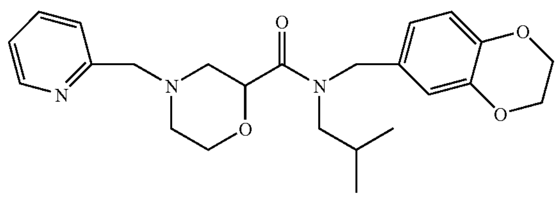 | (±)-N-(2,3-dihydro-1,4-benzodioxin-6-ylmethyl)-N-isobutyl-4-(pyridin-2-ylmethyl)morpholine-2-carboxamide | 426.2587 |
| 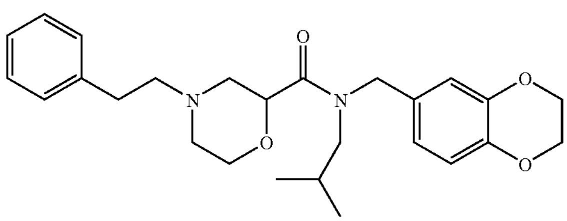 | (±)-N-(2,3-dihydro-1,4-benzodioxin-6-ylmethyl)-N-isobutyl-4-(2-phenylethyl)morpholine-2-carboxamide | 439.2587 |
| 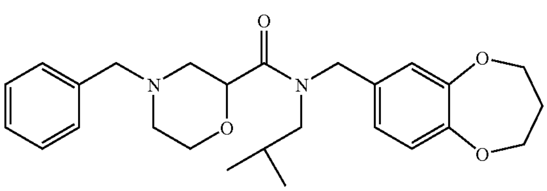 | (±)-4-benzyl-N-(3,4-dihydro-2H-1,5-benzodioxepin-7-ylmethyl)-N-isobutylmorpholine-2-carboxamide | 439.2 |
| 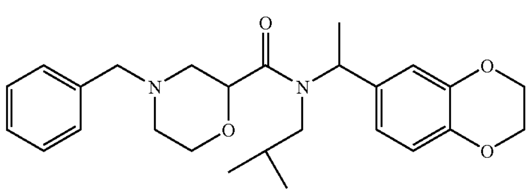 | (±)-4-benzyl-N-[1-(2,3-dihydro-1,4-benzodioxin-6-yl)ethyl]-N-isobutylmorpholine-2-carboxamide | 439.1 |
| 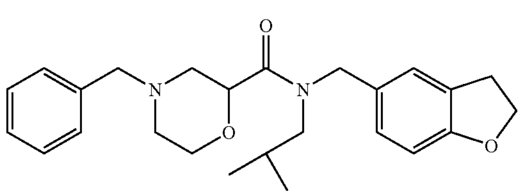 | (±)-4-benzyl-N-(2,3-dihydro-1-benzofuran-5-ylmethyl)-N-isobutylmorpholine-2-carboxamide | 409.2 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 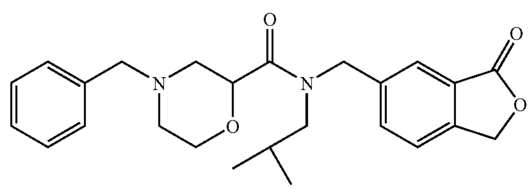 | (±)-4-benzyl-N-isobutyl-N-[(3-oxo-1,3-dihydro-2-benzofuran-5-yl)methyl]morpholine-2-carboxamide | 423.1 |
| 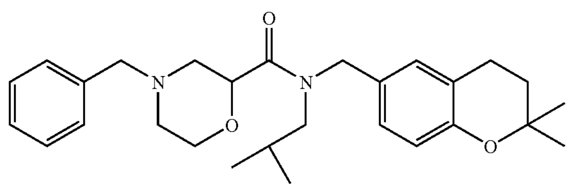 | (±)-4-benzyl-N-[(2,2-dimethyl-3,4-dihydro-2H-chromen-6-yl)methyl]-N-isobutylmorpholine-2-carboxamide | 451.3 |
| 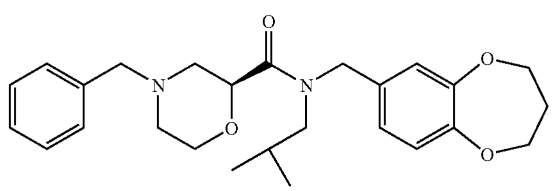 | (+)-(2S)-4-benzyl-N-(3,4-dihydro-2H-1,5-benzodioxepin-7-ylmethyl)-N-isobutylmorpholine-2-carboxamide | 439.2 |
| 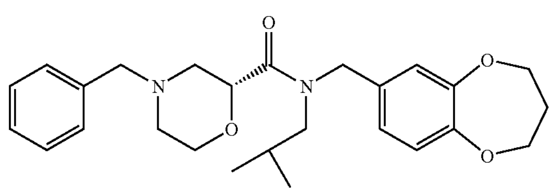 | (−)-(2R)-4-benzyl-N-(3,4-dihydro-2H-1,5-benzodioxepin-7-ylmethyl)-N-isobutylmorpholine-2-carboxamide | 439.2 |
| 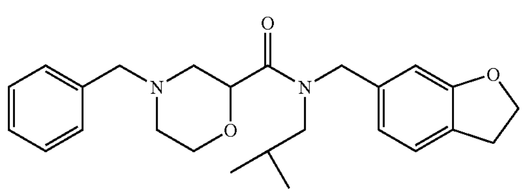 | (±)-4-benzyl-N-(2,3-dihydro-1-benzofuran-6-ylmethyl)-N-isobutylmorpholine-2-carboxamide | 409.2 |
| 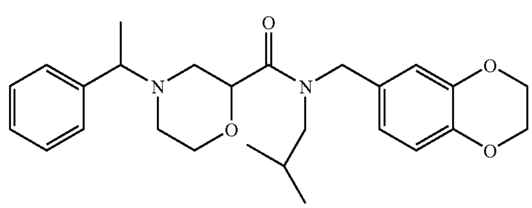 | (±)-N-(2,3-dihydro-1,4-benzodioxin-6-ylmethyl)-N-isobutyl-4-(1-phenylethyl)morpholine-2-carboxamide | 439.3 |
| 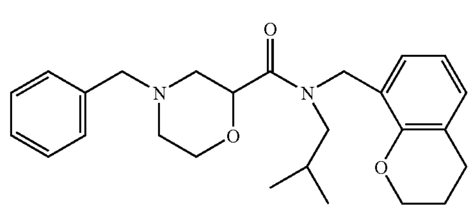 | (±)-4-benzyl-N-(3,4-dihydro-2H-chromen-8-ylmethyl)-N-isobutylmorpholine-2-carboxamide | 423.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 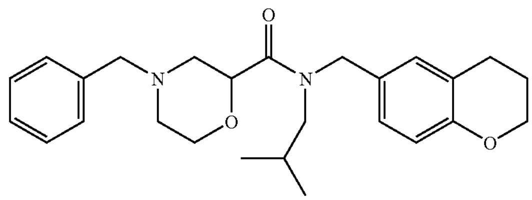 | (±)-4-benzyl-N-(3,4-dihydro-2H-chromen-6-ylmethyl)-N-isobutylmorpholine-2-carboxamide | 423.3 |
| 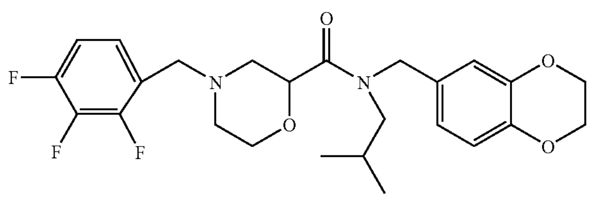 | (±)-N-(2,3-dihydro-1,4-benzodioxin-6-ylmethyl)-N-isobutyl-4-(2,3,4-trifluorobenzyl)morpholine-2-carboxamide | 479.2152 |
| 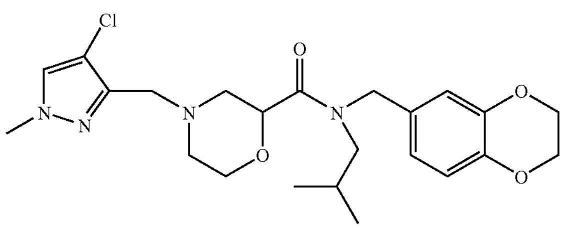 | (±)-4-[(4-chloro-1-methyl-1H-pyrazol-3-yl)methyl]-N-(2,3-dihydro-1,4-benzodioxin-6-ylmethyl)-N-isobutylmorpholine-2-carboxamide | 463.2107 |
| 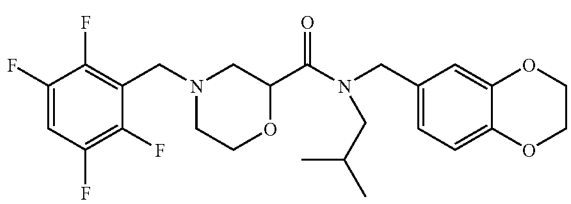 | (±)-N-(2,3-dihydro-1,4-benzodioxin-6-ylmethyl)-N-isobutyl-4-(2,3,5,6-tetrafluorobenzyl)morpholine-2-carboxamide | 497.2058 |
| 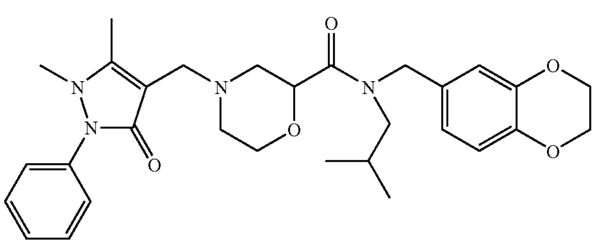 | (±) N-(2,3-dihydro-1,4-benzodioxin-6-ylmethyl)-4-[(1,5-dimethyl-3-oxo-2-phenyl-2,3-dihydro-1H-pyrazol-4-yl)methyl]-N-isobutylmorpholine-2-carboxamide | 535.2915 |
| 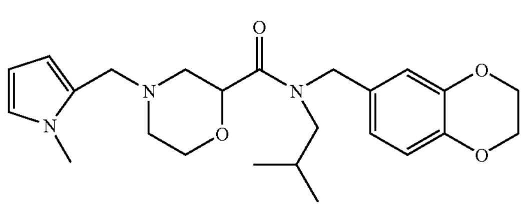 | (±)-N-(2,3-dihydro-1,4-benzodioxin-6-ylmethyl)-N-isobutyl-4-[(1-methyl-1H-pyrrol-2-yl)methyl]morpholine-2-carboxamide | 428.2544 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 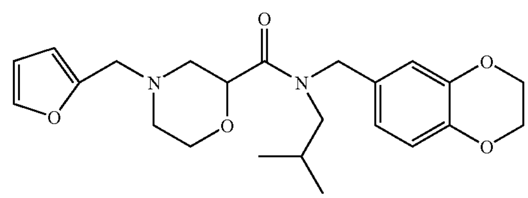 | (±)-N-(2,3-dihydro-1,4-benzodioxin-6-ylmethyl)-4-(2-furylmethyl)-N-isobutylmorpholine-2-carboxamide | 415.2228 |
| 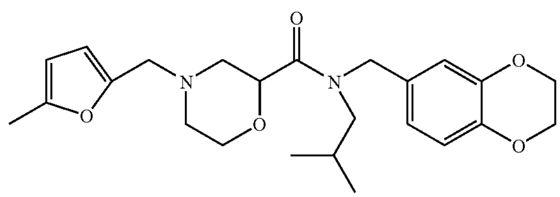 | (±)-N-(2,3-dihydro-1,4-benzodioxin-6-ylmethyl)-N-isobutyl-4-[(5-methyl-2-furyl)methyl]morpholine-2-carboxamide | 429.2384 |
| 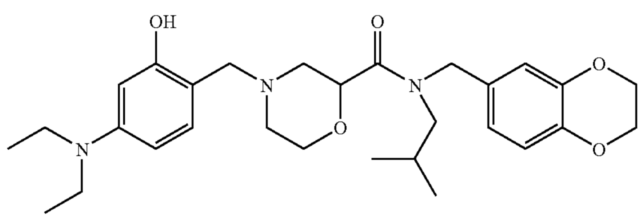 | (±)-4-[4-(diethylamino)-2-hydroxybenzyl]-N-(2,3-dihydro-1,4-benzodioxin-6-ylmethyl)-N-isobutylmorpholine-2-carboxamide | 512.3119 |
| 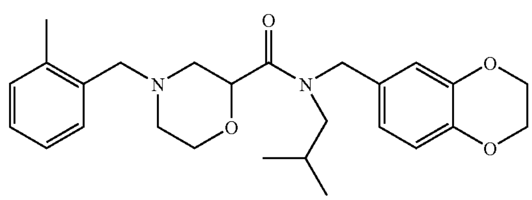 | (±)-N-(2,3-dihydro-1,4-benzodioxin-6-ylmethyl)-N-isobutyl-4-(2-methylbenzyl)morpholine-2-carboxamide | 439.2592 |
| 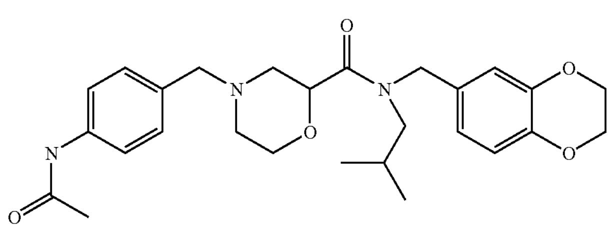 | (±)-4-[4-(acetylamino)benzyl]-N-(2,3-dihydro-1,4-benzodioxin-6-ylmethyl)-N-isobutylmorpholine-2-carboxamide | 482.265 |
| 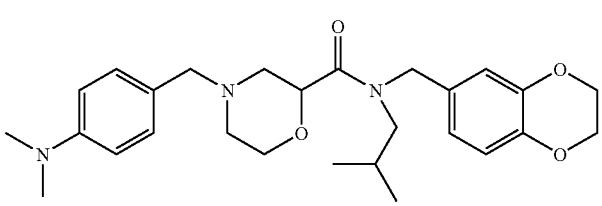 | (±)-N-(2,3-dihydro-1,4-benzodioxin-6-ylmethyl)-4-[4-(dimethylamino)benzyl]-N-isobutylmorpholine-2-carboxamide | 468.2857 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 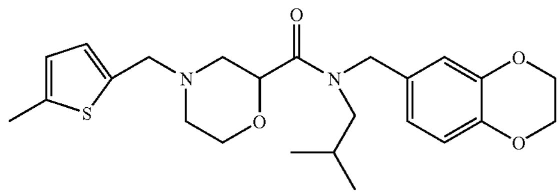 | (±)-N-(2,3-dihydro-1,4-benzodioxin-6-ylmethyl)-N-isobutyl-4-[(5-methyl-2-thienyl)methyl]morpholine-2-carboxamide | 445.2156 |
| 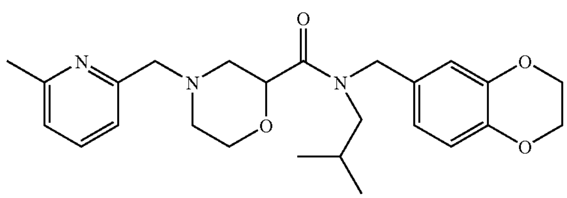 | (±)-N-(2,3-dihydro-1,4-benzodioxin-6-ylmethyl)-N-isobutyl-4-[(6-methylpyridin-2-yl)methyl]morpholine-2-carboxamide | 440.2544 |
| 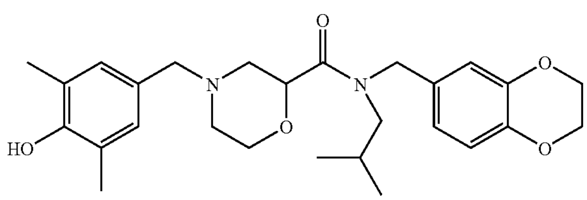 | (±)-N-(2,3-dihydro-1,4-benzodioxin-6-ylmethyl)-4-(4-hydroxy-3,5-dimethylbenzyl)-N-isobutylmorpholine-2-carboxamide | 469.2697 |
| 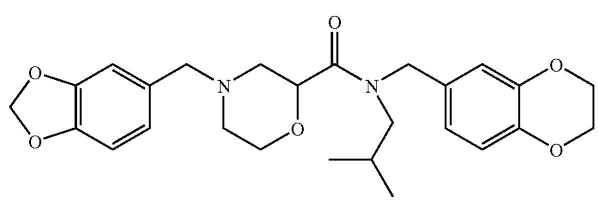 | (±)-4-(1,3-benzodioxol-5-ylmethyl)-N-(2,3-dihydro-1,4-benzodioxin-6-ylmethyl)-N-isobutylmorpholine-2-carboxamide | 469.2333 |
| 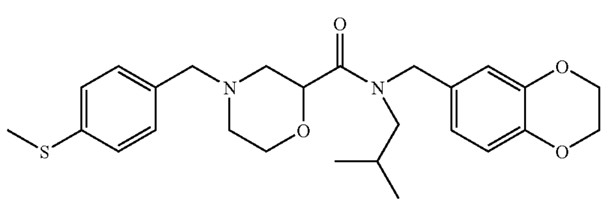 | (±)-N-(2,3-dihydro-1,4-benzodioxin-6-ylmethyl)-N-isobutyl-4-[4-(methylthio)benzyl]morpholine-2-carboxamide | 471.2312 |
| 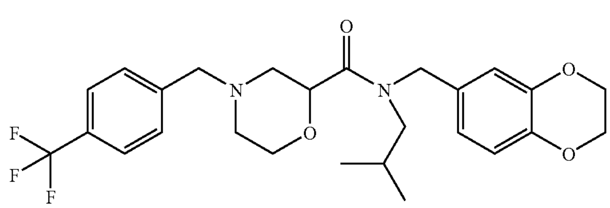 | (±)-N-(2,3-dihydro-1,4-benzodioxin-6-ylmethyl)-N-isobutyl-4-[4-(trifluoromethyl)benzyl]morpholine-2-carboxamide | 493.2309 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 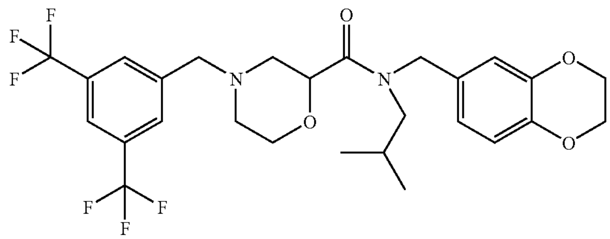 | (±)-4-[3,5-bis(trifluoromethyl)benzyl]-N-(2,3-dihydro-1,4-benzodioxin-6-ylmethyl)-N-isobutylmorpholine-2-carboxamide | 561.2183 |
| 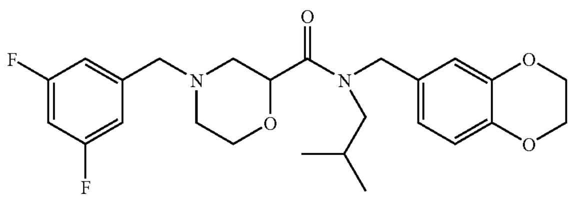 | (±)-4-(3,5-difluorobenzyl)-N-(2,3-dihydro-1,4-benzodioxin-6-ylmethyl)-N-isobutylmorpholine-2-carboxamide | 461.2247 |
| 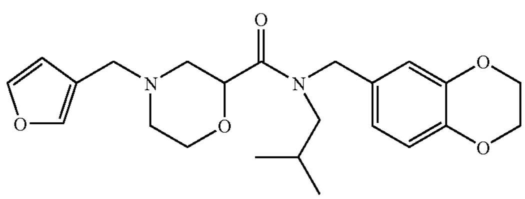 | (±)-N-(2,3-dihydro-1,4-benzodioxin-6-ylmethyl)-4-(3-furylmethyl)-N-isobutylmorpholine-2-carboxamide | 415.2228 |
| 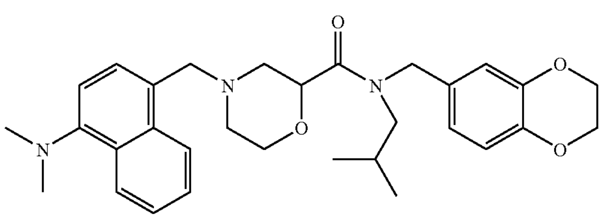 | (±)-N-(2,3-dihydro-1,4-benzodioxin-6-ylmethyl)-4-{[4-(dimethylamino)-1-naphthyl]methyl}-N-isobutylmorpholine-2-carboxamide | 518.3014 |
| 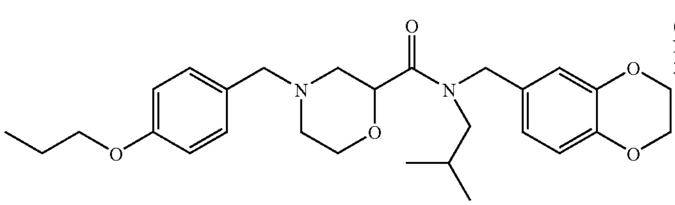 | (±)-N-(2,3-dihydro-1,4-benzodioxin-6-ylmethyl)-N-isobutyl-4-(4-propoxybenzyl)morpholine-2-carboxamide | 483.2854 |
| 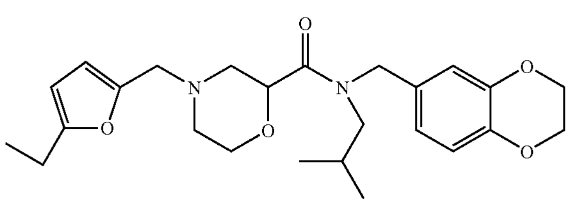 | (±)-N-(2,3-dihydro-1,4-benzodioxin-6-ylmethyl)-4-[(5-ethyl-2-furyl)methyl]-N-isobutylmorpholine-2-carboxamide | 443.2541 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 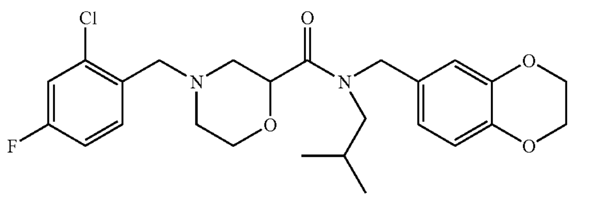 | (±)-4-(2-chloro-4-fluorobenzyl)-N-(2,3-dihydro-1,4-benzodioxin-6-ylmethyl)-N-isobutylmorpholine-2-carboxamide | 477.1951 |
|  | (±)-N-(2,3-dihydro-1,4-benzodioxin-6-ylmethyl)-N-isobutyl-4-[4-(trifluoromethoxy)benzyl]morpholine-2-carboxamide | 509.2258 |
| 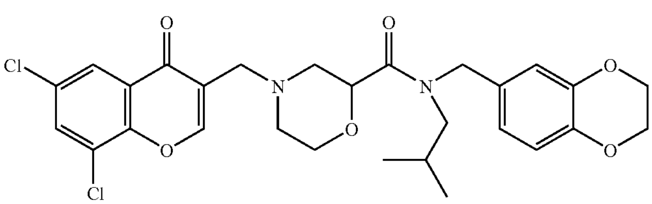 | (±)-4-[(6,8-dichloro-4-oxo-4H-chromen-3-yl)methyl]-N-(2,3-dihydro-1,4-benzodioxin-6-ylmethyl)-N-isobutylmorpholine-2-carboxamide | 561.1554 |
| 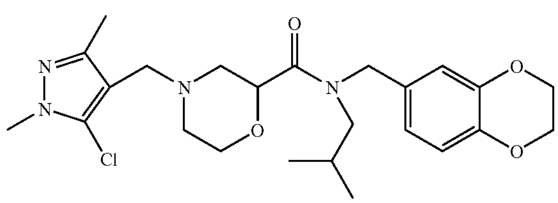 | (±)-4-[(5-chloro-1,3-dimethyl-1H-pyrazol-4-yl)methyl]-N-(2,3-dihydro-1,4-benzodioxin-6-ylmethyl)-N-isobutylmorpholine-2-carboxamide | 4772263 |
| 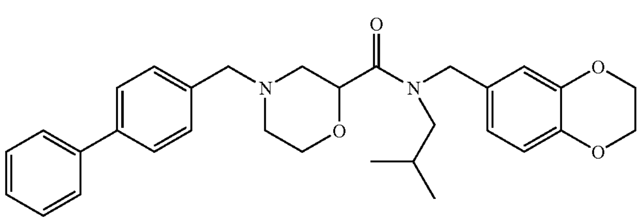 | (±)-4-(biphenyl-4-ylmethyl)-N-(2,3-dihydro-1,4-benzodioxin-6-ylmethyl)-N-isobutylmorpholine-2-carboxamide | 501.27748 |
| 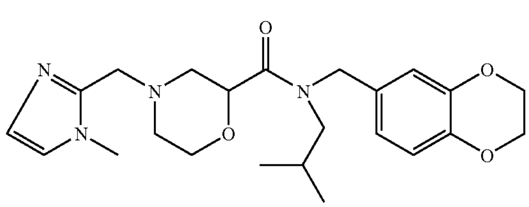 | (±)-N-(2,3-dihydro-1,4-benzodioxin-6-ylmethyl)-N-isobutyl-4-[(1-methyl-1H-imidazol-2-yl)methyl]morpholine-2-carboxamide | 429.2497 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
| --- | --- | --- |
| 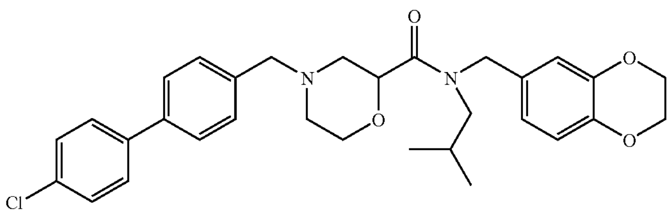 | (±)-4-[(4'-chlorobiphenyl-4-yl)methyl]-N-(2,3-dihydro-1,4-benzodioxin-6-ylmethyl)-N-isobutylmorpholine-2-carboxamide | 535.2358 |
| 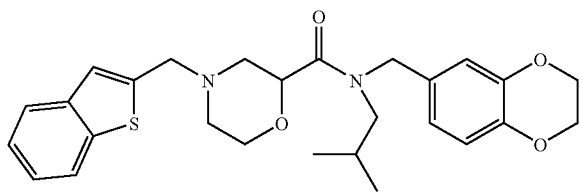 | (±)-4-(1-benzothien-2-ylmethyl)-N-(2,3-dihydro-1,4-benzodioxin-6-ylmethyl)-N-isobutylmorpholine-2-carboxamide | 481.2156 |
| 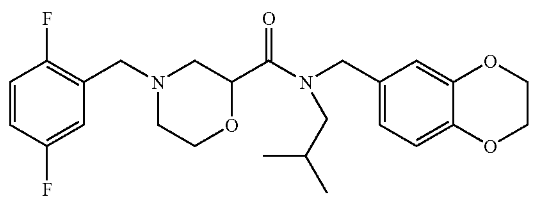 | (±)-4-(2,5-difluorobenzyl)-N-(2,3-dihydro-1,4-benzodioxin-6-ylmethyl)-N-isobutylmorpholine-2-carboxamide | 461.2247 |
| 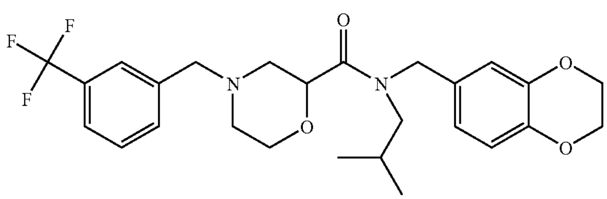 | (±)-N-(2,3-dihydro-1,4-benzodioxin-6-ylmethyl)-N-isobutyl-4-[3-(trifluoromethyl)benzyl]morpholine-2-carboxamide | 443.2341 |
| 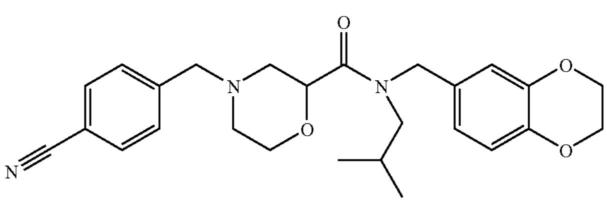 | (±)-4-(4-cyanobenzyl)-N-(2,3-dihydro-1,4-benzodioxin-6-ylmethyl)-N-isobutylmorpholine-2-carboxamide | 450.2428 |
| 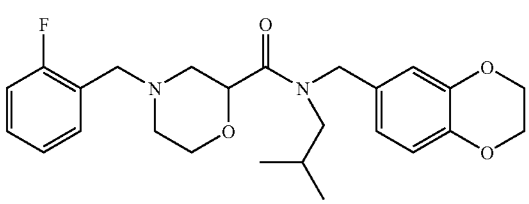 | (±)-N-(2,3-dihydro-1,4-benzodioxin-6-ylmethyl)-4-(2-fluorobenzyl)-N-isobutylmorpholine-2-carboxamide | 443.2383 |
| 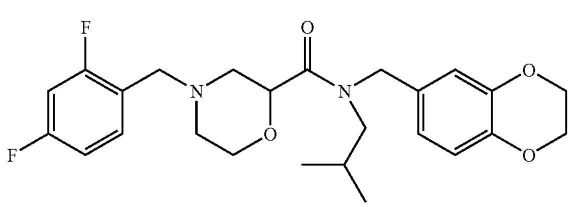 | (±)-4-(2,4-difluorobenzyl)-N-(2,3-dihydro-1,4-benzodioxin-6-ylmethyl)-N-isobutylmorpholine-2-carboxamide | 461.2251 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 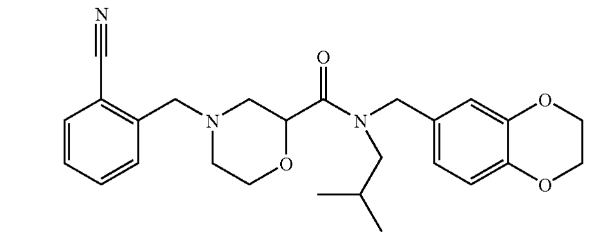 | (±)-4-(2-cyanobenzyl)-N-(2,3-dihydro-1,4-benzodioxin-6-ylmethyl)-N-isobutylmorpholine-2-carboxamide | 450.2388 |
| 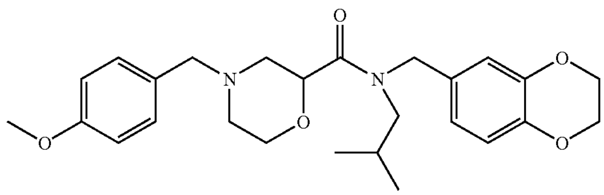 | (±)-N-(2,3-dihydro-1,4-benzodioxin-6-ylmethyl)-N-isobutyl-4-(4-methoxybenzyl)morpholine-2-carboxamide | 455.2586 |
| 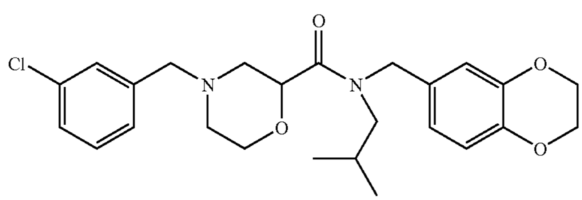 | (±)-4-(3-chlorobenzyl)-N-(2,3-dihydro-1,4-benzodioxin-6-ylmethyl)-N-isobutylmorpholine-2-carboxamide | 459.2085 |
| 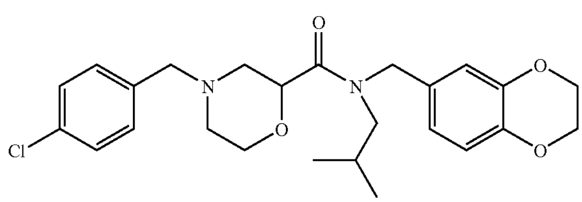 | (±)-4-(4-chlorobenzyl)-N-(2,3-dihydro-1,4-benzodioxin-6-ylmethyl)-N-isobutylmorpholine-2-carboxamide | 459.2092 |
| 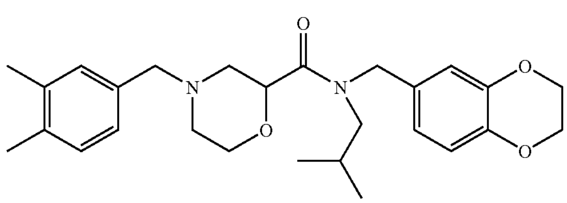 | (±)-N-(2,3-dihydro-1,4-benzodioxin-6-ylmethyl)-4-(3,4-dimethylbenzyl)-N-isobutylmorpholine-2-carboxamide | 453.2791 |
| 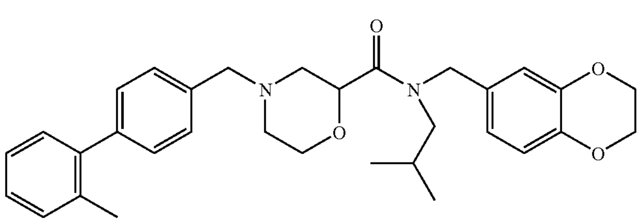 | (±)-N-(2,3-dihydro-1,4-benzodioxin-6-ylmethyl)-N-isobutyl-4-[(2'-methylbiphenyl-4-yl)methyl]morpholine-2-carboxamide | 515.2935 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 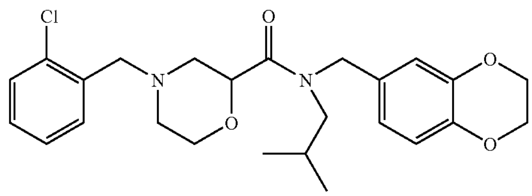 | (±)-4-(2-chlorobenzyl)-N-(2,3-dihydro-1,4-benzodioxin-6-ylmethyl)-N-isobutylmorpholine-2-carboxamide | 459.2053 |
| 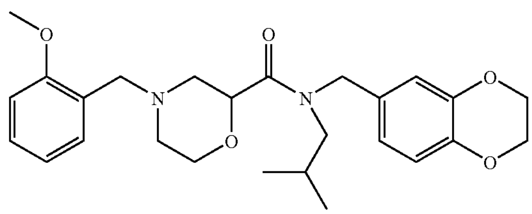 | (±)-N-(2,3-dihydro-1,4-benzodioxin-6-ylmethyl)-N-isobutyl-4-(2-methoxybenzyl)morpholine-2-carboxamide | 455.2557 |
| 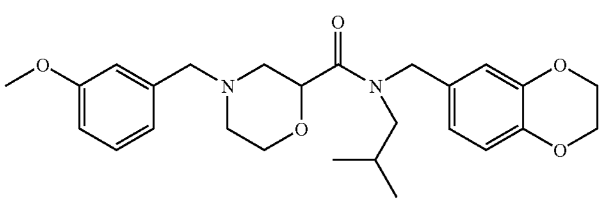 | (±)-N-(2,3-dihydro-1,4-benzodioxin-6-ylmethyl)-N-isobutyl-4-(3-methoxybenzyl)morpholine-2-carboxamide | 455.2562 |
| 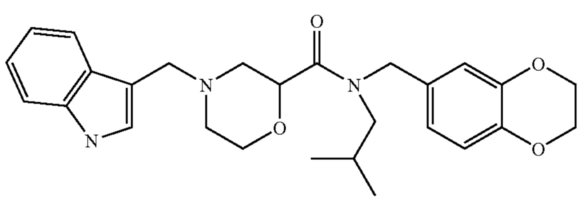 | (±)-N-(2,3-dihydro-1,4-benzodioxin-6-ylmethyl)-4-(1H-indol-3-ylmethyl)-N-isobutylmorpholine-2-carboxamide | 464.2555 |
| 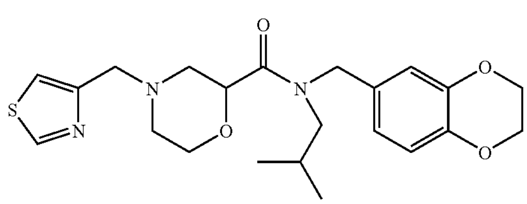 | (±)-N-(2,3-dihydro-1,4-benzodioxin-6-ylmethyl)-N-isobutyl-4-(1,3-thiazol-4-ylmethyl)morpholine-2-carboxamide | 432.1951 |
| 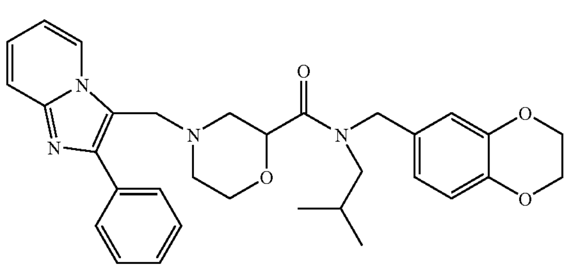 | (±)-N-(2,3-dihydro-1,4-benzodioxin-6-ylmethyl)-N-isobutyl-4-[(2-phenylimidazo[1,2-a]pyridin-3-yl)methyl]morpholine-2-carboxamide | 541.2790 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 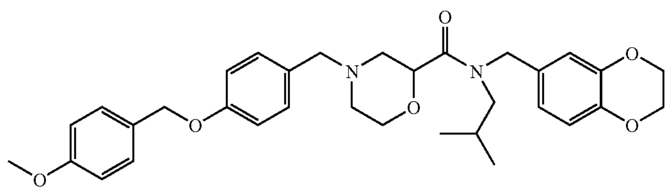 | (±)-N-(2,3-dihydro-1,4-benzodioxin-6-ylmethyl)-N-isobutyl-4-{4-[(4-methoxybenzyl)oxy]benzyl}morpholine-2-carboxamide | 561.2932 |
| 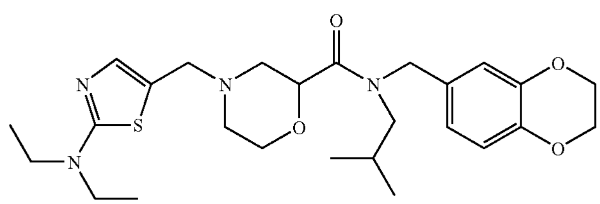 | (±)-4-{[2-(diethylamino)-1,3-thiazol-5-yl]methyl}-N-(2,3-dihydro-1,4-benzodioxin-6-ylmethyl)-N-isobutylmorpholine-2-carboxamide | 503.2679 |
| 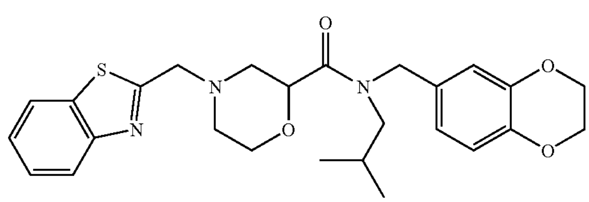 | (±)-4-(1,3-benzothiazol-2-ylmethyl)-N-(2,3-dihydro-1,4-benzodioxin-6-ylmethyl)-N-isobutylmorpholine-2-carboxamide | 482.2086 |
| 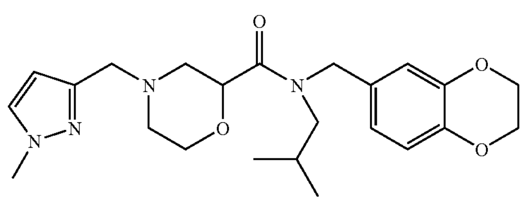 | (±)-N-(2,3-dihydro-1,4-benzodioxin-6-ylmethyl)-N-isobutyl-4-[(1-methyl-1H-pyrazol-3-yl)methyl]morpholine-2-carboxamide | 429.2512 |
| 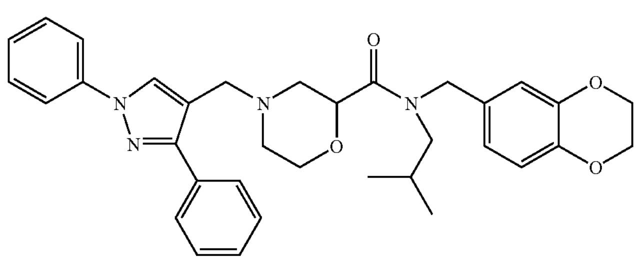 | (±)-N-(2,3-dihydro-1,4-benzodioxin-6-ylmethyl)-4-[(1,3-diphenyl-1H-pyrazol-4-yl)methyl]-N-isobutylmorpholine-2-carboxamide | 567.2941 |
| 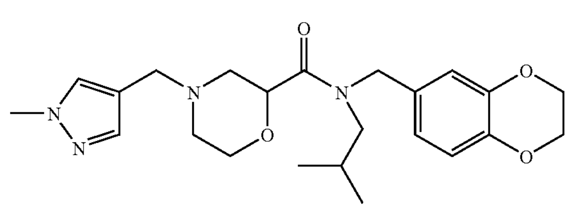 | (±)-N-(2,3-dihydro-1,4-benzodioxin-6-ylmethyl)-N-isobutyl-4-[(1-methyl-1H-pyrazol-4-yl)methyl]morpholine-2-carboxamide | 429.2506 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 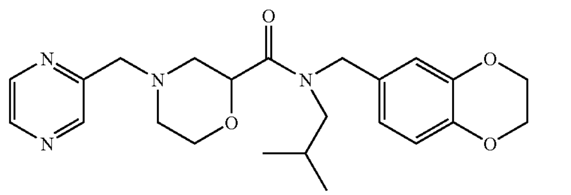 | (±)-N-(2,3-dihydro-1,4-benzodioxin-6-ylmethyl)-N-isobutyl-4-(pyrazin-2-ylmethyl)morpholine-2-carboxamide | 427.2346 |
| 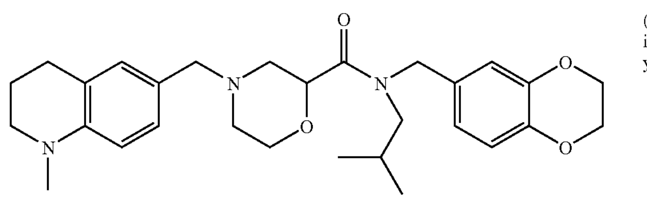 | (±)-N-(2,3-dihydro-1,4-benzodioxin-6-ylmethyl)-N-isobutyl-4-[(1-methyl-1,2,3,4-tetrahydroquinolin-6-yl)methyl]morpholine-2-carboxamide | 494.3024 |
| 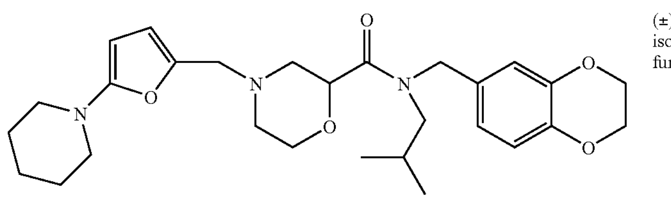 | (±)-N-(2,3-dihydro-1,4-benzodioxin-6-ylmethyl)-N-isobutyl-4-[(5-piperidin-1-yl-2-furyl)methyl]morpholine-2-carboxamide | 496.2783 |
| 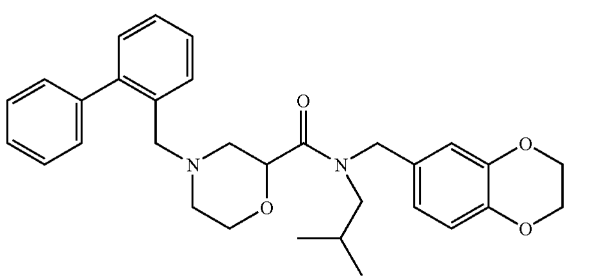 | (±)-4-(biphenyl-2-ylmethyl)-N-(2,3-dihydro-1,4-benzodioxin-6-ylmethyl)-N-isobutylmorpholine-2-carboxamide | 501.2765 |
| 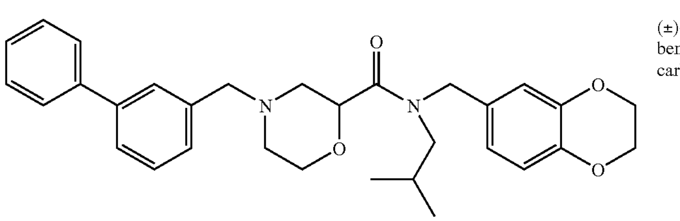 | (±)-4-(biphenyl-3-ylmethyl)-N-(2,3-dihydro-1,4-benzodioxin-6-ylmethyl)-N-isobutylmorpholine-2-carboxamide | 501.2776 |
| 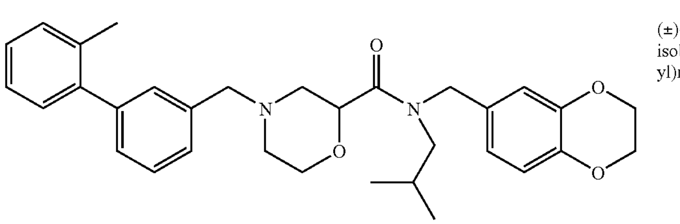 | (±)-N-(2,3-dihydro-1,4-benzodioxin-6-ylmethyl)-N-isobutyl-4-[(2'-methylbiphenyl-3-yl)methyl]morpholine-2-carboxamide | 515.294 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 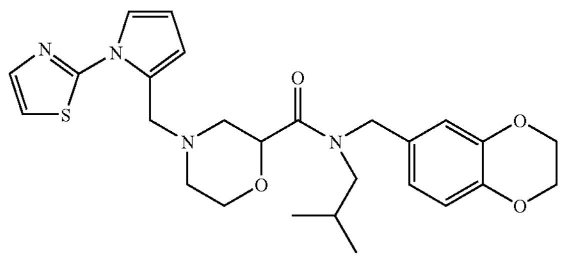 | (±)-N-(2,3-dihydro-1,4-benzodioxin-6-ylmethyl)-N-isobutyl-4-{[1-(1,3-thiazol-2-yl)-1H-pyrrol-2-yl]methyl}morpholine-2-carboxamide | 497.2217 |
| 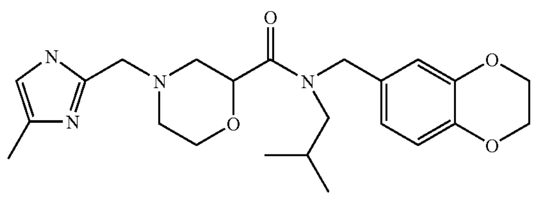 | (±)-N-(2,3-dihydro-1,4-benzodioxin-6-ylmethyl)-N-isobutyl-4-[(4-methyl-1H-imidazol-2-yl)methyl]morpholine-2-carboxamide | 429.2481 |
| 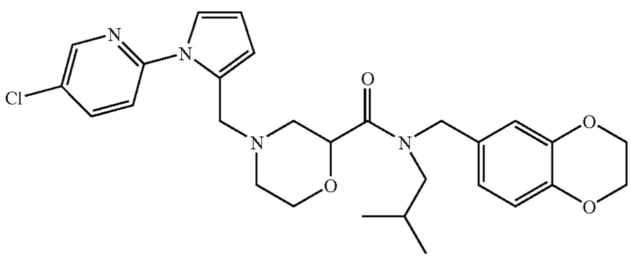 | (±)-4-{[1-(5-chloropyridin-2-yl)-1H-pyrrol-2-yl]methyl}-N-(2,3-dihydro-1,4-benzodioxin-6-ylmethyl)-N-isobutylmorpholine-2-carboxamide | 525.2292 |
| 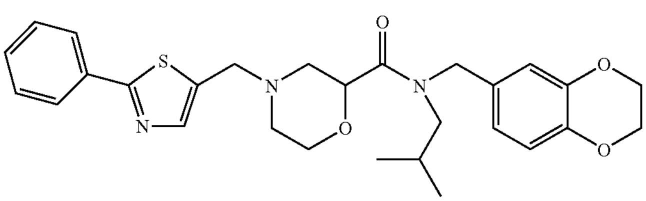 | (±)-N-(2,3-dihydro-1,4-benzodioxin-6-ylmethyl)-N-isobutyl-4-[(2-phenyl-1,3-thiazol-5-yl)methyl]morpholine-2-carboxamide | 508.2279 |
| 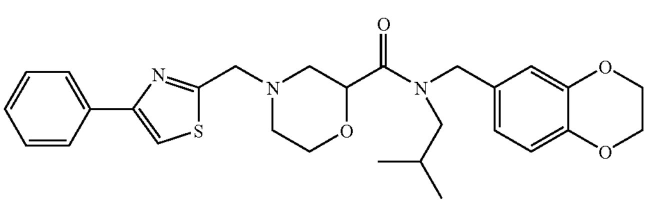 | (±)-N-(2,3-dihydro-1,4-benzodioxin-6-ylmethyl)-N-isobutyl-4-[(4-phenyl-1,3-thiazol-2-yl)methyl]morpholine-2-carboxamide | 508.2292 |
| 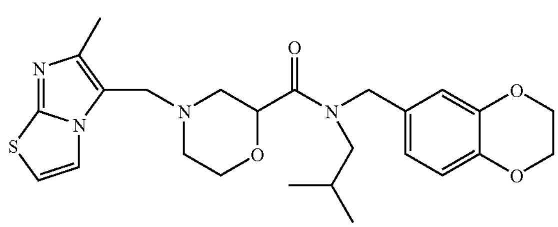 | (±)-N-(2,3-dihydro-1,4-benzodioxin-6-ylmethyl)-N-isobutyl-4-[(6-methylimidazo[2,1-b][1,3]thiazol-5-yl)methyl]morpholine-2-carboxamide | 485.2199 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 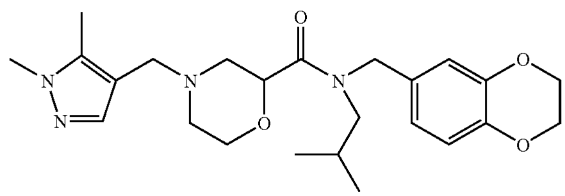 | (±)-N-(2,3-dihydro-1,4-benzodioxin-6-ylmethyl)-4-[(1,5-dimethyl-1H-pyrazol-4-yl)methyl]-N-isobutylmorpholine-2-carboxamide | 443.2662 |
| 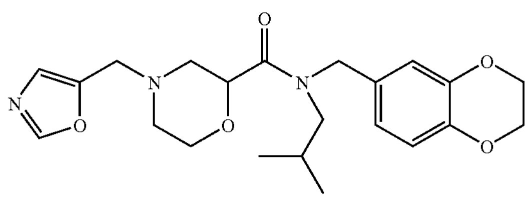 | (±)-N-(2,3-dihydro-1,4-benzodioxin-6-ylmethyl)-N-isobutyl-4-(1,3-oxazol-5-ylmethyl)morpholine-2-carboxamide | 416.2170 |
| 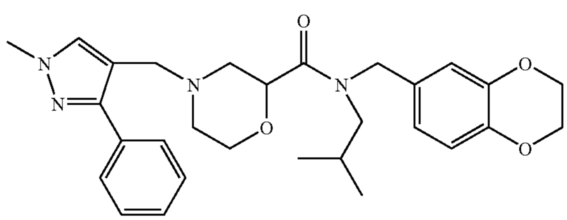 | (±)-N-(2,3-dihydro-1,4-benzodioxin-6-ylmethyl)-N-isobutyl-4-[(1-methyl-3-phenyl-1H-pyrazol-4-yl)methyl]morpholine-2-carboxamide | 505.2834 |
| 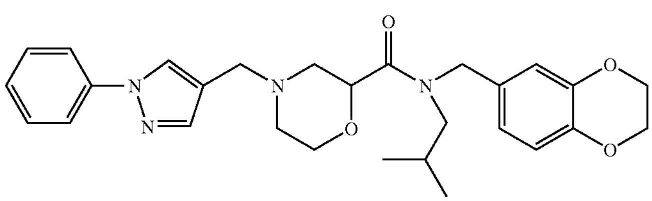 | (±)-N-(2,3-dihydro-1,4-benzodioxin-6-ylmethyl)-N-isobutyl-4-[(1-phenyl-1H-pyrazol-4-yl)methyl]morpholine-2-carboxamide | 491.2665 |
| 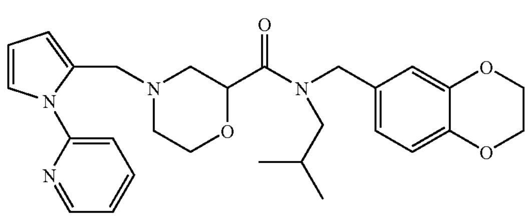 | (±)-N-(2,3-dihydro-1,4-benzodioxin-6-ylmethyl)-N-isobutyl-4-[(1-pyridin-2-yl-1H-pyrrol-2-yl)methyl]morpholine-2-carboxamide | 491.2255 |
| 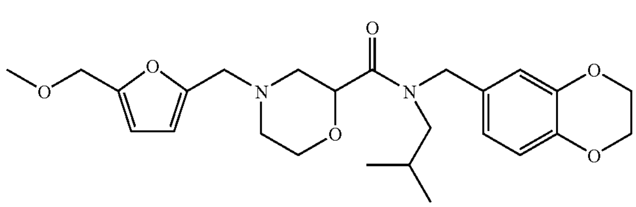 | (±)-N-(2,3-dihydro-1,4-benzodioxin-6-ylmethyl)-N-isobutyl-4-{[5-(methoxymethyl)-2-furyl]methyl}morpholine-2-carboxamide | 459.2494 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 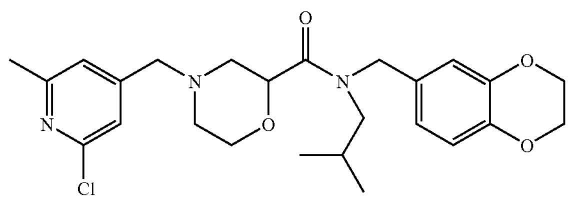 | (±)-4-[(2-chloro-6-methylpyridin-4-yl)methyl]-N-(2,3-dihydro-1,4-benzodioxin-6-ylmethyl)-N-isobutylmorpholine-2-carboxamide | 474.2180 |
| 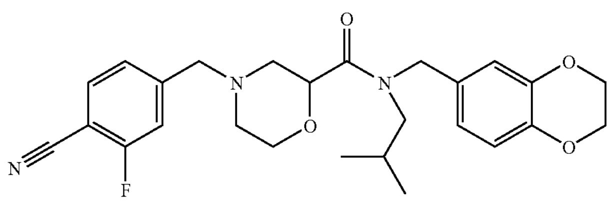 | (±)-4-(4-cyano-3-fluorobenzyl)-N-(2,3-dihydro-1,4-benzodioxin-6-ylmethyl)-N-isobutylmorpholine-2-carboxamide | 468.2291 |
| 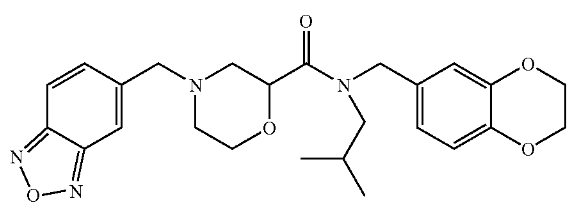 | (±)-4-(2,1,3-benzoxadiazol-5-ylmethyl)-N-(2,3-dihydro-1,4-benzodioxin-6-ylmethyl)-N-isobutylmorpholine-2-carboxamide | 467.2301 |
| 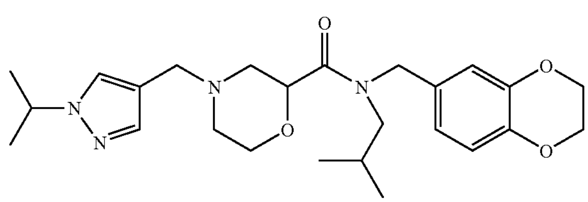 | (±)-N-(2,3-dihydro-1,4-benzodioxin-6-ylmethyl)-N-isobutyl-4-[(1-isopropyl-1H-pyrazol-4-yl)methyl]morpholine-2-carboxamide | 457.2832 |
| 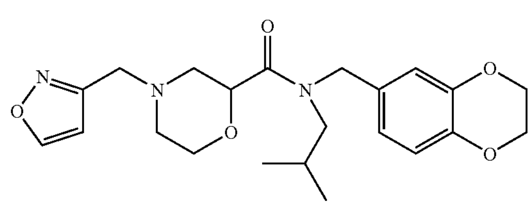 | (±)-N-(2,3-dihydro-1,4-benzodioxin-6-ylmethyl)-N-isobutyl-4-(isoxazol-3-ylmethyl)morpholine-2-carboxamide | 416.2191 |
| 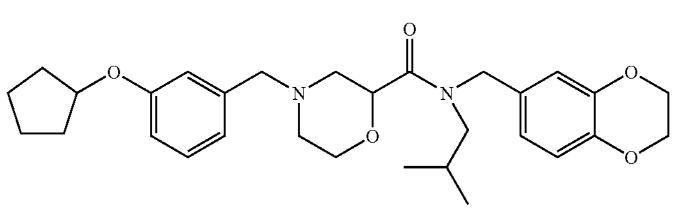 | (±)-4-[3-(cyclopentyloxy)benzyl]-N-(2,3-dihydro-1,4-benzodioxin-6-ylmethyl)-N-isobutylmorpholine-2-carboxamide | 509.3042 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 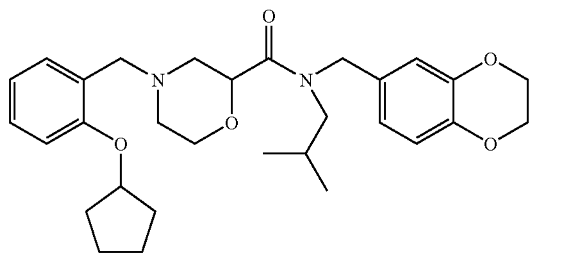 | (±)-4-[2-(cyclopentyloxy)benzyl]-N-(2,3-dihydro-1,4-benzodioxin-6-ylmethyl)-N-isobutylmorpholine-2-carboxamide | 509.3036 |
| 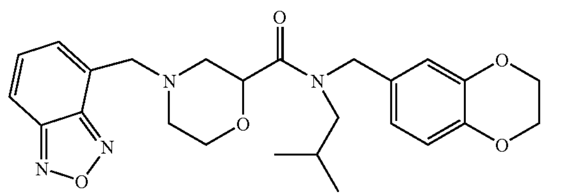 | (±)-4-(2,1,3-benzoxadiazol-4-ylmethyl)-N-(2,3-dihydro-1,4-benzodioxin-6-ylmethyl)-N-isobutylmorpholine-2-carboxamide | 467.2316 |
| 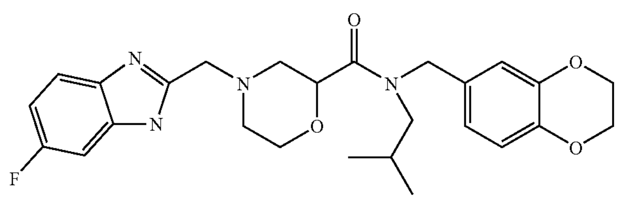 | (±)-N-(2,3-dihydro-1,4-benzodioxin-6-ylmethyl)-4-[(6-fluoro-1H-benzimidazol-2-yl)methyl]-N-isobutylmorpholine-2-carboxamide | 483.2415 |
| 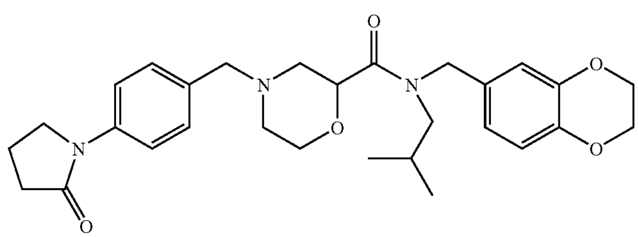 | (±)-N-(2,3-dihydro-1,4-benzodioxin-6-ylmethyl)-N-isobutyl-4-[4-(2-oxopyrrolidin-1-yl)benzyl]morpholine-2-carboxamide | 508.2833 |
| 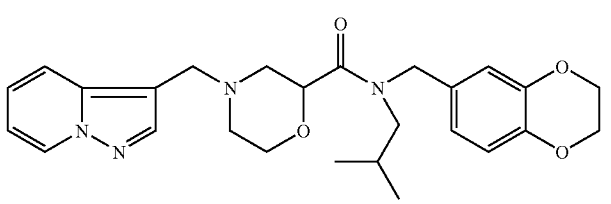 | (±)-N-(2,3-dihydro-1,4-benzodioxin-6-ylmethyl)-N-isobutyl-4-(pyrazolo[1,5-a]pyridin-3-ylmethyl)morpholine-2-carboxamide | 465.2514 |
| 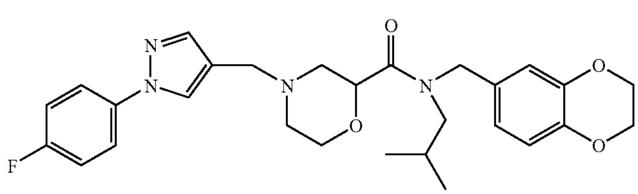 | (±)-N-(2,3-dihydro-1,4-benzodioxin-6-ylmethyl)-4-{[1-(4-fluorophenyl)-1H-pyrazol-4-yl]methyl}-N-isobutylmorpholine-2-carboxamide | 509.2583 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 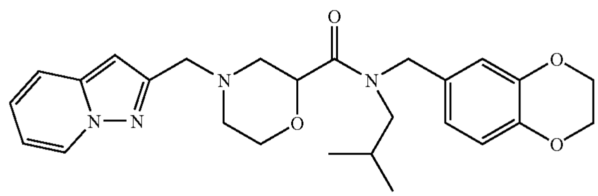 | (±)-N-(2,3-dihydro-1,4-benzodioxin-6-ylmethyl)-N-isobutyl-4-(pyrazolo[1,5-a]pyridin-2-ylmethyl)morpholine-2-carboxamide | 465.2513 |
| | (±)-N-(3,4-dihydro-2H-1,5-benzodioxepin-7-ylmethyl)-N-isobutyl-4-(2-methoxybenzyl)morpholine-2-carboxamide | 469.3 |
| 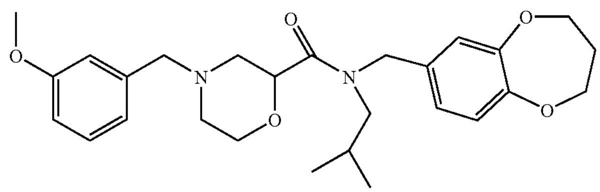 | (±)-N-(3,4-dihydro-2H-1,5-benzodioxepin-7-ylmethyl)-N-isobutyl-4-(3-methoxybenzyl)morpholine-2-carboxamide | 469.3 |
| 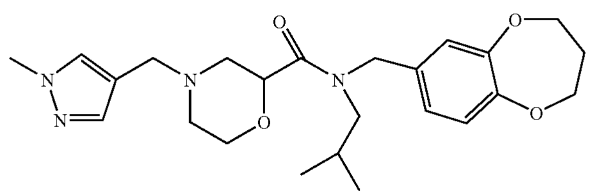 | (±)-N-(3,4-dihydro-2H-1,5-benzodioxepin-7-ylmethyl)-N-isobutyl-4-[(1-methyl-1H-pyrazol-4-yl)methyl]morpholine-2-carboxamide | 443.3 |
| 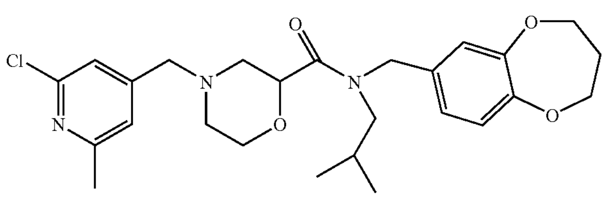 | (±)-4-[(2-chloro-6-methylpyridin-4-yl)methyl]-N-(3,4-dihydro-2H-1,5-benzodioxepin-7-ylmethyl)-N-isobutylmorpholine-2-carboxamide | 490.3 |
| 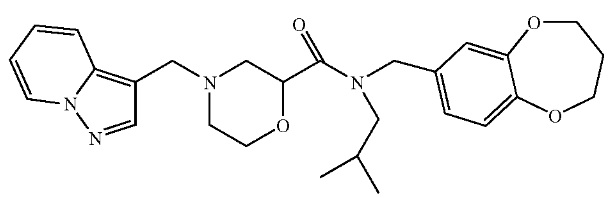 | (±)-N-(3,4-dihydro-2H-1,5-benzodioxepin-7-ylmethyl)-N-isobutyl-4-(pyrazolo[1,5-a]pyridin-3-ylmethyl)morpholine-2-carboxamide | 479.3 |
| 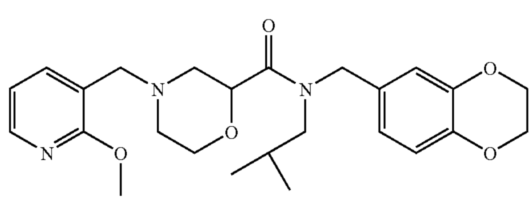 | (±)-N-(2,3-dihydro-1,4-benzodioxin-6-ylmethyl)-N-isobutyl-4-[(2-methoxypyridin-3-yl)methyl]morpholine-2-carboxamide | 456.2498 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 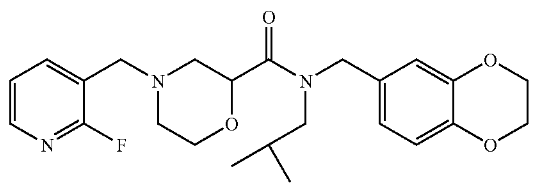 | (±)-N-(2,3-dihydro-1,4-benzodioxin-6-ylmethyl)-4-[(3-fluoropyridin-4-yl)methyl]-N-isobutylmorpholine-2-carboxamide | 444.2305 |
| 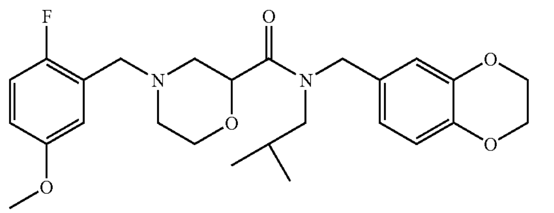 | (±)-N-(2,3-dihydro-1,4-benzodioxin-6-ylmethyl)-4-(2-fluoro-5-methoxybenzyl)-N-isobutylmorpholine-2-carboxamide | 473.2470 |
| 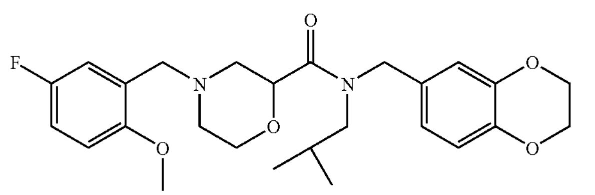 | (±)-N-(2,3-dihydro-1,4-benzodioxin-6-ylmethyl)-4-(5-fluoro-2-methoxybenzyl)-N-isobutylmorpholine-2-carboxamide | 473.2466 |
| 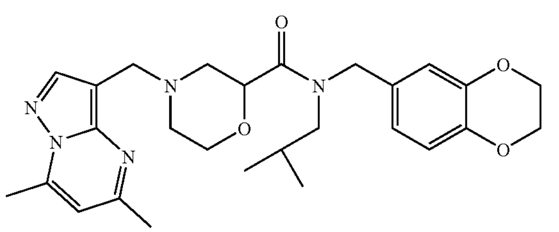 | (±)-N-(2,3-dihydro-1,4-benzodioxin-6-ylmethyl)-4-[(5,7-dimethylpyrazolo[1,5-a]pyrimidin-3-yl)methyl]-N-isobutylmorpholine-2-carboxamide | 494.2782 |
| 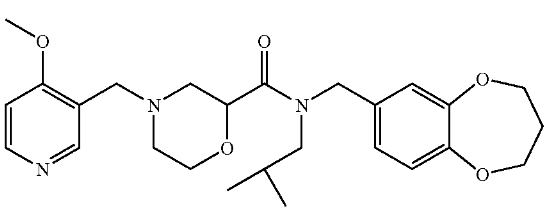 | (±)-N-(3,4-dihydro-2H-1,5-benzodioxepin-7-ylmethyl)-N-isobutyl-4-[(4-methoxypyridin-3-yl)methyl]morpholine-2-carboxamide | 470.3 |
| 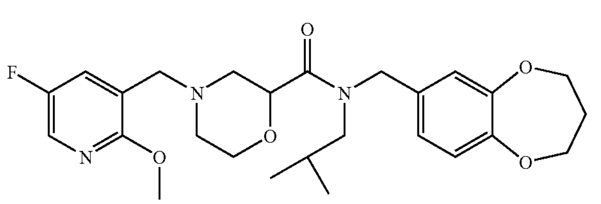 | (±)-N-(3,4-dihydro-2H-1,5-benzodioxepin-7-ylmethyl)-4-[(5-fluoro-2-methoxypyridin-3-yl)methyl]morpholine-2-carboxamide | 488.3 |
| 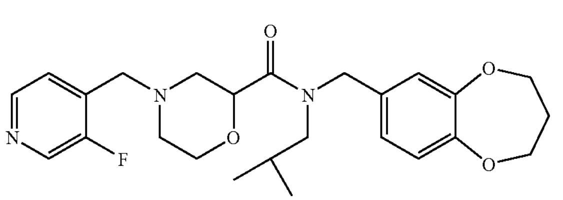 | (±)-N-(3,4-dihydro-2H-1,5-benzodioxepin-7-ylmethyl)-4-[(3-fluoropyridin-4-yl)methyl]-N-isobutylmorpholine-2-carboxamide | 458.2425 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 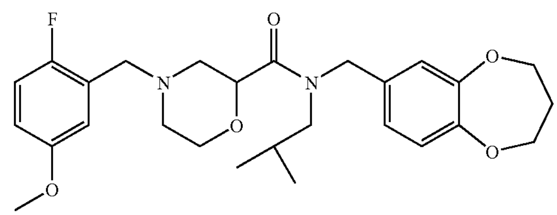 | (±)-N-(3,4-dihydro-2H-1,5-benzodioxepin-7-ylmethyl)-4-(2-fluoro-5-methoxybenzyl)-N-isobutylmorpholine-2-carboxamide | 487.2604 |
| 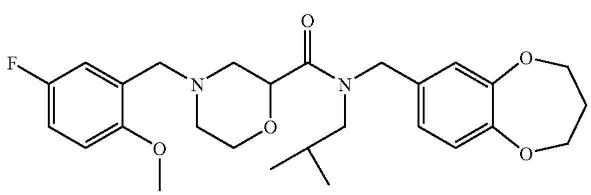 | (±)-N-(3,4-dihydro-2H-1,5-benzodioxepin-7-ylmethyl)-4-(5-fluoro-2-methoxybenzyl)-N-isobutylmorpholine-2-carboxamide | 487.2615 |
| 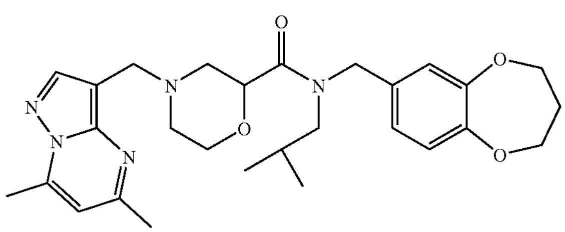 | (±)-N-(3,4-dihydro-2H-1,5-benzodioxepin-7-ylmethyl)-4-[(5,7-dimethylpyrazolo[1,5-a]pyrimidin-3-yl)methyl]-N-isobutylmorpholine-2-carboxamide | 508.2932 |
| 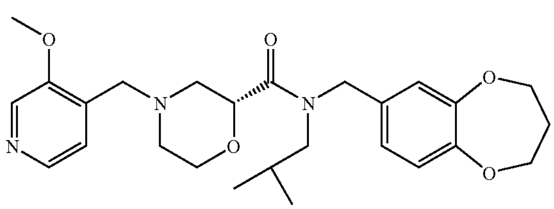 | (−)-(2R)-N-(3,4-dihydro-2H-1,5-benzodioxepin-7-ylmethyl)-N-isobutyl-4-[(3-methoxypyridin-4-yl)methyl]morpholine-2-carboxamide | 470.3 |
| 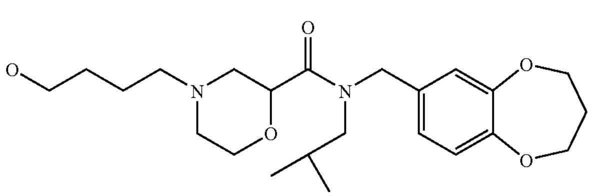 | (±)-N-(3,4-dihydro-2H-1,5-benzodioxepin-7-ylmethyl)-4-(4-hydroxybutyl)-N-isobutylmorpholine-2-carboxamide | 421.3 |
| 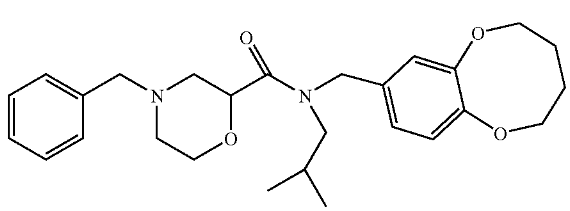 | (±)-4-benzyl-N-isobutyl-N-(2,3,4,5-tetrahydro-1,6-benzodioxocin-8-ylmethyl)morpholine-2-carboxamide | 453.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 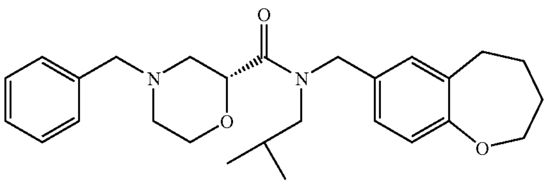 | (−)-(2R)-4-benzyl-N-isobutyl-N-(2,3,4,5-tetrahydro-1-benzoxepin-7-ylmethyl)morpholine-2-carboxamide | 437.4 |
| 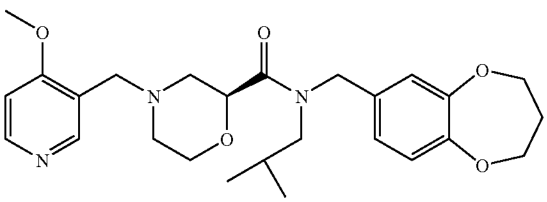 | (+)-(2S)-N-(3,4-dihydro-2H-1,5-benzodioxepin-7-ylmethyl)-N-isobutyl-4-[(4-methoxypyridin-3-yl)methyl]morpholine-2-carboxamide | 470.3 |
| 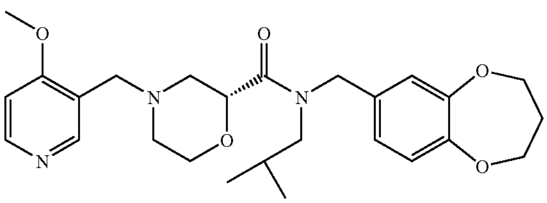 | (−)-(2R)-N-(3,4-dihydro-2H-1,5-benzodioxepin-7-ylmethyl)-N-isobutyl-4-[(4-methoxypyridin-3-yl)methyl]morpholine-2-carboxamide | 470.3 |
| 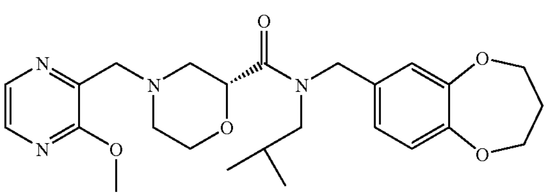 | (−)-(2R)-N-(3,4-dihydro-2H-1,5-benzodioxepin-7-ylmethyl)-N-isobutyl-4-[(3-methoxypyrazin-2-yl)methyl]morpholine-2-carboxamide | 471.3 |
| 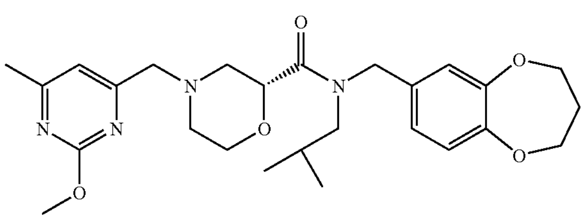 | (−)-(2R)-N-(3,4-dihydro-2H-1,5-benzodioxepin-7-ylmethyl)-N-isobutyl-4-[(2-methoxy-6-methylpyrimidin-4-yl)methyl]morpholine-2-carboxamide | 485.3 |
| 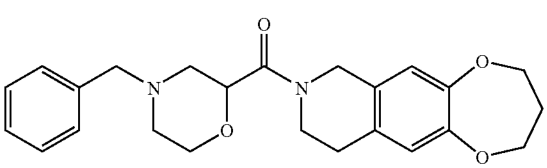 | (±)-8-[(4-benzylmorpholin-2-yl)carbonyl]-3,4,7,8,9,10-hexahydro-2H-[1,4]dioxepino[2,3-g]isoquinoline | 409.3 |
| 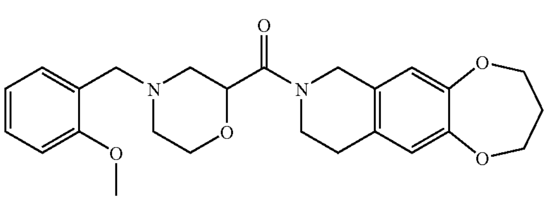 | (±)-8-{[4-(2-methoxybenzyl)morpholin-2-yl]carbonyl}-3,4,7,8,9,10-hexahydro-2H-[1,4]dioxepino[2,3-g]isoquinoline | 439.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 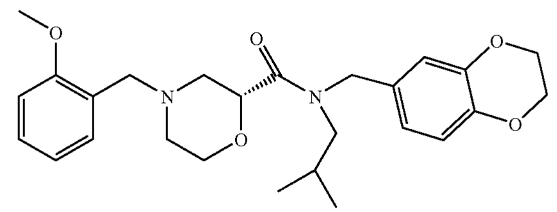 | (−)-(2R)-N-(2,3-dihydro-1,4-benzodioxin-6-ylmethyl)-N-isobutyl-4-(2-methoxybenzyl)morpholine-2-carboxamide | 455.3 |
| 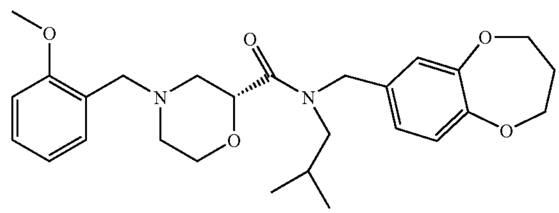 | (−)-(2R)-N-(3,4-dihydro-2H-1,5-benzodioxepin-7-ylmethyl)-N-isobutyl-4-(2-methoxybenzyl)morpholine-2-carboxamide | 469.3 |
| 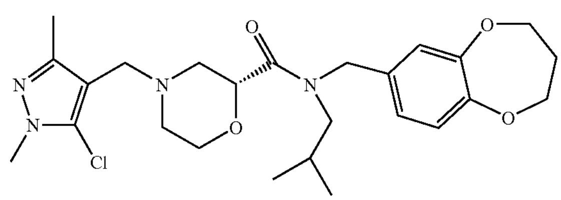 | (−)-(2R)-4-[(5-chloro-1,3-dimethyl-1H-pyrazol-4-yl)methyl]-N-(3,4-dihydro-2H-1,5-benzodioxepin-7-ylmethyl)-N-isobutylmorpholine-2-carboxamide | 493.3 |
| 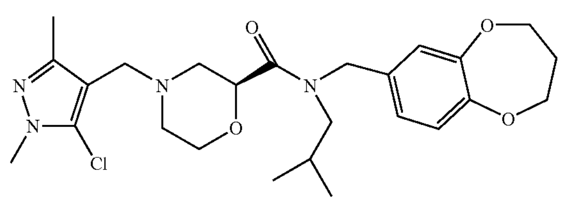 | (+)-2S)-4-[(5-chloro-1,3-dimethyl-1H-pyrazol-4-yl)methyl]-N-(3,4-dihydro-2H-1,5-benzodioxepin-7-ylmethyl)-N-isobutylmorpholine-2-carboxamide | 493.3 |
| 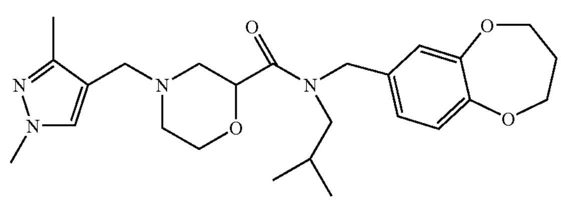 | (±)-N-(3,4-dihydro-2H-1,5-benzodioxepin-7-ylmethyl)-4-[(1,3-dimethyl-1H-pyrazol-4-yl)methyl]-N-isobutylmorpholine-2-carboxamide | 457.3 |
| 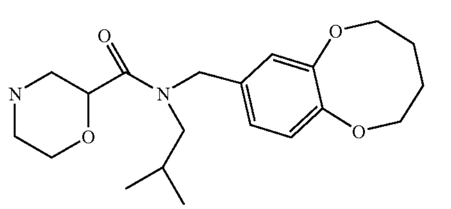 | (±)-N-isobutyl-N-(2,3,4,5-tetrahydro-1,6-benzodioxocin-8-ylmethyl)morpholine-2-carboxamide | 363.3 |
| 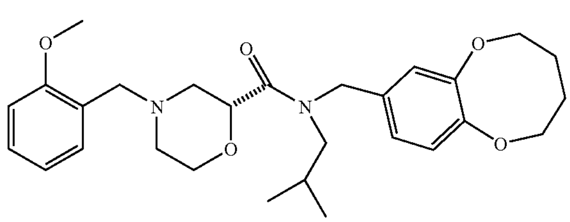 | (±)-N-isobutyl-4-(2-methoxybenzyl)-N-(2,3,4,5-tetrahydro-1,6-benzodioxocin-8-ylmethyl)morpholine-2-carboxamide | 483.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 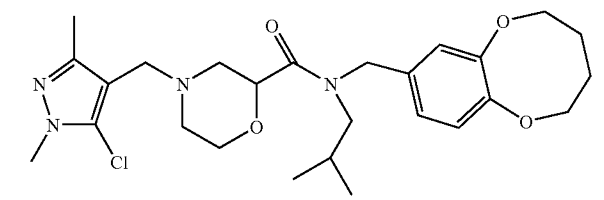 | (±)-4-[(5-chloro-1,3-dimethyl-1H-pyrazol-4-yl)methyl]-N-isobutyl-N-(2,3,4,5-tetrahydro-1,6-benzodioxocin-8-ylmethyl)morpholine-2-carboxamide | 507.3 |
| 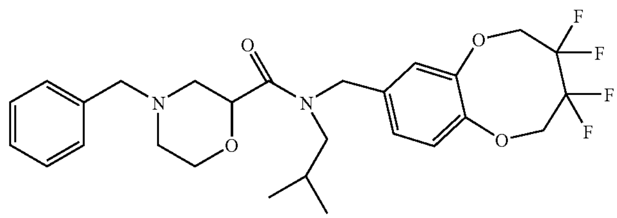 | (±)-4-benzyl-N-isobutyl-N-[(3,3,4,4-tetrafluoro-2,3,4,5-tetrahydro-1,6-benzodioxocin-8-yl)methyl]morpholine-2-carboxamide | 525.3 |
| 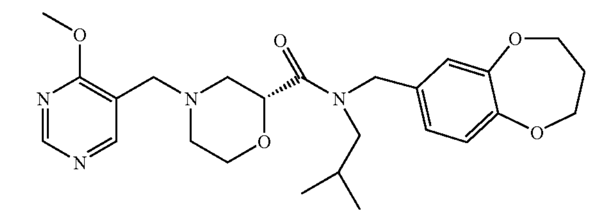 | (−)-(2R)-N-(3,4-dihydro-2H-1,5-benzodioxepin-7-ylmethyl)-N-isobutyl-4-[(4-methoxypyrimidin-5-yl)methyl]morpholine-2-carboxamide | 471.3 |
| 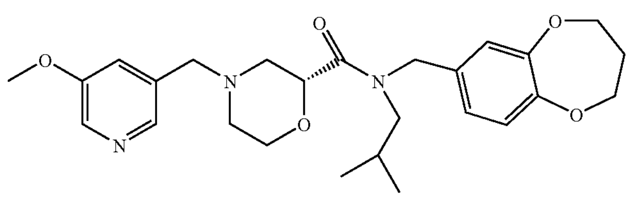 | (−)-(2R)-N-(3,4-dihydro-2H-1,5-benzodioxepin-7-ylmethyl)-N-isobutyl-4-[(5-methoxypyridin-3-yl)methyl]morpholine-2-carboxamide | 470.3 |
| 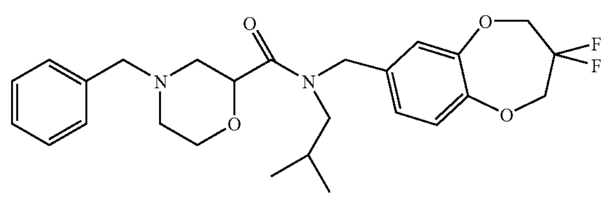 | (±)-4-benzyl-N-[(3,3-difluoro-3,4-dihydro-2H-1,5-benzodioxepin-7-yl)methyl]-N-isobutylmorpholine-2-carboxamide | 475.3 |
| 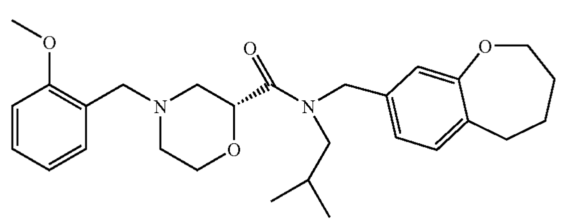 | (−)--N-isobutyl-4-(2-methoxybenzyl)-N-(2,3,4,5-tetrahydro-1-benzoxepin-8-ylmethyl)morpholine-2-carboxamide | 467.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 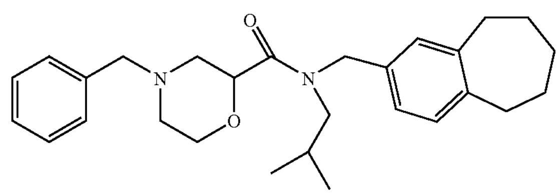 | (±)-4-benzyl-N-isobutyl-N-(6,7,8,9-tetrahydro-5H-benzo[7]annulen-2-ylmethyl)morpholine-2-carboxamide | 435.3 |
| 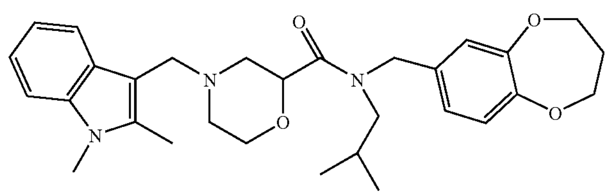 | (±)-N-(3,4-dihydro-2H-1,5-benzodioxepin-7-ylmethyl)-4-[(1,2-dimethyl-1H-indol-3-yl)methyl]-N-isobutylmorpholine-2-carboxamide | 506.3 |
| 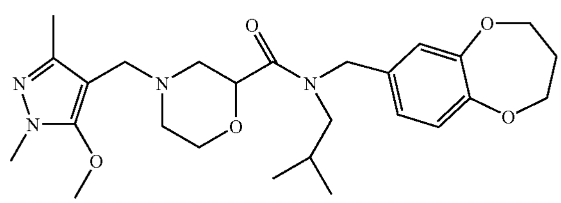 | (±)-N-(3,4-dihydro-2H-1,5-benzodioxepin-7-ylmethyl)-N-isobutyl-4-[(5-methoxy-1,3-dimethyl-1H-pyrazol-4-yl)methyl]morpholine-2-carboxamide | 487.3 |
| 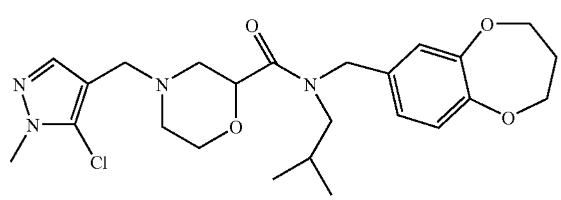 | (±)-4-[(5-chloro-1-methyl-1H-pyrazol-4-yl)methyl]-N-(3,4-dihydro-2H-1,5-benzodioxepin-7-ylmethyl)-N-isobutylmorpholine-2-carboxamide | 479.2 |
| | (±)-N-(3,4-dihydro-2H-1,5-benzodioxepin-7-ylmethyl)-N-isobutyl-4-{2-[(trifluoromethyl)thio]benzyl}morpholine-2-carboxamide | 539.2 |
| 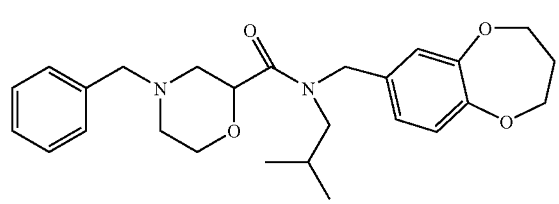 | (±)-4-benzyl-N-isobutyl-N-(2,3,4,5-tetrahydro-1-benzoxepin-8-ylmethyl)morpholine-2-carboxamide | 437.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 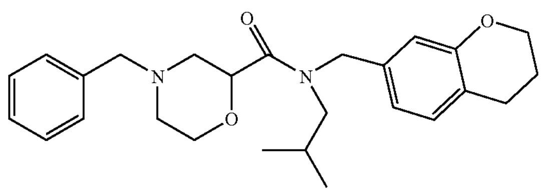 | (±)-4-benzyl-N-(3,4-dihydro-2H-chromen-7-ylmethyl)-N-isobutylmorpholine-2-carboxamide | 423.3 |
| 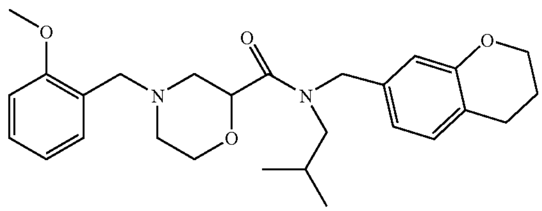 | (±)-N-(3,4-dihydro-2H-chromen-7-ylmethyl)-N-isobutyl-4-(2-methoxybenzyl)morpholine-2-carboxamide | 453.3 |
| 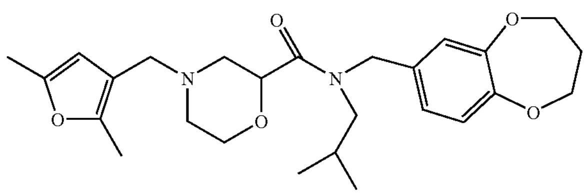 | (±)-N-(3,4-dihydro-2H-1,5-benzodioxepin-7-ylmethyl)-4-[(2,5-dimethyl-3-furyl)methyl]-N-isobutylmorpholine-2-carboxamide | 457.3 |
| 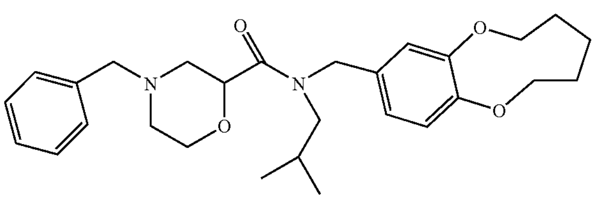 | (±)-N-(2-methylpropyl)-4-(phenylmethyl)-N-[(3,4,5,6-tetrahydro-2H-1,7-benzodioxonin-9-yl)methyl]morpholine-2-carboxamide | 467.3 |
| 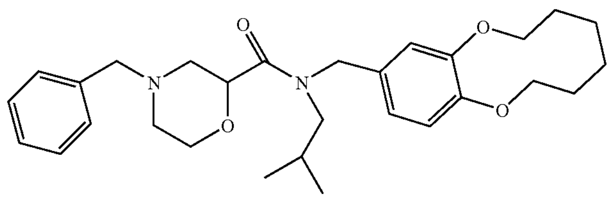 | (±)-4-benzyl-N-(2,3,4,5,6,7-hexahydro-1,8-benzodioxecin-10-ylmethyl)-N-isobutylmorpholine-2-carboxamide | 481.3 |
| 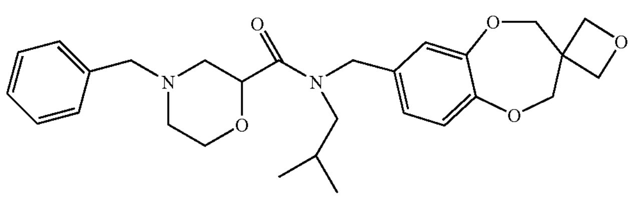 | (±)-4-benzyl-N-isobutyl-N-(spiro[1,5-benzodioxepine-3,3'-oxetan]-7-ylmethyl)morpholine-2-carboxamide | 481.3 |
| 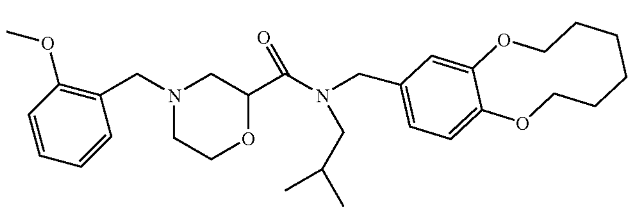 | (±)-N-(2,3,4,5,6,7-hexahydro-1,8-benzodioxecin-10-ylmethyl)-N-isobutyl-4-(2-methoxybenzyl)morpholine-2-carboxamide | 511.4 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 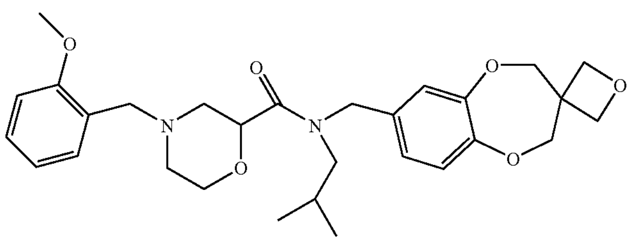 | (±)-N-isobutyl-4-(2-methoxybenzyl)-N-(spiro[1,5-benzodioxepine-3,3'-oxetan]-7-ylmethyl)morpholine-2-carboxamide | 511.3 |
| 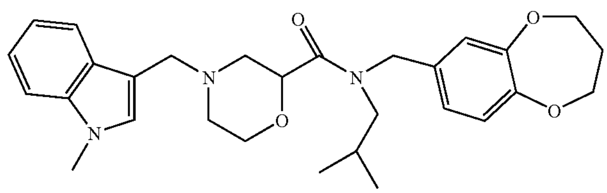 | (±)-N-(3,4-dihydro-2H-1,5-benzodioxepin-7-ylmethyl)-N-isobutyl-4-[(1-methyl-1H-indol-3-yl)methyl]morpholine-2-carboxamide | 492.3 |
| 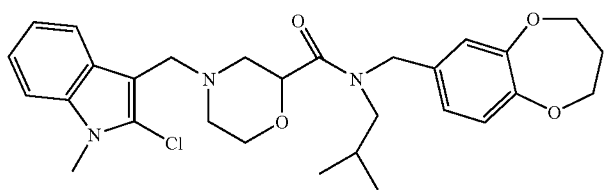 | (±)-4-[(2-chloro-1-methyl-1H-indol-3-yl)methyl]-N-(3,4-dihydro-2H-1,5-benzodioxepin-7-ylmethyl)-N-isobutylmorpholine-2-carboxamide | 526.3 |
| 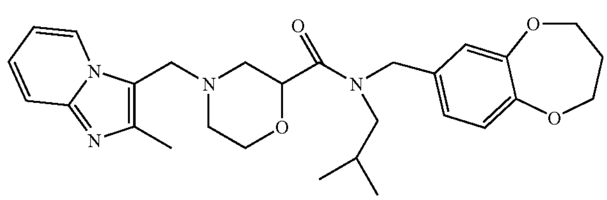 | (±)-N-(3,4-dihydro-2H-1,5-benzodioxepin-7-ylmethyl)-N-isobutyl-4-[(2-methylimidazo[1,2-a]pyridin-3-yl)methyl]morpholine-2-carboxamide | 493.3 |
| 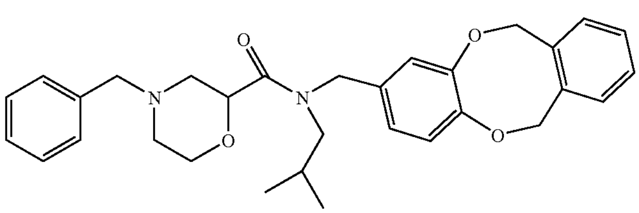 | (±)-4-benzyl-N-(6,11-dihydrodibenzo[b,f][1,4]dioxocin-2-ylmethyl)-N-isobutylmorpholine-2-carboxamide | 501.3 |
| 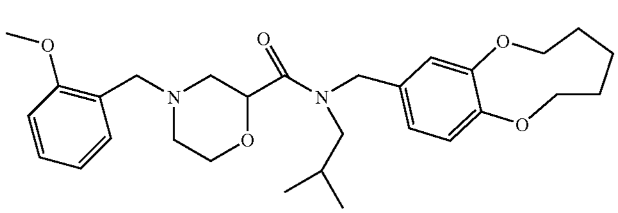 | (±)-N-isobutyl-4-(2-methoxybenzyl)-N-(3,4,5,6-tetrahydro-2H-1,7-benzodioxonin-9-ylmethyl)morpholine-2-carboxamide | 497.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 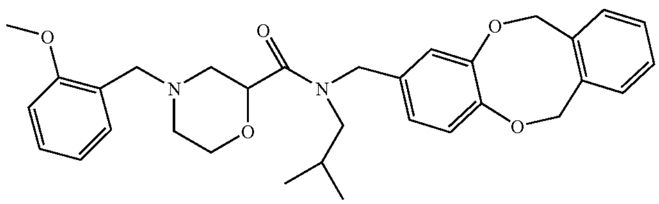 | (±)-N-(6,11-dihydrodibenzo[b,f][1,4]dioxocin-2-ylmethyl)-N-isobutyl-4-(2-methoxybenzyl)morpholine-2-carboxamide | 531.3 |
| 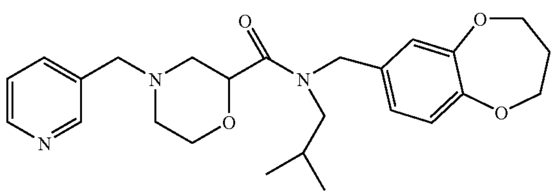 | (±)-N-(3,4-dihydro-2H-1,5-benzodioxepin-7-ylmethyl)-N-isobutyl-4-(pyridin-3-ylmethyl)morpholine-2-carboxamide | 440.2525 |
| 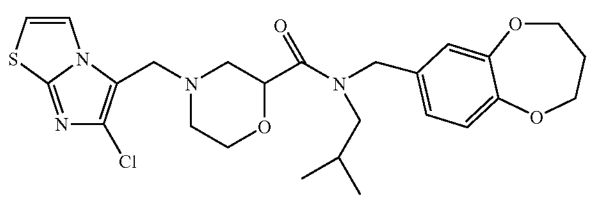 | (±)-4-[(6-chloroimidazo[2,1-b][1,3]thiazol-5-yl)methyl]-N-(3,4-dihydro-2H-1,5-benzodioxepin-7-ylmethyl)-N-isobutylmorpholine-2-carboxamide | 519.1828 |
| 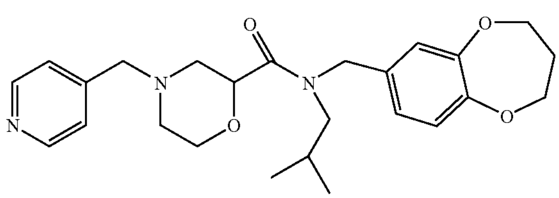 | (±)-N-(3,4-dihydro-2H-1,5-benzodioxepin-7-ylmethyl)-N-isobutyl-4-(pyridin-4-ylmethyl)morpholine-2-carboxamide | 440.2514 |
| 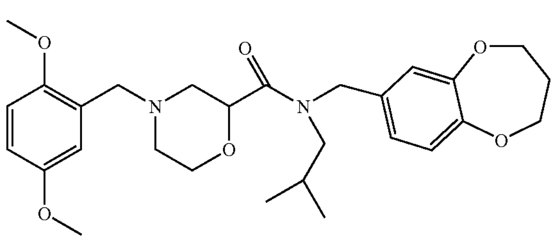 | (±)-N-(3,4-dihydro-2H-1,5-benzodioxepin-7-ylmethyl)-4-(2,5-dimethoxybenzyl)-N-isobutylmorpholine-2-carboxamide | 499.2808 |
| 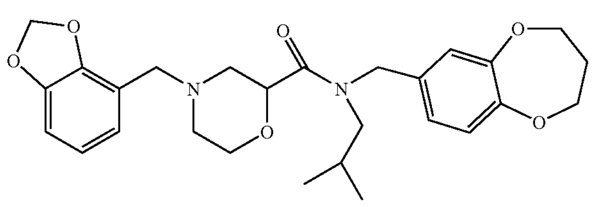 | (±)-4-(1,3-benzodioxol-4-ylmethyl)-N-(3,4-dihydro-2H-1,5-benzodioxepin-7-ylmethyl)-N-isobutylmorpholine-2-carboxamide | 483.2475 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 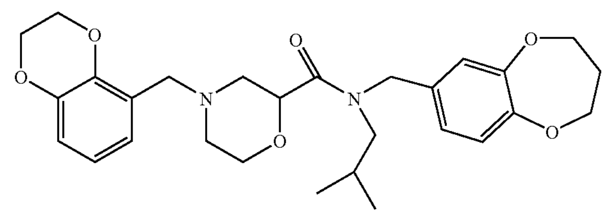 | (±)-N-(3,4-dihydro-2H-1,5-benzodioxepin-7-ylmethyl)-4-(2,3-dihydro-1,4-benzodioxin-5-ylmethyl)-N-isobutylmorpholine-2-carboxamide | 497.2641 |
| 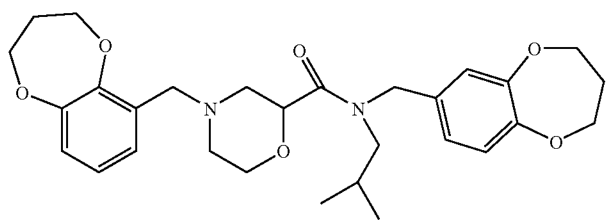 | (±)-4-(3,4-dihydro-2H-1,5-benzodioxepin-6-ylmethyl)-N-(3,4-dihydro-2H-1,5-benzodioxepin-7-ylmethyl)-N-isobutylmorpholine-2-carboxamide | 511.2800 |
| 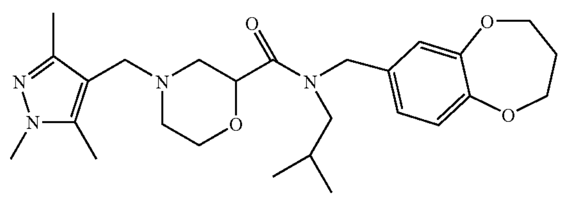 | (±)-N-(3,4-dihydro-2H-1,5-benzodioxepin-7-ylmethyl)-N-isobutyl-4-[(1,3,5-trimethyl-1H-pyrazol-4-yl)methyl]morpholine-2-carboxamide | 471.2956 |
| 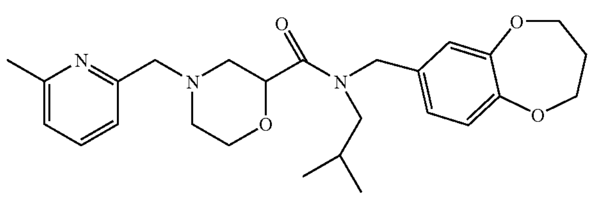 | (±)-N-(3,4-dihydro-2H-1,5-benzodioxepin-7-ylmethyl)-N-isobutyl-4-[(6-methylpyridin-2-yl)methyl]morpholine-2-carboxamide | 454.2682 |
| 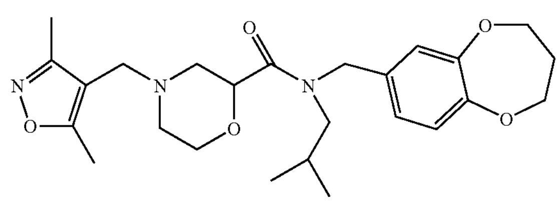 | (±)-N-(3,4-dihydro-2H-1,5-benzodioxepin-7-ylmethyl)-4-[(3,5-dimethylisoxazol-4-yl)methyl]-N-isobutylmorpholine-2-carboxamide | 458.2624 |
| 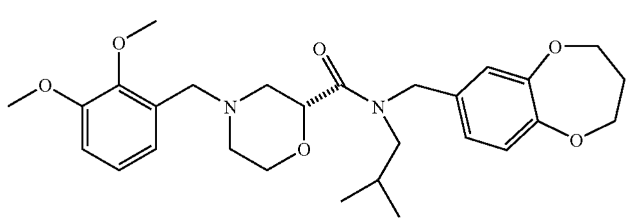 | (±)-N-(3,4-dihydro-2H-1,5-benzodioxepin-7-ylmethyl)-4-(2,3-dimethoxybenzyl)-N-isobutylmorpholine-2-carboxamide | 499.2803 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 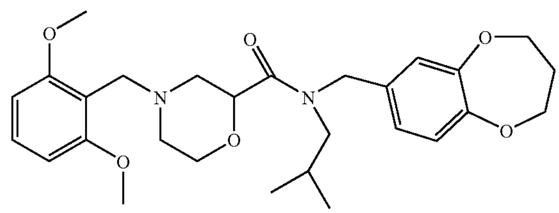 | (±)-N-(3,4-dihydro-2H-1,5-benzodioxepin-7-ylmethyl)-4-(2,6-dimethoxybenzyl)-N-isobutylmorpholine-2-carboxamide | 499.2804 |
| 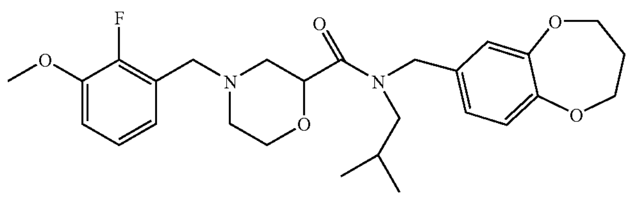 | (±)-N-(3,4-dihydro-2H-1,5-benzodioxepin-7-ylmethyl)-4-(2-fluoro-3-methoxybenzyl)-N-isobutylmorpholine-2-carboxamide | 487.2587 |
| 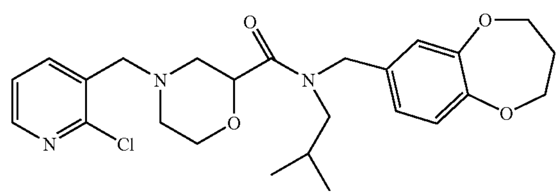 | (±)-4-[(2-chloropyridin-3-yl)methyl]-N-(3,4-dihydro-2H-1,5-benzodioxepin-7-ylmethyl)-N-isobutylmorpholine-2-carboxamide | 474.2125 |
| 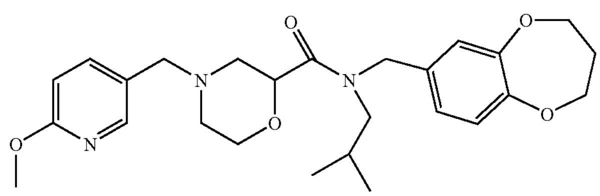 | (±)-N-(3,4-dihydro-2H-1,5-benzodioxepin-7-ylmethyl)-N-isobutyl-4-[(6-methoxypyridin-3-yl)methyl]morpholine-2-carboxamide | 470.2616 |
| 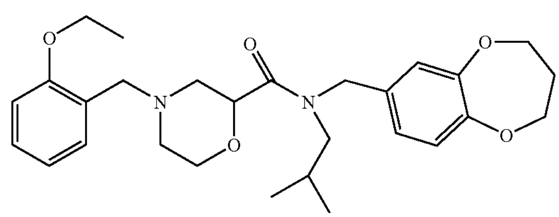 | (±)-N-(3,4-dihydro-2H-1,5-benzodioxepin-7-ylmethyl)-4-(2-ethoxybenzyl)-N-isobutylmorpholine-2-carboxamide | 483.2852 |
| 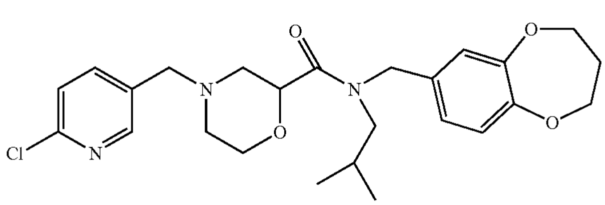 | (±)-4-[(6-chloropyridin-3-yl)methyl]-N-(3,4-dihydro-2H-1,5-benzodioxepin-7-ylmethyl)-N-isobutylmorpholine-2-carboxamide | 474.2157 |
| 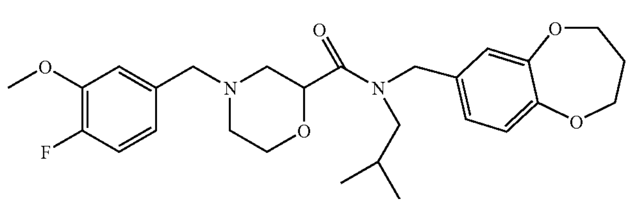 | (±)-N-(3,4-dihydro-2H-1,5-benzodioxepin-7-ylmethyl)-4-(4-fluoro-3-methoxybenzyl)-N-isobutylmorpholine-2-carboxamide | 487.2567 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 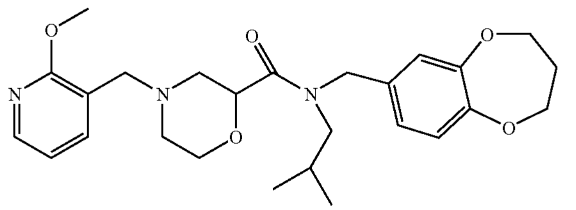 | (±)-N-(3,4-dihydro-2H-1,5-benzodioxepin-7-ylmethyl)-N-isobutyl-4-[(2-methoxypyridin-3-yl)methyl]morpholine-2-carboxamide | 470.2644 |
| 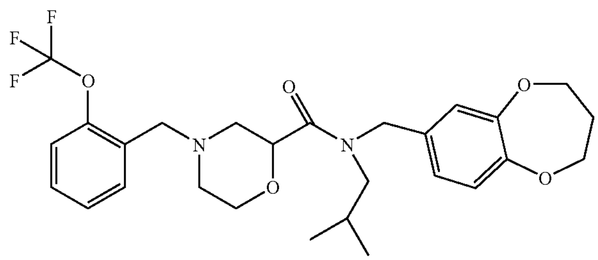 | (±)-N-(3,4-dihydro-2H-1,5-benzodioxepin-7-ylmethyl)-N-isobutyl-4-[2-(trifluoromethoxy)benzyl]morpholine-2-carboxamide | 523.2415 |
| 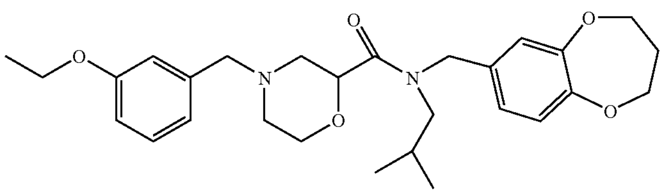 | (±)-N-(3,4-dihydro-2H-1,5-benzodioxepin-7-ylmethyl)-4-(3-ethoxybenzyl)-N-isobutylmorpholine-2-carboxamide | 483.2837 |
| 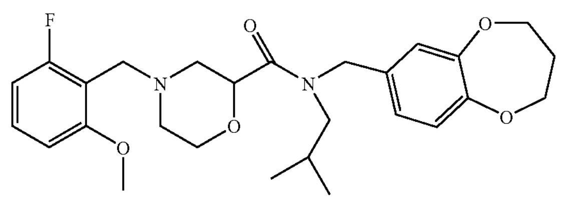 | (±)-N-(3,4-dihydro-2H-1,5-benzodioxepin-7-ylmethyl)-4-(2-fluoro-6-methoxybenzyl)-N-isobutylmorpholine-2-carboxamide | 487.2599 |
| 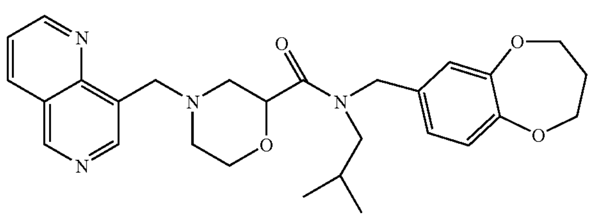 | (±)-N-(3,4-dihydro-2H-1,5-benzodioxepin-7-ylmethyl)-N-isobutyl-4-(1,6-naphthyridin-8-ylmethyl)morpholine-2-carboxamide | 491.3 |
| 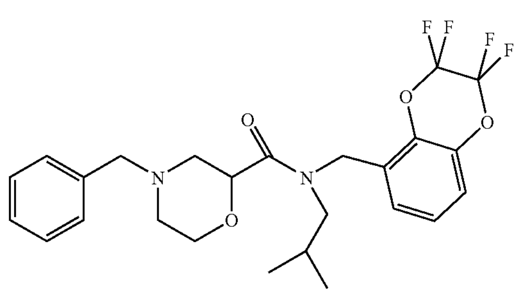 | (±)-4-benzyl-N-isobutyl-N-[(2,2,3,3-tetrafluoro-2,3-dihydro-1,4-benzidioxin-5-yl)methyl]morpholine-2-carboxamide | 497.2 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 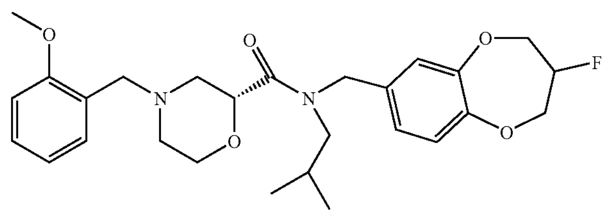 | (2R)-N-[(3-fluoro-3,4-dihydro-2H-1,5-benzodioxepin-7-yl)methyl]-N-isobutyl-4-(2-methoxybenzyl)morpholine-2-carboxamide | 487.3 |
| 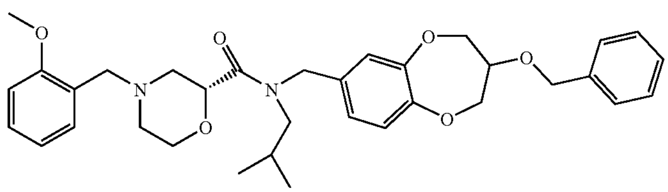 | (2R)-N-{[3-(benzyloxy)-3,4-dihydro-2H-1,5-benzodioxepin-7-yl]methyl}-N-isobutyl-4-(2-methoxybenzyl)morpholine-2-carboxamide | 575.4 |
| 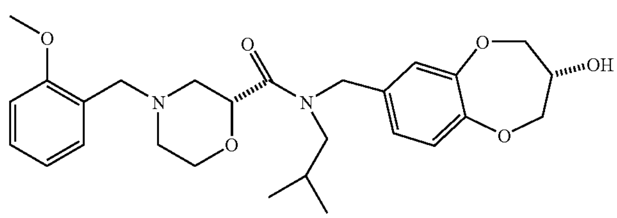 | (2R)-N-{[(3R)-3-hydroxy-3,4-dihydro-2H-1,5-benzodioxepin-7-yl]methyl}-N-isobutyl-4-(2-methoxybenzyl)morpholine-2-carboxamide | 485.3 |
| 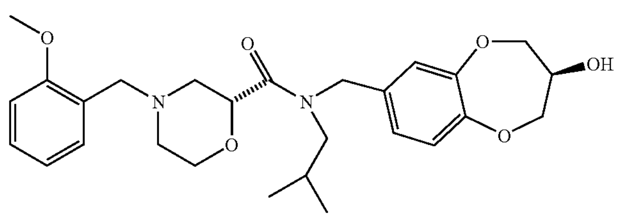 | (2R)-N-{[(3S)-3-hydroxy-3,4-dihydro-2H-1,5-benzodioxepin-7-yl]methyl}-N-isobutyl-4-(2-methoxybenzyl)morpholine-2-carboxamide | 485.3 |
| 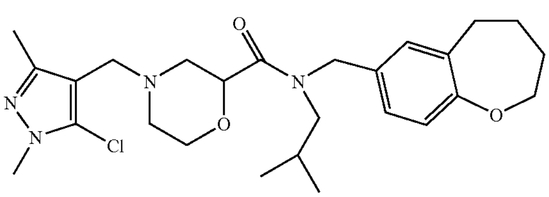 | (±)-4-[(5-chloro-1,3-dimethyl-1H-pyrazol-4-yl)methyl]-N-isobutyl-N-(2,3,4,5-tetrahydro-1-benzoxepin-7-ylmethyl)morpholine-2-carboxamide | 490.3 |
| 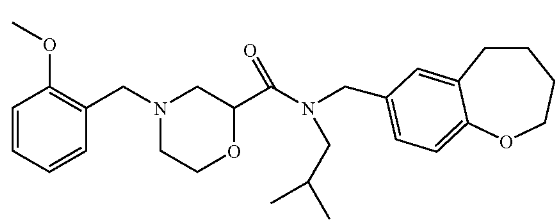 | (±)-N-isobutyl-4-(2-methoxybenzyl)-N-(2,3,4,5-tetrahydro-1-benzoxepin-7-ylmethyl)morpholine-2-carboxamide | 467.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 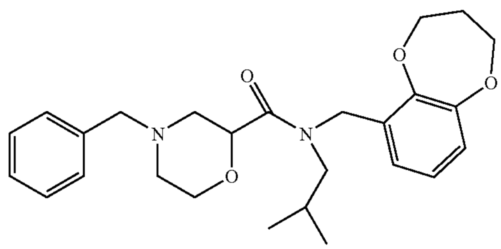 | (±)-4-benzyl-N-(3,4-dihydro-2H-1,5-benzodioxepin-6-ylmethyl)-N-isobutylmorpholine-2-carboxamide | 439.3 |
| 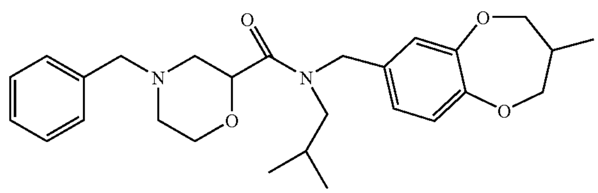 | (±)-4-benzyl-N-isobutyl-N-[(3-methyl-3,4-dihydro-2H-1,5-benzodioxepin-7-yl)methyl]morpholine-2-carboxamide | 453.3 |
| 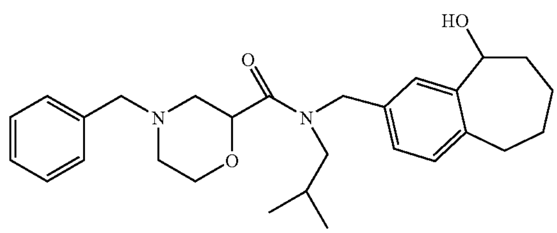 | (±)-4-benzyl-N-[(9-hydroxy-6,7,8,9-tetrahydro-5H-benzo[7]annulen-2-yl)methyl]-N-isobutylmorpholine-2-carboxamide | 451.4 |
| 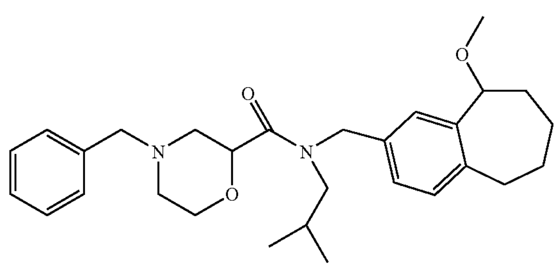 | (±)-4-benzyl-N-isobutyl-N-[(9-methoxy-6,7,8,9-tetrahydro-5H-benzo[7]annulen-2-yl)methyl]morpholine-2-carboxamide | 465.4 |
| 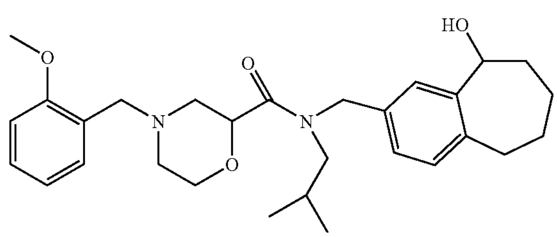 | (±)-N-[(9-hydroxy-6,7,8,9-tetrahydro-5H-benzo[7]annulen-2-yl)methyl]-N-isobutyl-4-(2-methoxybenzyl)morpholine-2-carboxamide | 481.3 |
| 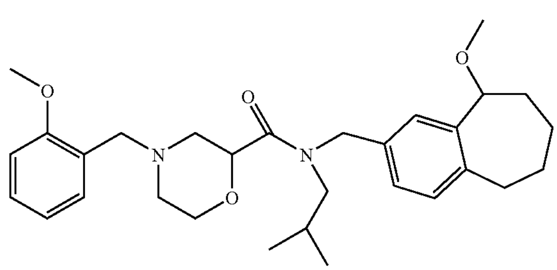 | (±)-N-isobutyl-4-(2-methoxybenzyl)-N-[(9-methoxy-6,7,8,9-tetrahydro-5H-benzo[7]annulen-2-yl)methyl]morpholine-2-carboxamide | 495.4 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 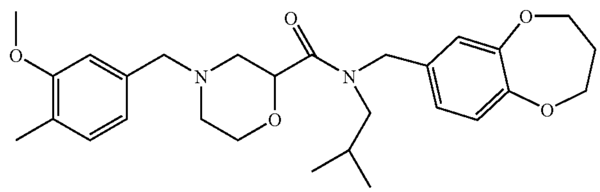 | (±)-N-(3,4-dihydro-2H-1,5-benzodioxepin-7-ylmethyl)-N-isobutyl-4-(3-methoxy-4-methylbenzyl)morpholine-2-carboxamide | 483.2867 |
| 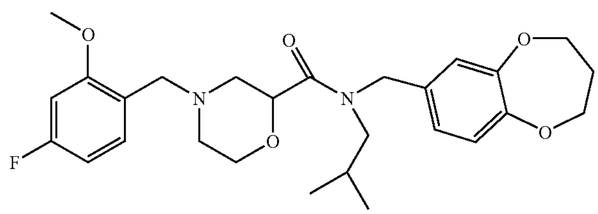 | (±)-N-(3,4-dihydro-2H-1,5-benzodioxepin-7-ylmethyl)-4-(4-fluoro-2-methoxybenzyl)-N-isobutylmorpholine-2-carboxamide | 487.2603 |
| 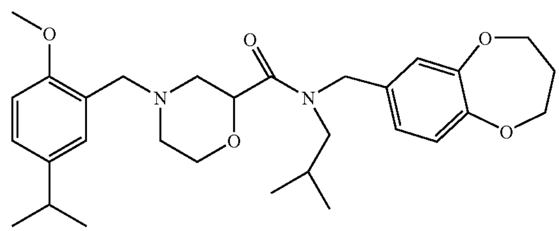 | (±)-N-(3,4-dihydro-2H-1,5-benzodioxepin-7-ylmethyl)-N-isobutyl-4-(5-isopropyl-2-methoxybenzyl)morpholine-2-carboxamide | 511.3167 |
| 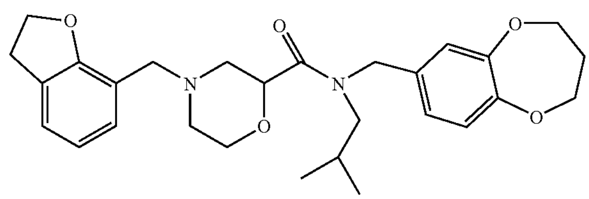 | (±)-N-(3,4-dihydro-2H-1,5-benzodioxepin-7-ylmethyl)-4-(2,3-dihydro-1-benzofuran-7-ylmethyl)-N-isobutylmorpholine-2-carboxamide | 481.2707 |
| 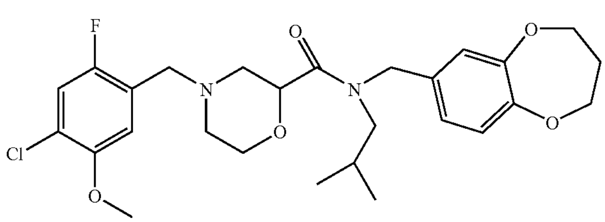 | (±)-4-(34-chloro-2-fluoro-5-methoxybenzyl)-N-(3,4-dihydro-2H-1,5-benzodioxepin-7-ylmethyl)-N-isobutylmorpholine-2-carboxamide | 521.2237 |
| 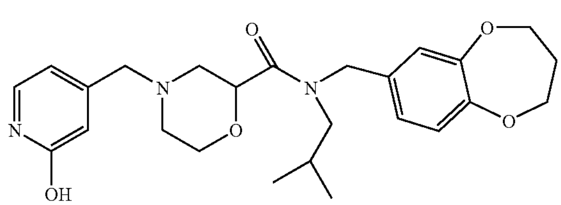 | (±)-N-(3,4-dihydro-2H-1,5-benzodioxepin-7-ylmethyl)-4-[(2-hydroxypyridin-4-yl)methyl]-N-isobutylmorpholine-2-carboxamide | 456.2493 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 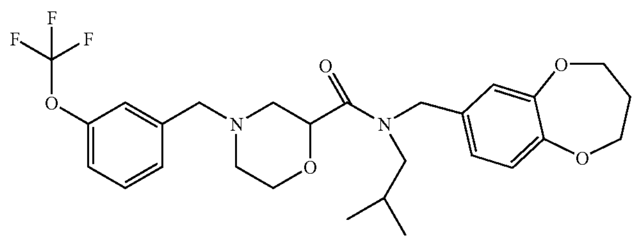 | (±)-N-(3,4-dihydro-2H-1,5-benzodioxepin-7-ylmethyl)-N-isobutyl-4-[3-(trifluoromethoxy)benzyl]morpholine-2-carboxamide | 523.2415 |
| 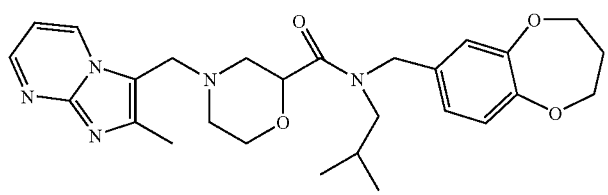 | (±)-N-(3,4-dihydro-2H-1,5-benzodioxepin-7-ylmethyl)-N-isobutyl-4-[(2-methylimidazo[1,2-a]pyrimidin-3-yl)methyl]morpholine-2-carboxamide | 494.2762 |
| 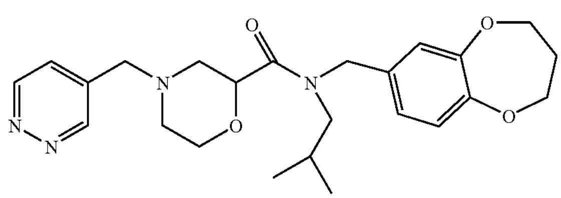 | (±)-N-(3,4-dihydro-2H-1,5-benzodioxepin-7-ylmethyl)-N-isobutyl-4-(pyridazin-4-ylmethyl)morpholine-2-carboxamide | 441.3 |
| 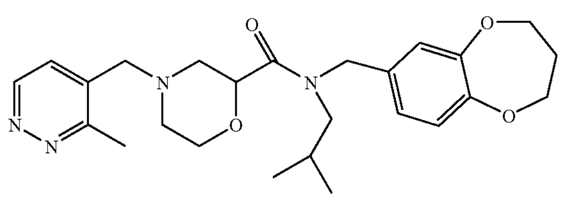 | (±)-N-(3,4-dihydro-2H-1,5-benzodioxepin-7-ylmethyl)-N-isobutyl-4-[(3-methylpyridazin-4-yl)methyl]morpholine-2-carboxamide | 455.5 |
| 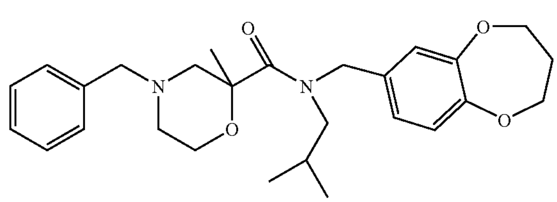 | (±)-4-benzyl-N-(3,4-dihydro-2H-1,5-benzodioxepin-7-ylmethyl)-N-isobutyl-2-methylmorpholine-2-carboxamide | 453.2 |
| 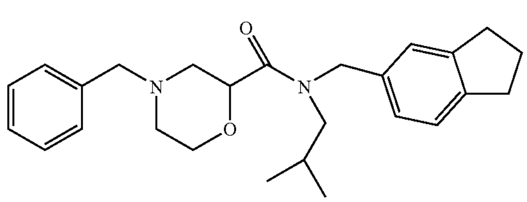 | (±)-4-benzyl-N-(2,3-dihydro-1H-inden-5-ylmethyl)-N-isobutylmorpholine-2-carboxamide | 407.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 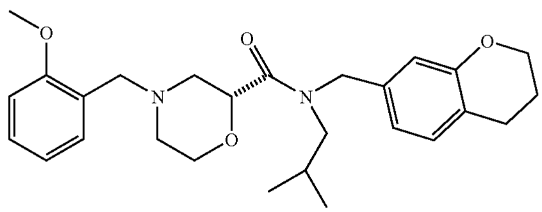 | (−)-(2R)-N-(3,4-dihydro-2H-chromen-7-ylmethyl)-N-isobutyl-4-(2-methoxybenzyl)morpholine-2-carboxamide | 453.3 |
| 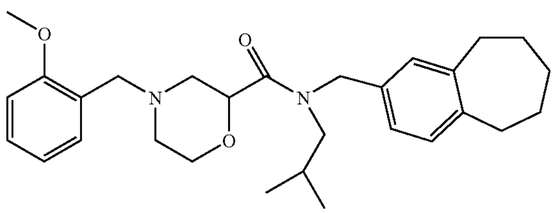 | (±)-N-isobutyl-4-(2-methoxybenzyl)-N-(6,7,8,9-tetrahydro-5H-benzo[7]annulen-2-ylmethyl)morpholine-2-carboxamide | 465.3 |
| 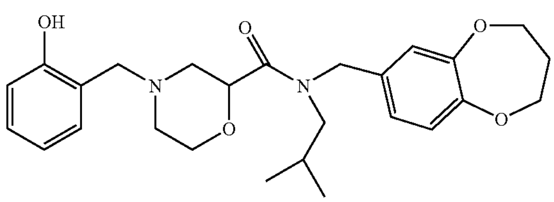 | (±)-N-(3,4-dihydro-2H-1,5-benzodioxepin-7-ylmethyl)-4-(2-hydroxybenzyl)-N-isobutylmorpholine-2-carboxamide | 423.3 |
| 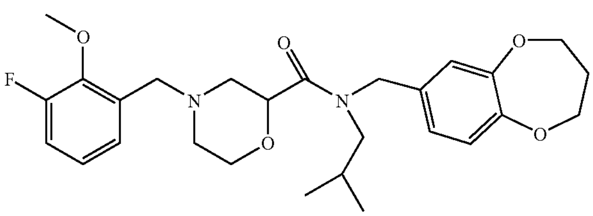 | (±)-N-(3,4-dihydro-2H-1,5-benzodioxepin-7-ylmethyl)-4-(3-fluoro-2-methoxybenzyl)-N-isobutylmorpholine-2-carboxamide | 487.3 |
| 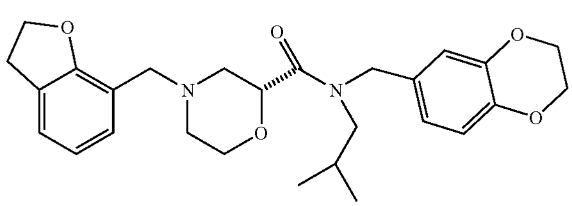 | (−)-(2R)-N-(2,3-dihydro-1,4-benzodioxin-6-ylmethyl)-4-(2,3-dihydro-1-benzofuran-7-ylmethyl)-N-isobutylmorpholine-2-carboxamide | 467.3 |
| 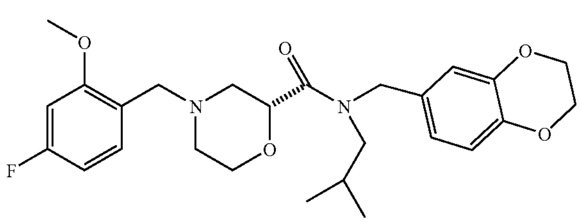 | (−)-(2R)-N-(2,3-dihydro-1,4-benzodioxin-6-ylmethyl)-4-(4-fluoro-2-methoxybenzyl)-N-isobutylmorpholine-2-carboxamide | 473.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 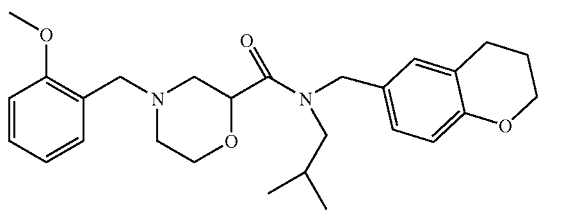 | (±)-N-(3,4-dihydro-2H-chromen-6-ylmethyl)-N-isobutyl-4-(2-methoxybenzyl)morpholine-2-carboxamide | 453.3 |
| 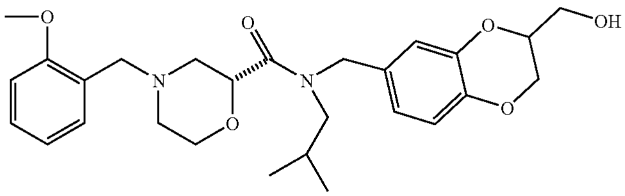 | (2R)-N-{[3-(hydroxymethyl)-2,3-dihydro-1,4-benzodioxin-6-yl]methyl-N-isobutyl-4-(2-methoxybenzyl)morpholine-2-carboxamide | 485.3 |
| 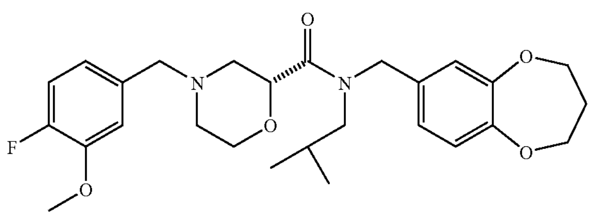 | (−)-(2R)-N-(3,4-dihydro-2H-1,5-benzodioxepin-7-ylmethyl)-4-(4-fluoro-3-methoxybenzyl)-N-isobutylmorpholine-2-carboxamide | 487.2567 |
| 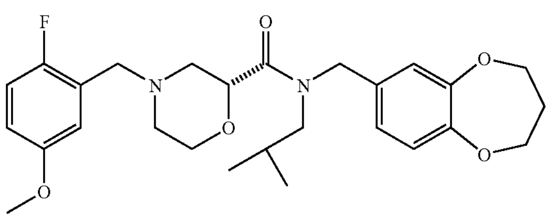 | (−)-(2R)-(3,4-dihydro-2H-1,5-benzodioxepin-7-ylmethyl)-4-(2-fluoro-5-methoxybenzyl)-N-isobutylmorpholine-2-carboxamide | 473.2470 |
| 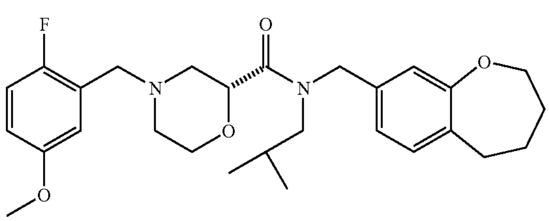 | (−)-(2R)-4-(2-fluoro-5-methoxybenzyl)-N-isobutyl-N-(2,3,4,5-tetrahydro-1-benzoxepin-8-ylmethyl)morpholine-2-carboxamide | 485.60 |
| 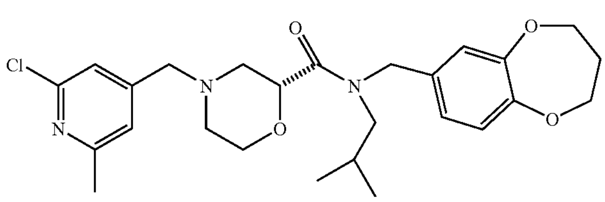 | (−)-(2R)-4-[(2-chloro-6-methylpyridin-4-yl)methyl]-N-(3,4-dihydro-2H-1,5-benzodioxepin-7-ylmethyl)-N-isobutylmorpholine-2-carboxamide | 491.3 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 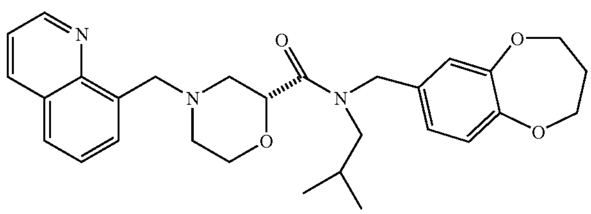 | (−)-(2R)-N-(3,4-dihydro-2H-1,5-benzodioxepin-7-ylmethyl)-N-isobutyl-4-(quinolin-8-ylmethyl)morpholine-2-carboxamide | 490.61 |
| 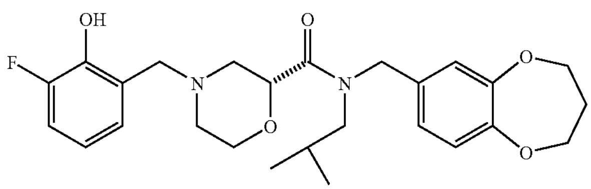 | (−)-(2R)-N-(3,4-dihydro-2H-1,5-benzodioxepin-7-ylmethyl)-4-(3-fluoro-2-hydroxybenzyl)-N-isobutylmorpholine-2-carboxamide | 473.65 |
| 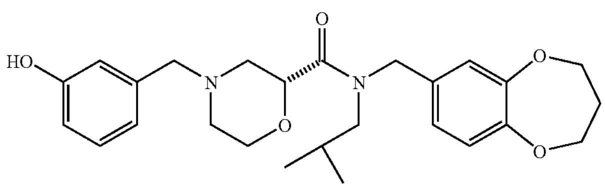 | (−)-(2R)-N-(3,4-dihydro-2H-1,5-benzodioxepin-7-ylmethyl)-4-(3-hydroxybenzyl)-N-isobutylmorpholine-2-carboxamide | 455.56 |
| 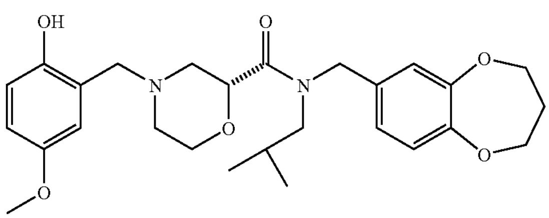 | (−)-(2R)-N-(3,4-dihydro-2H-1,5-benzodioxepin-7-ylmethyl)-4-(2-hydroxy-5-methoxybenzyl)-N-isobutylmorpholine-2-carboxamide | 485.58 |
| 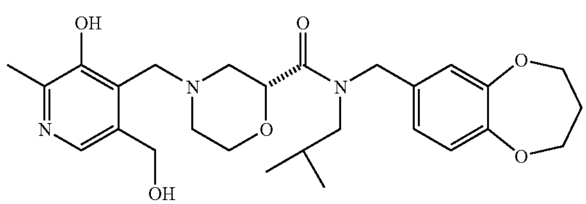 | (−)-(2R)-N-(3,4-dihydro-2H-1,5-benzodioxepin-7-ylmethyl)-4-{[3-hydroxy-5-(hydroxymethyl)-2-methylpyridin-4-yl]methyl}-N-isobutylmorpholine-2-carboxamide | 500.60 |
| 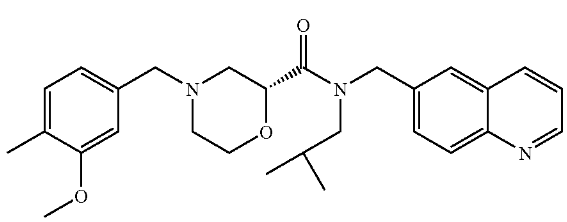 | (2R)-N-isobutyl-4-(3-methoxy-4-methylbenzyl)-N-(quinolin-6-ylmethyl)morpholine-2-carboxamide | 462.2765 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 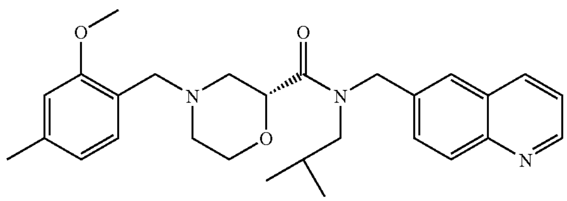 | (2R)-N-isobutyl-4-(2-methoxy-4-methylbenzyl)-N-(quinolin-6-ylmethyl)morpholine-2-carboxamide | 462.2 |
| 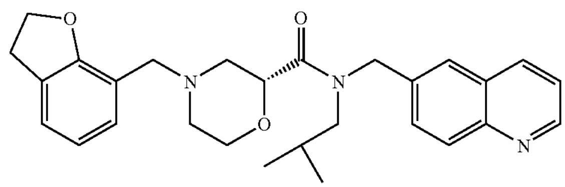 | (2R)-4-(2,3-dihydro-1-benzofuran-7-ylmethyl)-N-isobutyl-N-(quinolin-6-ylmethyl)morpholine-2-carboxamide | 460.261 |
| 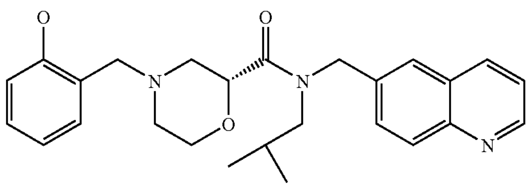 | (2R)-4-(2-hydroxybenzyl)-N-isobutyl-N-(quinolin-6-ylmethyl)morpholine-2-carboxamide | 434.2452 |
| 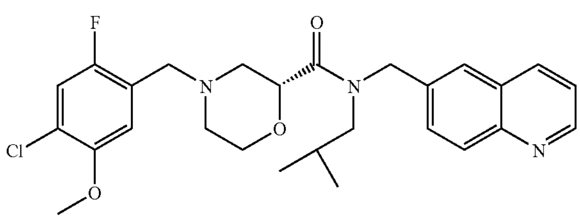 | (2R)-4-(4-chloro-2-fluoro-5-methoxybenzyl)-N-isobutyl-N-(quinolin-6-ylmethyl)morpholine-2-carboxamide | 500.2131 |
| 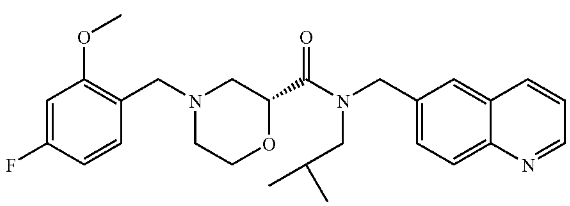 | (2R)-4-(4-fluoro-2-methoxybenzyl)-N-isobutyl-N-(quinolin-6-ylmethyl)morpholine-2-carboxamide | 466.2514 |
| 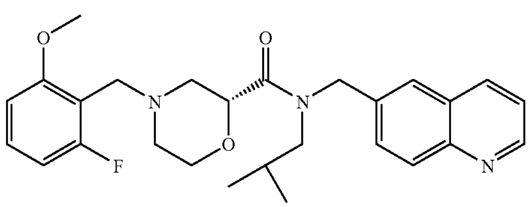 | (2R)-4-(2-fluoro-6-methoxybenzyl)-N-isobutyl-N-(quinolin-6-ylmethyl)morpholine-2-carboxamide | 466.2516 |
| 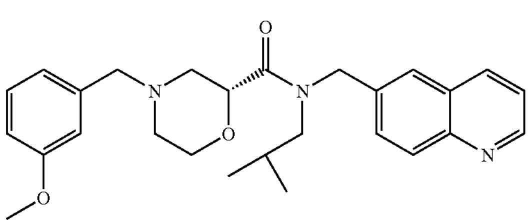 | (2R)-4-(3-ethoxybenzyl)-N-isobutyl-N-(quinolin-6-ylmethyl)morpholine-2-carboxamide | 462.2767 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 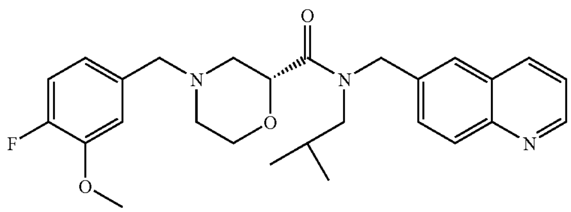 | (2R)-4-(4-fluoro-3-methoxybenzyl)-N-isobutyl-N-(quinolin-6-ylmethyl)morpholine-2-carboxamide | 466.2517 |
| 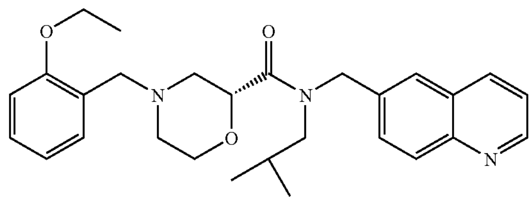 | (2R)-4-(2-ethoxybenzyl)-N-isobutyl-N-(quinolin-6-ylmethyl)morpholine-2-carboxamide | 462.2764 |
| 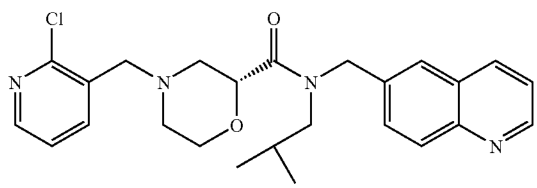 | (2R)-4-[(2-chloropyridin-3-yl)methyl]-N-isobutyl-N-(quinolin-6-ylmethyl)morpholine-2-carboxamide | 453.207 |
| 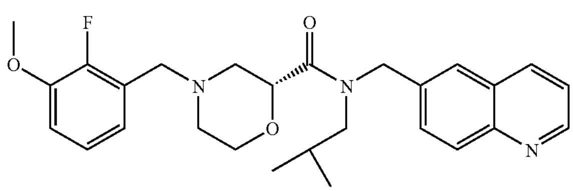 | (2R)-4-(2-fluoro-3-methoxybenzyl)-N-isobutyl-N-(quinolin-6-ylmethyl)morpholine-2-carboxamide | 466.2517 |
| 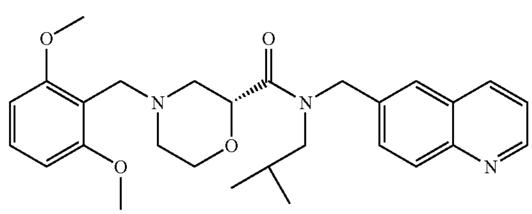 | (2R)-4-(2,6-dimethoxybenzyl)-N-isobutyl-N-(quinolin-6-ylmethyl)morpholine-2-carboxamide | 478.2714 |
| 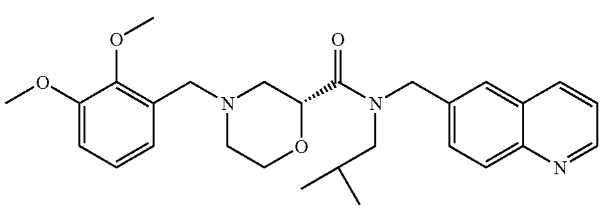 | (2R)-4-(2,3-dimethoxybenzyl)-N-isobutyl-N-(quinolin-6-ylmethyl)morpholine-2-carboxamide | 478.2716 |
| 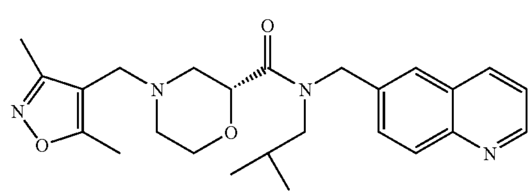 | (2R)-4-[(3,5-dimethylisoxazol-4-yl)methyl]-N-isobutyl-N-(quinolin-6-ylmethyl)morpholine-2-carboxamide | 437.2564 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 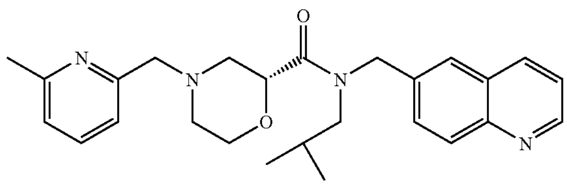 | (2R)-N-isobutyl-4-[(6-methylpyridin-2-yl)methyl]-N-(quinolin-6-ylmethyl)morpholine-2-carboxamide | 433.2609 |
| 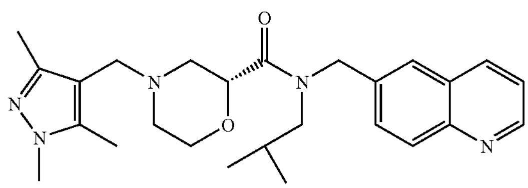 | (2R)-N-isobutyl-N-(quinolin-6-ylmethyl)-4-[(1,3,5-trimethyl-1H-pyrazol-4-yl)methyl]morpholine-2-carboxamide | 450.288 |
| 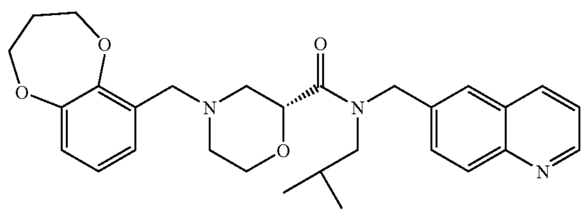 | (2R)-4-(3,4-dihydro-2H-1,5-benzodioxepin-6-ylmethyl)-N-isobutyl-N-(quinolin-6-ylmethyl)morpholine-2-carboxamide | 490.2716 |
| 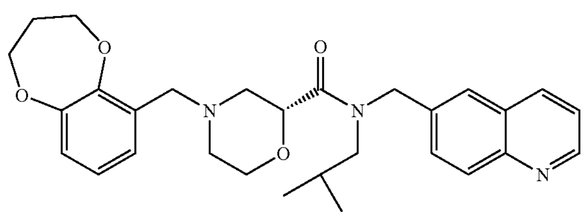 | (2R)-4-(2,3-dihydro-1,4-benzodioxin-5-ylmethyl)-N-isobutyl-N-(quinolin-6-ylmethyl)morpholine-2-carboxamide | 476.2559 |
| 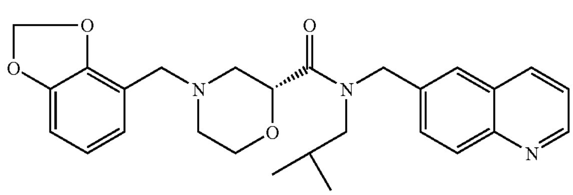 | (2R)-4-(1,3-benzodioxol-4-ylmethyl)-N-isobutyl-N-(quinolin-6-ylmethyl)morpholine-2-carboxamide | 462.2402 |
| 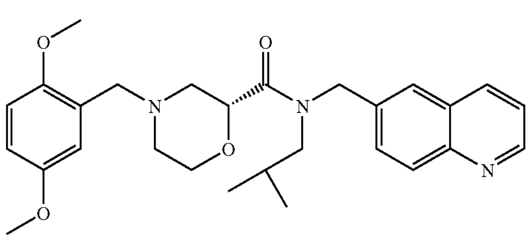 | (2R)-4-(2,5-dimethoxybenzyl)-N-isobutyl-N-(quinolin-6-ylmethyl)morpholine-2-carboxamide | 478.2714 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 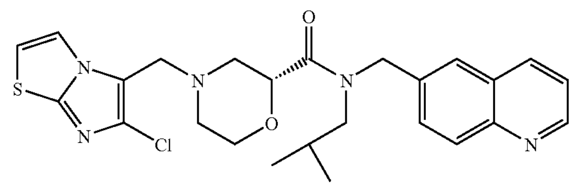 | (2R)-4-[(6-chloroimidazo[2,1-b][1,3]thiazol-5-yl)methyl]-N-isobutyl-N-(quinolin-6-ylmethyl)morpholine-2-carboxamide | 498.1743 |
| 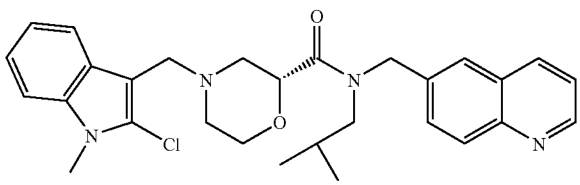 | (2R)-4-[(2-chloro-1-methyl-1H-indol-3-yl)methyl]-N-isobutyl-N-(quinolin-6-ylmethyl)morpholine-2-carboxamide | 505.239 |
| 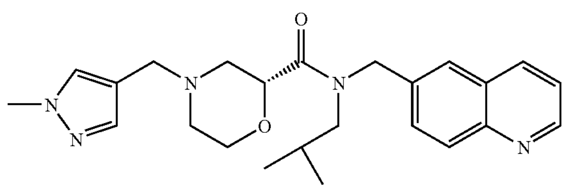 | (2R)-N-isobutyl-4-[(1-methyl-1H-pyrazol-4-yl)methyl]-N-(quinolin-6-ylmethyl)morpholine-2-carboxamide | 422.2564 |
| 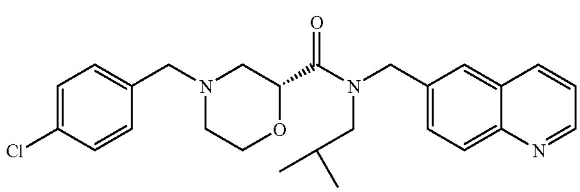 | (2R)-4-(4-chlorobenzyl)-N-isobutyl-N-(quinolin-6-ylmethyl)morpholine-2-carboxamide | 452.2116 |
| 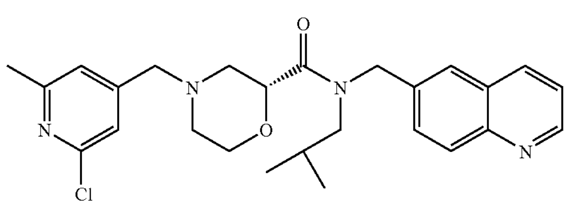 | (2R)-4-[(2-chloro-6-methylpyridin-4-yl)methyl]-N-isobutyl-N-(quinolin-6-ylmethyl)morpholine-2-carboxamide | 467.2227 |
| 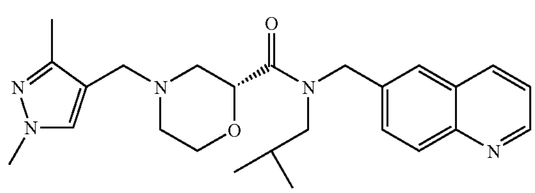 | (2R)-4-[(1,3-dimethyl-1H-pyrazol-4-yl)methyl]-N-isobutyl-N-(quinolin-6-ylmethyl)morpholine-2-carboxamide | 436.272 |
| 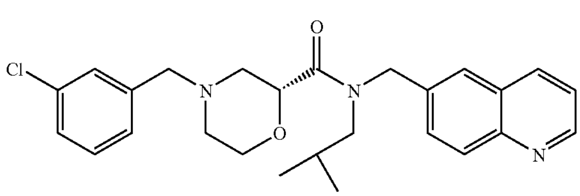 | (2R)-4-(3-chlorobenzyl)-N-isobutyl-N-(quinolin-6-ylmethyl)morpholine-2-carboxamide | 452.2117 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 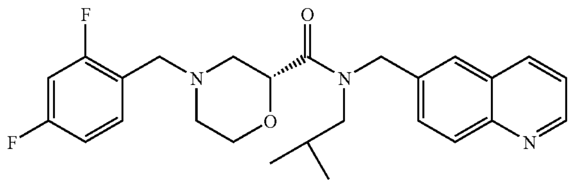 | (2R)-4-(2,4-difluorobenzyl)-N-isobutyl-N-(quinolin-6-ylmethyl)morpholine-2-carboxamide | 454.2317 |
| 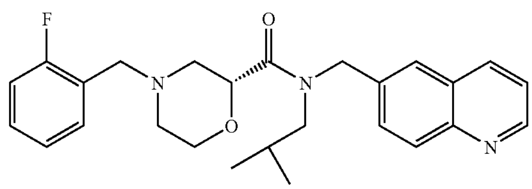 | (2R)-4-(2-fluorobenzyl)-N-isobutyl-N-(quinolin-6-ylmethyl)morpholine-2-carboxamide | 436.2409 |
| 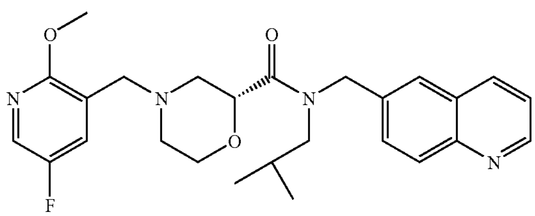 | (2R)-4-[(5-fluoro-2-methoxypyridin-3-yl)methyl]-N-isobutyl-N-(quinolin-6-ylmethyl)morpholine-2-carboxamide | 467.2466 |
| 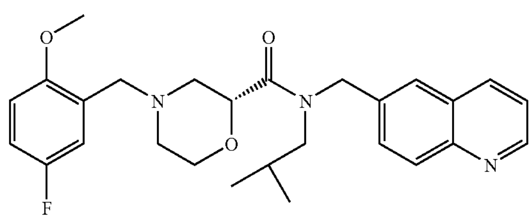 | (2R)-4-(5-fluoro-2-methoxybenzyl)-N-isobutyl-N-(quinolin-6-ylmethyl)morpholine-2-carboxamide | 466.2513 |
| 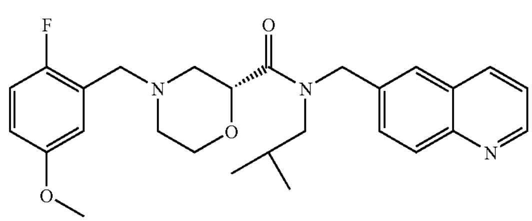 | (2R)-4-(2-fluoro-5-methoxybenzyl)-N-isobutyl-N-(quinolin-6-ylmethyl)morpholine-2-carboxamide | 466.2515 |
| 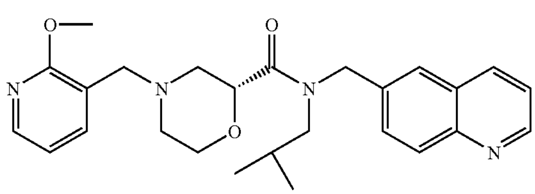 | (2R)-N-isobutyl-4-[(2-methoxypyridin-3-yl)methyl]-N-(quinolin-6-ylmethyl)morpholine-2-carboxamide | 449.2565 |
| 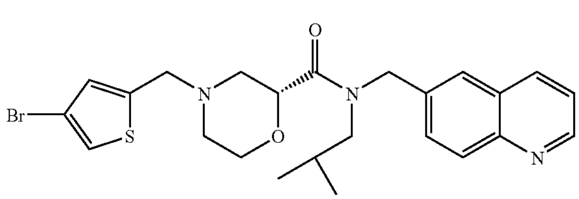 | (2R)-4-[(4-bromo-2-thienyl)methyl]-N-isobutyl-N-(quinolin-6-ylmethyl)morpholine-2-carboxamide | 502.1181 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 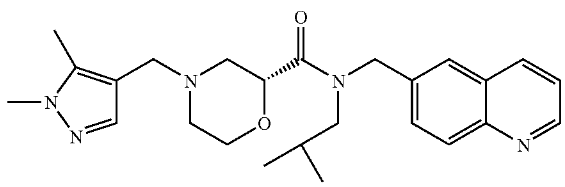 | (2R)-4-[(1,5-dimethyl-1H-pyrazol-4-yl)methyl]-N-isobutyl-N-(quinolin-6-ylmethyl)morpholine-2-carboxamide | 436.2721 |
| 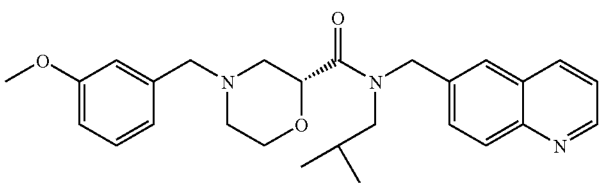 | (2R)-N-isobutyl-4-(3-methoxybenzyl)-N-(quinolin-6-ylmethyl)morpholine-2-carboxamide | 448.2607 |
| 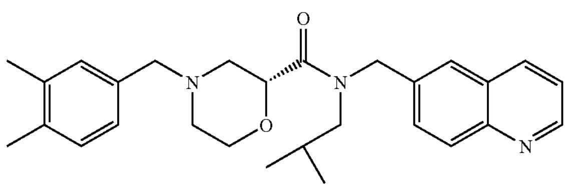 | (2R)-4-(3,4-dimethylbenzyl)-N-isobutyl-N-(quinolin-6-ylmethyl)morpholine-2-carboxamide | 446.2811 |
| 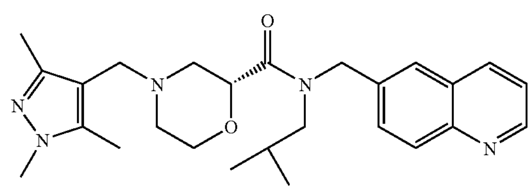 | (2R)-N-isobutyl-N-(quinolin-6-ylmethyl)-4-[(1,3,5-trimethyl-1H-pyrazol-4-yl)methyl]morpholine-2-carboxamide | 470.2338 |
| 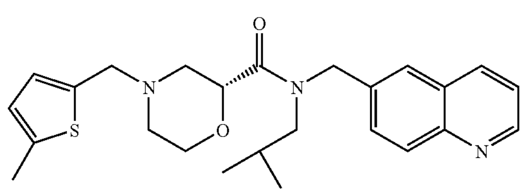 | (2R)-N-isobutyl-4-[(5-methyl-2-thienyl)methyl]-N-(quinolin-6-ylmethyl)morpholine-2-carboxamide | 438.2223 |
| 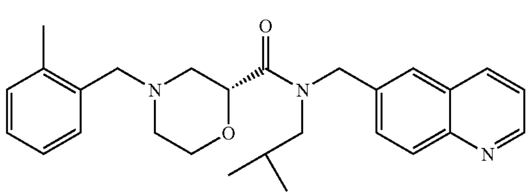 | (2R)-N-isobutyl-4-(2-methylbenzyl)-N-(quinolin-6-ylmethyl)morpholine-2-carboxamide | 432.2656 |
| 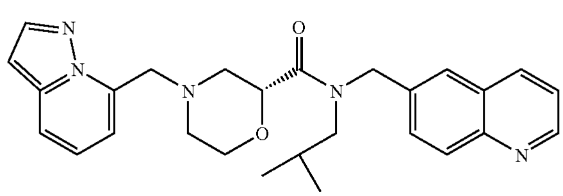 | (2R)-N-isobutyl-4-(pyrazolo[1,5-a]pyridin-7-ylmethyl)-N-(quinolin-6-ylmethyl)morpholine-2-carboxamide | 458.2563 |

TABLE 1-continued

The following compounds were prepared using the foregoing methodology, but substituting the appropiately substituted reagent, such as organomettalic or amine reagent, as described in the foregoing examples. The requisite starting materials were commercialy available, describe in the literature or readily synthesized by one skilled in the art of organic synthesis without undue experimentation.

| STRUCTURE | COMPOUND NAME | Mass ion: (M + 1) |
|---|---|---|
| 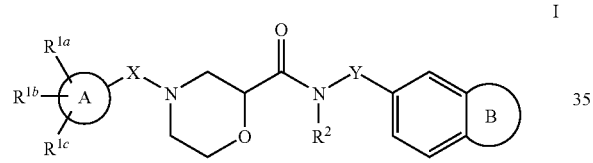 | (2R)-4-benzyl-N-isobutyl-N-(quinolin-6-ylmethyl)morpholine-2-carboxamide | 418.2498 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

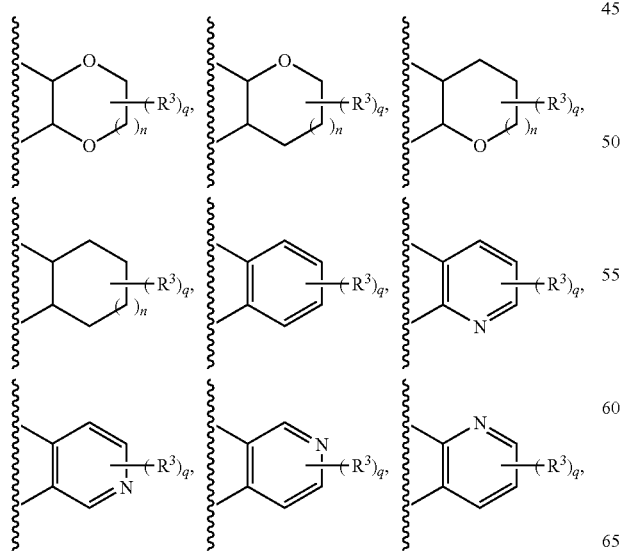

I wherein:
A is selected from the group consisting of phenyl, napthyl and heteroaryl;
B is selected from the group consisting of:

X and Y are independently —($C_{1-6}$alkylene)-, which is unsubstituted or substituted with one or more substituents selected from $R^{13}$;

$R^{1a}$, $R^{1b}$ and $R^{1c}$ may be absent if the valency of A does not permit such substitution and are independently selected from the group consisting of:
(1) hydrogen,
(2) halogen,
(3) hydroxyl,
(4) —(C═O)$_m$—O$_p$-$C_{1-6}$alkyl, where m is 0 or 1, p is 0 or 1 (wherein if m is 0 or p is 0, a bond is present) and where the alkyl is unsubstituted or substituted with one or more substituents selected from $R^{13}$,
(5) —(C═O)$_m$—O$_p$-$C_{3-6}$cycloalkyl, where the cycloalkyl is unsubstituted or substituted with one or more substituents selected from $R^{13}$,
(6) —(C═O)$_m$—$C_{2-4}$alkenyl, where the alkenyl is unsubstituted or substituted with one or more substituents selected from $R^{13}$,
(7) —(C═O)$_m$—O$_p$-phenyl or —(C═O)$_m$—O$_p$-napthyl, where the phenyl or napthyl is unsubstituted or substituted with one or more substituents selected from $R^{13}$,
(8) —(C═O)$_m$—O$_p$-heterocycle, where the heterocycle is unsubstituted or substituted with one or more substituents selected from $R^{13}$,
(9) —(C═O)$_m$—NR$^{10}$R$^{11}$, wherein $R^{10}$ and $R^{11}$ are independently selected from the group consisting of:
(a) hydrogen,
(b) $C_{1-6}$alkyl, which is unsubstituted or substituted with $R^{13}$,
(c) $C_{3-6}$alkenyl, which is unsubstituted or substituted with $R^{13}$,
(d) cycloalkyl which is unsubstituted or substituted with $R^{13}$,
(e) phenyl, which is unsubstituted or substituted with $R^{13}$, and
(f) heterocycle, which is unsubstituted or substituted with $R^{13}$,
(10) —S(O)$_2$—NR$^{10}$R$^{11}$,
(11) —S(O)$_t$—R$^{12}$, where t is 0, 1 or 2 and where $R^{12}$ is selected from the definitions of $R^{10}$ and $R^{11}$,
(12) —CO$_2$H,
(13) —CN, and
(14) —NO$_2$;

R² is selected from the group consisting of:
   (1) hydrogen,
   (2) C$_{1-6}$alkyl, which is unsubstituted or substituted with one or more substituents selected from R$^{13}$,
   (3) —C$_{3-6}$cycloalkyl, which is unsubstituted or substituted with one or more substituents selected from R$^{13}$,
   (4) -phenyl which is unsubstituted or substituted with one or more substituents selected from R$^{13}$;
R³ is independently selected from:
   (1) hydrogen,
   (2) halogen,
   (3) hydroxy, and
   (4) C$_{1-6}$alkyl, which is unsubstituted or substituted with one or more substituents selected from R$^{13}$,
      or two R³ at the same position are joined to form a furan, oxetane or pyran ring,
      or two R³ at adjacent positions are joined to form a phenyl ring;
R$^{13}$ is selected from the group consisting of:
   (1) halogen,
   (2) hydroxyl,
   (3) —(C=O)$_m$—O$_p$-C$_{1-6}$alkyl, where the alkyl is unsubstituted or substituted with one or more substituents selected from R$^{14}$,
   (4) —O$_n$—(C$_{1-3}$)perfluoroalkyl,
   (5) —(C=O)$_m$—O$_p$-C$_{3-6}$cycloalkyl, where the cycloalkyl is unsubstituted or substituted with one or more substituents selected from R$^{14}$,
   (6) —(C=O)$_m$—C$_{2-4}$alkenyl, where the alkenyl is unsubstituted or substituted with one or more substituents selected from R$^{14}$,
   (7) —(C=O)$_m$—O$_p$-phenyl or —(C=O)$_m$—O$_p$-napthyl, where the phenyl or napthyl is unsubstituted or substituted with one or more substituents selected from R$^{14}$,
   (8) —(C=O)$_m$—O$_p$-heterocycle, where the heterocycle is unsubstituted or substituted with one or more substituents selected from R$^{14}$,
   (9) —(C=O)$_m$—NR$^{10}$R$^{11}$,
   (10) —S(O)$_2$—NR$^{10}$R$^{11}$,
   (11) —S(O)$_t$—R$^{12}$,
   (12) —CO$_2$H,
   (13) —CN, and
   (14) —NO$_2$;
R$^{14}$ is selected from the group consisting of:
   (1) hydroxyl,
   (2) halogen,
   (3) C$_{1-6}$alkyl,
   (4) —C$_{3-6}$cycloalkyl,
   (5) —O—C$_{1-6}$alkyl,
   (6) —O(C=O)—C$_{1-6}$alkyl,
   (7) —NH—C$_{1-6}$alkyl,
   (8) phenyl,
   (9) heterocycle,
   (10) —CO$_2$H, and
   (11) —CN;
n is 0, 1, 2, 3, 4, 5 or 6;
q is 0, 1, 2, 3 or 4;
or an N-oxide thereof or a pharmaceutically acceptable salt thereof.

2. The compound of claim 1 of the formula Ib:

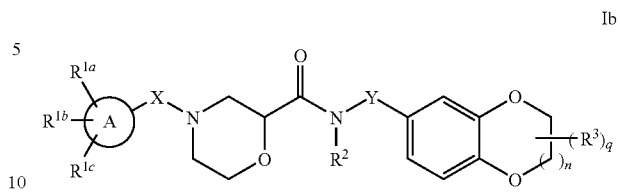

or a pharmaceutically acceptable salt thereof.

3. The compound of claim 1 of the formula Ic:

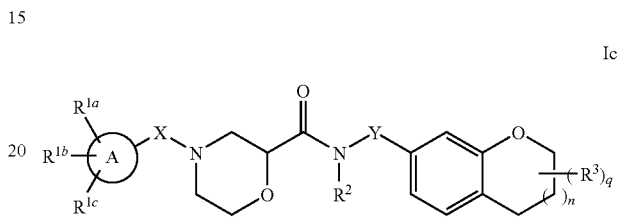

or a pharmaceutically acceptable salt thereof.

4. The compound of claim 1 of the formula Id:

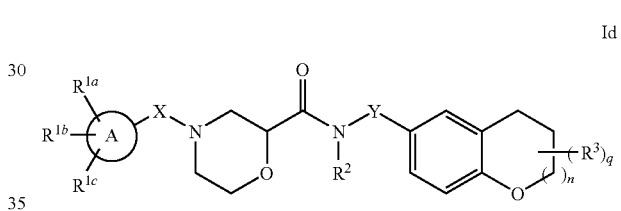

or a pharmaceutically acceptable salt thereof.

5. The compound of claim 1 of the formula If:

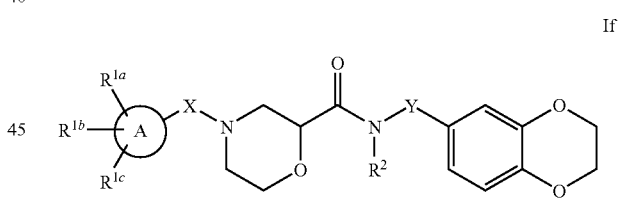

or a pharmaceutically acceptable salt thereof.

6. The compound of claim 1 of the formula Ig:

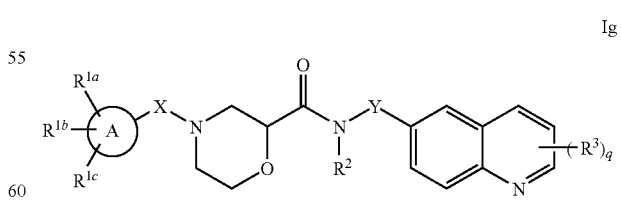

or a pharmaceutically acceptable salt thereof.

7. The compound of claim 1 wherein A is phenyl.
8. The compound of claim 1 wherein A is pyridyl.
9. The compound of claim 1 wherein X is —CH$_2$—.
10. The compound of claim 1 wherein Y is —CH$_2$—.

11. The compound of claim 1 wherein $R^{1a}$, $R^{1b}$ and $R^{1c}$ are independently selected from the group consisting of:
  (1) hydrogen,
  (2) halogen,
  (3) $C_{1-6}$alkyl, which is unsubstituted or substituted with halogen, hydroxyl, phenyl or
      —O—$C_{1-6}$alkyl,
  (4) $C_{2-4}$alkenyl, which is unsubstituted or substituted with $C_{3-6}$cycloalkyl or phenyl,
  (5) —O—$C_{1-6}$alkyl, which is unsubstituted or substituted with halogen, hydroxyl, phenyl or
      —O—$C_{1-6}$alkyl,
  (6) phenyl, which is unsubstituted or substituted with halogen, hydroxyl, $C_{1-6}$alkyl, —O—$C_{1-6}$alkyl, —SH, —$NO_2$, —$CO_2H$, or —CN,
  (7) —$NR^{10}R^{11}$, wherein $R^{10}$ and $R^{11}$ are independently selected from hydrogen and $C_{1-6}$alkyl,
  (8) tetrazolyl,
  (9) thienyl,
  (10) triazolyl,
  (11) benzothienyl,
  (12) pyrazolyl,
  (13) imidazolyl,
  (14) —$NO_2$,
  (15) hydroxyl, and
  (16) —CN.

12. The compound of claim 11 wherein $R^{1b}$ is hydrogen, $R^{1c}$ is hydrogen and $R^{1a}$ selected from the group consisting of:
  (1) hydrogen,
  (2) fluoro,
  (3) —O—$C_{1-6}$alkyl, and
  (4) phenyl.

13. The compound of claim 7 wherein A is phenyl, $R^{1b}$ is hydrogen, $R^{1c}$ is hydrogen and $R^{1a}$ selected from the group consisting of:
  (1) hydrogen,
  (2) fluoro, and
  (3) —O—$CH_3$.

14. The compound of claim 1 wherein $R^2$ is selected from the group consisting of:
  (1) $C_{1-6}$alkyl, and
  (2) $C_{1-6}$alkyl-$C_{3-6}$cycloalkyl.

15. The compound of claim 1 wherein $R^3$ is independently selected from:
  (1) hydrogen,
  (2) halogen, and
  (3) $C_{1-6}$alkyl.

16. The compound of claim 15 wherein $R^3$ is independently selected from:
  (1) hydrogen,
  (2) fluoro, and
  (3) methyl.

17. A compound which is selected from the group consisting of:
  4-Benzyl-N-(3,4-dihydro-2H-1,5-benzodioxepin-7-ylmethyl)-N-isobutylmorpholine-2-carboxamide;
  (2R)—N-(3,4-dihydro-2H-1,5-benzodioxepin-7-ylmethyl)-N-isobutyl-4-(2-methoxybenzyl)morpholine-2-carboxamide;
  4-Benzyl-N-isobutyl-N-(2,3,4,5-tetrahydro-1,6-benzodioxocin-8-ylmethyl)morpholine-2-carboxamide;
  4-Benzyl-N-isobutyl-N-[(3,3,4,4-tetrafluoro-2,3,4,5-tetrahydro-1,6-benzodioxocin-8-yl)methyl]-morpholine-2-carboxamide;
  4-Benzyl-N-[(3,3-difluoro-3,4-dihydro-2H-1,5-benzodioxepin-7-yl)methyl]-N-isobutylmorpholine-2-carboxamide;
  (2R)—N-[(3-fluoro-3,4-dihydro-2H-1,5-benzodioxepin-7-yl)methyl]-N-isobutyl-4-(2-methoxybenzyl)morpholine-2-carboxamide;
  4-benzyl-N-(2,3-dihydro-1-benzofuran-5-ylmethyl)-N-isobutylmorpholine-2-carboxamide;
  4-benzyl-N-[(5,5-dimethyl-2,3,4,5-tetrahydro-1-benzoxepin-7-yl)methyl]-N-isobutylmorpholine-2-carboxamide;
  (2R)—N-(3,4-dihydro-2H-1,5-benzodioxepin-7-ylmethyl)-N-isobutyl-4-[(3-methoxypyrazin-2-yl)methyl]morpholine-2-carboxamide;
  (2R)—N-(3,4-dihydro-2H-1,5-benzodioxepin-7-ylmethyl)-N-isobutyl-4-[(5-methoxypyridin-3-yl)methyl]morpholine-2-carboxamide;
  (2R)—N-(3,4-dihydro-2H-1,5-benzodioxepin-7-ylmethyl)-N-isobutyl-4-[(2-methoxy-6-methylpyrimidin-4-yl)methyl]morpholine-2-carboxamide;
  (2R)—N-(3,4-dihydro-2H-1,5-benzodioxepin-7-ylmethyl)-N-isobutyl-4-[(3-methoxypyridin-4-yl)methyl]morpholine-2-carboxamide;
  (2R)—N-(3,4-dihydro-2H-1,5-benzodioxepin-7-ylmethyl)-N-isobutyl-4-[(4-methoxypyrimidin-5-yl)methyl]morpholine-2-carboxamide;
  (2R)—N-(2,3-dihydro-1,4-benzodioxin-6-ylmethyl)-N-isobutyl-4-(2-methoxybenzyl)morpholine-2-carboxamide;
  N-Isobutyl-4-(2-methoxybenzyl)-N-(2,3,4,5-tetrahydro-1-benzoxepin-8-ylmethyl)morpholine-2-carboxamide;
  4-Benzyl-N-isobutyl-N-(2,3,4,5-tetrahydro-1-benzoxepin-8-ylmethyl)morpholine-2-carboxamide;
  N-Isobutyl-4-(2-methoxybenzyl)-N-(2,3,4,5-tetrahydro-1-benzoxepin-7-ylmethyl)morpholine-2-carboxamide;
  4-Benzyl-N-isobutyl-N-(2,3,4,5-tetrahydro-1-benzoxepin-8-ylmethyl)morpholine-2-carboxamide;
  N-(3,4-Dihydro-2H-chromen-7-ylmethyl)-N-isobutyl-4-(2-methoxybenzyl)morpholine-2-carboxamide;
  4-Benzyl-N-(3,4-dihydro-2H-chromen-7-ylmethyl)-N-isobutylmorpholine-2-carboxamide;
  N-(3,4-Dihydro-2H-chromen-6-ylmethyl)-N-isobutyl-4-(2-methoxybenzyl)morpholine-2-carboxamide;
  N-[(9-Hydroxy-6,7,8,9-tetrahydro-5H-benzo[7]annulen-2-yl)methyl]-N-isobutyl-4-(2-methoxybenzyl)morpholine-2-carboxamide;
  4-Benzyl-N-[(9-hydroxy-6,7,8,9-tetrahydro-5H-benzo[7]annulen-2-yl)methyl]-N-isobutylmorpholine-2-carboxamide;
  N-Isobutyl-4-(2-methoxybenzyl)-N-[(9-methoxy-6,7,8,9-tetrahydro-5H-benzo[7]annulen-2-yl)methyl]morpholine-2-carboxamide;
  4-Benzyl-N-isobutyl-N-[(9-methoxy-6,7,8,9-tetrahydro-5H-benzo[7]annulen-2-yl)methyl]morpholine-2-carboxamide;
  N-Isobutyl-4-(2-methoxybenzyl)-N-(6,7,8,9-tetrahydro-5H-benzo[7]annulen-2-ylmethyl)morpholine-2-carboxamide;
  4-Benzyl-N-isobutyl-N-(6,7,8,9-tetrahydro-5H-benzo[7]annulen-2-ylmethyl)morpholine-2-carboxamide;
  4-benzyl-N-(2,3-dihydro-1,4-benzodioxin-6-ylmethyl)-N-isobutylmorpholine-2-carboxamide;
  (R)-4-benzyl-N-(2,3-dihydro-1,4-benzodioxin-6-ylmethyl)-N-isobutylmorpholine-2-carboxamide;
  (S)-4-benzyl-N-(2,3-dihydro-1,4-benzodioxin-6-ylmethyl)-N-isobutylmorpholine-2-carboxamide;

4-benzyl-N-cyclopentyl-N-(2,3-dihydro-1,4-benzo-
dioxin-6-ylmethyl)morpholine-2-carboxamide;
4-benzyl-N-(cyclohexylmethyl)-N-(2,3-dihydro-1,4-ben-
zodioxin-6-ylmethyl)morpholine-2-carboxamide;
4-benzyl-N-(2,3-dihydro-1,4-benzodioxin-6-ylmethyl)-
N-(2,2-dimethylpropyl)morpholine-2-carboxamide;
4-benzyl-N-(2,3-dihydro-1,4-benzodioxin-6-ylmethyl)-
N-propylmorpholine-2-carboxamide;
4-benzyl-N-(cyclopropylmethyl)-N-(2,3-dihydro-1,4-
benzodioxin-6-ylmethyl)morpholine-2-carboxamide;
4-benzyl-N-(2,3-dihydro-1,4-benzodioxin-6-ylmethyl)
morpholine-2-carboxamide;
N-(1,3-benzodioxol-5-ylmethyl)-4-benzylmorpholine-2-
carboxamide;
N-(1,3-benzodioxol-5-ylmethyl)-4-benzyl-N-isobutyl-
morpholine-2-carboxamide;
4-benzyl-N-(cyclopentylmethyl)-N-(2,3-dihydro-1,4-
benzodioxin-6-ylmethyl)morpholine-2-carboxamide;
4-cyclobutyl-N-(2,3-dihydro-1,4-benzodioxin-6-ylm-
ethyl)-N-isobutylmorpholine-2-carboxamide;
4-cyclopentyl-N-(2,3-dihydro-1,4-benzodioxin-6-ylm-
ethyl)-N-isobutylmorpholine-2-carboxamide;
N-(2,3-dihydroL1,4-benzodioxin-6-ylmethyl)-N-isobu-
tyl-4-isopropylmorpholine-2-carboxamide;
N-(2,3-dihydro-1,4-benzodioxin-6-ylmethyl)-4-(4-fluo-
robenzyl)-N-isobutylmorpholine-2-carboxamide;
N-(2,3-dihydro-1,4-benzodioxin-6-ylmethyl)-N-isobutyl-
4-(pyridin-2-ylmethyl)morpholine-2-carboxamide;
N-(2,3-dihydro-1,4-benzodioxin-6-ylmethyl)-N-isobutyl-
4-(2-phenylethyl)morpholine-2-carboxamide;
4-benzyl-N-(3,4-dihydro-2H-1,5-benzodioxepin-7-ylm-
ethyl)-N-isobutylmorpholine-2-carboxamide;
4-benzyl-N-[1-(2,3-dihydro-1,4-benzodioxin-6-ypethyl]-
N-isobutylmorpholine-2-carboxamide;
4-benzyl-N-(2,3-dihydro-1-benzofuran-5-ylmethyl)-N-
isobutylmorpholine-2-carboxamide;
4-benzyl-N-isobutyl-N-[(3-oxo-1,3-dihydro-2-benzofu-
ran-5-yl)methyl]morpholine-2-carboxamide;
4-benzyl-N-[(2,2-dimethyl-3,4-dihydro-2H-chromen-6-
yl)methyl]-N-isobutylmorpholine-2-carboxamide;
(2S)-4-benzyl-N-(3,4-dihydro-2H-1,5-benzodioxepin-7-
ylmethyl)-N-isobutylmorpholine-2-carboxamide;
(2R)-4-benzyl-N-(3,4-dihydro-2H-1,5-benzodioxepin-7-
ylmethyl)-N-isobutylmorpholine-2-carboxamide;
4-benzyl-N-(2,3-dihydro-1-benzofuran-6-ylmethyl)-N-
isobutylmorpholine-2-carboxamide;
N-(2,3-dihydro-1,4-benzodioxin-6-ylmethyl)-N-isobutyl-
4-(1-phenylethyl)morpholine-2-carboxamide;
4-benzyl-N-(3,4-dihydro-2H-chromen-8-ylmethyl)-N-
isobutylmorpholine-2-carboxamide;
4-benzyl-N-(3,4-dihydro-2H-chromen-6-ylmethyl)-N-
isobutylmorpholine-2-carboxamide;
N-(2,3-dihydro-1,4-benzodioxin-6-ylmethyl)-N-isobutyl-
4-(2,3,4-trifluorobenzyl)morpholine-2-carboxamide;
4-[(4-chloro-1-methyl-1H-pyrazol-3-yl)methyl]-N-(2,3-
dihydro-1,4-benzodioxin-6-ylmethyl)-N-isobutylmor-
pholine-2-carboxamide;
N-(2,3-dihydro-1,4-benzodioxin-6-ylmethyl)-N-isobutyl-
4-(2,3,5,6-tetrafluorobenzyl)morpholine-2-carboxam-
ide;
N-(2,3-dihydro-1,4-benzodioxin-6-ylmethyl)-4-[(1,5-
dimethyl-3-oxo-2-phenyl-2,3-dihydro-1H-pyrazol-4-
yl)methyl]-N-isobutylmorpholine-2-carboxamide;
N-(2,3-dihydro-1,4-benzodioxin-6-ylmethyl)-N-isobutyl-
4-[(1-methyl-1H-pyrrol-2-yl)methyl]morpholine-2-
carboxamide;
N-(2,3-dihydro-1,4-benzodioxin-6-ylmethyl)-4-(2-furyl-
methyl)-N-isobutylmorpholine-2-carboxamide;
N-(2,3-dihydro-1,4-benzodioxin-6-ylmethyl)-N-isobutyl-
4-[(5-methyl-2-furyl)methyl]morpholine-2-carboxam-
ide;
4[4-(diethylamino)-2-hydroxybenzyl]-N-(2,3-dihydro-1,
4-benzodioxin-6-ylmethyl)-N-isobutylmorpholine-2-
carboxamide;
N-(2,3-dihydro-1,4-benzodioxin-6-ylmethyl)-N-isobutyl-
4-(2-methylbenzyl)morpholine-2-carboxamide;
4-[4-(acetylamino)benzyl]-N-(2,3-dihydro-1,4-benzo-
dioxin-6-ylmethyl)-N-isobutylmorpholine-2-carboxa-
mide;
N-(2,3-dihydro-1,4-benzodioxin-6-ylmethyl)-4-[4-(dim-
ethylamino)benzyl]-N-isobutylmorpholine-2-carboxa-
mide;
N-(2,3-dihydro-1,4-benzodioxin-6-ylmethyl)-N-isobutyl-
4-[(5-methyl-2-thienyl)methyl]morpholine-2-carboxa-
mide;
N-(2,3-dihydro-1,4-benzodioxin-6-ylmethyl)-N-isobutyl-
4-[(6-methylpyridin-2-yl)methyl]morpholine-2-car-
boxamide;
N-(2,3-dihydro-1,4-benzodioxin-6-ylmethyl)-4-(4-hy-
droxy-3,5-dimethylbenzyl)-N-isobutylmorpholine-2-
carboxamide;
4-(1,3-benzodioxol-5-ylmethyl)-N-(2,3-dihydro-1,4-ben-
zodioxin-6-ylmethyl)-N-isobutylmorpholine-2-car-
boxamide;
N-(2,3-dihydro-1,4-benzodioxin-6-ylmethyl)-N-isobutyl-
4-[4-(methylthio)benzyl]morpholine-2-carboxamide;
N-(2,3-dihydro-1,4-benzodioxin-6-ylmethyl)-N-isobutyl-
4-[4-(trifluoromethyl)benzyl]morpholine-2-carboxam-
ide;
4-[3,5-bis(trifluoromethyl)benzyl]-N-(2,3-dihydro-1,4-
benzodioxin-6-ylmethyl)-N-isobutylmorpholine-2-car-
boxamide;
4-(3,5-difluorobenzyl)-N-(2,3-dihydro-1,4-benzodioxin-
6-ylmethyl)-N-isobutylmorpholine-2-carboxamide;
N-(2,3-dihydro-1,4-benzodioxin-6-ylmethyl)-4-(3-furyl-
methyl)-N-isobutylmorpholine-2-carboxamide;
N-(2,3-dihydro-1,4-benzodioxin-6-ylmethyl)-4-{[4-
(dimethylamino)-1-naphthyl]methyl}-N-isobutylmor-
pholine-2-carboxamide;
N-(2,3-dihydro-1,4-benzodioxin-6-ylmethyl)-N-isobutyl-
4-(4-propoxybenzyl)morpholine-2-carboxamide;
N-(2,3-dihydro-1,4-benzodioxin-6-ylmethyl)-4-[(5-ethyl-
2-furyl)methyl]-N-isobutylmorpholine-2-carboxam-
ide;
4-(2-chloro-4-fluorobenzyl)-N-(2,3-dihydro-1,4-benzo-
dioxin-6-ylmethyl)-N-isobutylmorpholine-2-carboxa-
mide;
N-(2,3-dihydro-1,4-benzodioxin-6-ylmethyl)-N-isobutyl-
4-[4-(trifluoromethoxy)benzyl]morpholine-2-carboxa-
mide;
4-[(6,8-dichloro-4-oxo-4H-chromen-3-yl)methyl]-N-(2,
3-dihydro-1,4-benzodioxin-6-ylmethyl)-N-isobutyl-
morpholine-2-carboxamide;
4-[(5-chloro-1,3-dimethyl-1H-pyrazol-4-yl)methyl]-N-
(2,3-dihydro-1,4-benzodioxin-6-ylmethyl)-N-isobutyl-
morpholine-2-carboxamide;
4-(biphenyl-4-ylmethyl)-N-(2,3-dihydro-1,4-benzo-
dioxin-6-ylmethyl)-N-isobutylmorpholine-2-carboxa-
mide;
N-(2,3-dihydro-1,4-benzodioxin-6-ylmethyl)-N-isobutyl-
4-[(1-methyl-1H-imidazol-2-yl)methyl]morpholine-2-
carboxamide;

4-[(4'-chlorobiphenyl-4-yl)methyl]-N-(2,3-dihydro-1,4-benzodioxin-6-ylmethyl)-N-isobutylmorpholine-2-carboxamide;
4-(1-benzothien-2-ylmethyl)-N-(2,3-dihydro-1,4-benzodioxin-6-ylmethyl)-N-isobutylmorpholine-2-carboxamide;
4-(2,5-difluorobenzyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-[3-(trifluoromethyl)benzyl]morpholine-2-carboxamide;
4-(4-cyanobenzyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-4-(2-fluorobenzyl)-N-isobutylmorpholine-2-carboxamide;
4-(2,4-difluorobenzyl)-N-(2,3-dihydro-1,4-benzodioxin-6-ylmethyl)-N-isobutylmorpholine-2-carboxamide;
4-(2-cyanobenzyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-(4-methoxybenzyl)morpholine-2-carboxamide;
4-(3-chlorobenzyl)-N-(2,3-dihydro-1,4-benzodioxin-6-ylmethyl)-N-isobutylmorpholine-2-carboxamide;
4-(4-chlorobenzyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-4-(3,4-dimethylbenzyl)-N-isobutylmorpholine-2-carboxamide;
N-(2,3-dihydro-1,4-benzodioxin-6-ylmethyl)-N-isobutyl-4-[(2'-methylbiphenyl-4-yl)methyl]morpholine-2-carboxamide;
4-(2-chlorobenzyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-(2-methoxybenzyl)morpholine-2-carboxamide;
N-(2,3-dihydro-1,4-benzodioxin-6-ylmethyl)-N-isobutyl-4-(3-methoxybenzyl)morpholine-2-carboxamide;
N-(2,3-dihydro-1,4-benzodioxin-6-ylmethyl)-4-(1H-indol-3-ylmethyl)-N-isobutylmorpholine-2-carboxamide;
N-(2,3-dihydro-1,4-benzodioxin-6-ylmethyl)-N-isobutyl-4-[1,3-thiazol-4-ylmethyl)morpholine-2-carboxamide;
N-(2,3-dihydro-1,4-benzodioxin-6-ylmethyl)-N-isobutyl-4-[(2-phenylimidazo[1,2-a]pyridin-3-yl)methyl]morpholine-2-carboxamide;
N-(2,3-dihydro-1,4-benzodioxin-6-ylmethyl)-N-isobutyl-4-{4-[(4-methoxybenzyl)oxy]benzyl} morpholine-2-carboxamide;
4-{[2-(diethylamino)-1,3-thiazol-5-yl]methyl}-N-(2,3-dihydro-1,4-benzodioxin-6-ylmethyl)-N-isobutylmorpholine-2-carboxamide;
4-(1,3-benzothiazol-2-ylmethyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-[(1-methyl-1H-pyrazol-3-yl)methyl]morpholine-2-carboxamide;
N-(2,3-dihydro-1,4-benzodioxin-6-ylmethyl)-4-[(1,3-diphenyl-1H-pyrazol-4-yl)methyl]-N-isobutylmorpholine-2-carboxamide;
N-(2,3-dihydro-1,4-benzodioxin-6-ylmethyl)-N-isobutyl-4-[(1-methyl-1H-pyrazol-4-yl)methyl]morpholine-2-carboxamide;
N-(2,3-dihydro-1,4-benzodioxin-6-ylmethyl)-N-isobutyl-4-(pyrazin-2-ylmethyl)morpholine-2-carboxamide;
N-(2,3-dihydro-1,4-benzodioxin-6-ylmethyl)-N-isobutyl-4-[(1-methyl-1,2,3,4-tetrahydroquinolin-6-yl)methyl]morpholine-2-carboxamide;
N-(2,3-dihydro-1,4-benzodioxin-6-ylmethyl)-N-isobutyl-4-[(5-piperidin-1-yl-2-furyl)methyl]morpholine-2-carboxamide;
4-(biphenyl-2-ylmethyl)-N-(2,3-dihydro-1,4-benzodioxin-6-ylmethyl)-N-isobutylmorpholine-2-carboxamide;
4-(biphenyl-3-ylmethyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-[(2'-methylbiphenyl-3-yl)methyl]morpholine-2-carboxamide;
N-(2,3-dihydro-1,4-benzodioxin-6-ylmethyl)-N-isobutyl-4-[1-(1,3-thiazol-2-yl)-1H-pyrrol-2-yl]methyl)morpholine-2-carboxamide;
N-(2,3-dihydro-1,4-benzodioxin-6-ylmethyl)-N-isobutyl-4-[(4-methyl-1H-imidazol-2-yl)methyl]morpholine-2-carboxamide;
4-{[1-(5-chloropyridin-2-yl)-1H-pyrrol-2-yl]methyl}-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-[(2-phenyl-1,3-thiazol-5-yl)methyl]morpholine-2-carboxamide;
N-(2,3-dihydro-1,4-benzodioxin-6-ylmethyl)-N-isobutyl-4-[(4-phenyl-1,3-thiazol-2-yl)methyl]morpholine-2-carboxamide;
N-(2,3-dihydro-1,4-benzodioxin-6-ylmethyl)-N-isobutyl-4-[(6-methylimidazol[2,1-b][1,3]thiazol-5-yl)methyl]morpholine-2-carboxamide;
N-(2,3-dihydro-1,4-benzodioxin-6-ylmethyl)-4-[(1,5-dimethyl-1H-pyrazol-4-yl)methyl]-N-isobutylmorpholine-2-carboxamide;
N-(2,3-dihydro-1,4-benzodioxin-6-ylmethyl)-N-isobutyl-4-[1,3-oxazol-5-ylmethyl)morpholine-2-carboxamide;
N-(2,3-dihydro-1,4-benzodioxin-6-ylmethyl)-N-isobutyl-4-[(1-methyl-3-phenyl-1H-pyrazol-4-yl)methyl]morpholine-2-carboxamide;
N-(2,3-dihydro-1,4-benzodioxin-6-ylmethyl)-N-isobutyl-4-[(1-phenyl-1H-pyrazol-4-yl)methyl]morpholine-2-carboxamide;
N-(2,3-dihydro-1,4-benzodioxin-6-ylmethyl)-N-isobutyl-4-[(1-pyridin-2-yl-1H-pyrrol-2-yl)methyl]morpholine-2-carboxamide;
N-(2,3-dihydro-1,4-benzodioxin-6-ylmethyl)-N-isobutyl-4-{[5-(methoxymethyl)-2-furyl]methyl} morpholine-2-carboxamide;
4-[(2-chloro-6-methylpyridin-4-yOmethyl]-N-(2,3-dihydro-1,4-benzodioxin-6-ylmethyl)-N-isobutylmorpholine-2-carboxamide;
4-(4-cyano-3-fluorobenzyl)-N-(2,3-dihydro-1,4-benzodioxin-6-ylmethyl)-N-isobutylmorpholine-2-carboxamide;
4-(2,1,3-benzoxadiazol-5-ylmethyl)-N-(2,3-dihydro-1,4-benzodioxin-6-ylmethyl)-N-isobutylmorpholine-2-carboxamide;
N-(2,3-dihydro-1,4-benzodioxin-6-ylmethyl)-N-isobutyl-4-[(1-isopropyl-1H-pyrazol-4-yl)methyl]morpholine-2-carboxamide;
N-(2,3-dihydro-1,4-benzodioxin-6-ylmethyl)-N-isobutyl-4-(isoxazol-3-ylmethyl)morpholine-2-carboxamide;
4-[3-(cyclopentyloxy)benzyl]-N-(2,3-dihydro-1,4-benzodioxin-6-ylmethyl)-N-isobutylmorpholine-2-carboxamide;
4-[2-(cyclopentyloxy)benzyl]-N-(2,3-dihydro-1,4-benzodioxin-6-ylmethyl)-N-isobutylmorpholine-2-carboxamide;

4-(2,1,3-benzoxadiazol-4-ylmethyl)-N-(2,3-dihydro-1,4-benzodioxin-6-ylmethyl)-N-isobutylmorpholine-2-carboxamide;

N-(2,3-dihydro-1,4-benzodioxin-6-ylmethyl)-4-[(6-fluoro-1H-benzimidazol-2-yl)methyl]-N-isobutylmorpholine-2-carboxamide;

N-(2,3-dihydro-1,4-benzodioxin-6-ylmethyl)-N-isobutyl-4-[4-(2-oxopyrrolidin-1-yl)benzyl]morpholine-2-carboxamide;

N-(2,3-dihydro-1,4-benzodioxin-6-ylmethyl)-N-isobutyl-4-(pyrazolo[1,5-a]pyridin-3-ylmethyl)morpholine-2-carboxamide;

N-(2,3-dihydro-1,4-benzodioxin-6-ylmethyl)-4-{[1-(4-fluorophenyl)-1H-pyrazol-4-yl]methyl}-N-isobutyl-morpholine-2-carboxamide;

N-(2,3-dihydro-1,4-benzodioxin-6-ylmethyl)-N-isobutyl-4-(pyrazolo[1,5-a]pyridin-2-ylmethyl)morpholine-2-carboxamide;

N-(3,4-dihydro-2H-1,5-benzodioxepin-7-ylmethyl)-N-isobutyl-4-(2-methoxybenzyl)morpholine-2-carboxamide;

N-(3,4-dihydro-2H-1,5-benzodioxepin-7-ylmethyl)-N-isobutyl-4-(3-methoxybenzyl)morpholine-2-carboxamide;

N-(3,4-dihydro-2H-1,5-benzodioxepin-7-ylmethyl)-N-isobutyl-4-[(1-methyl-1H-pyrazol-4-yl)methyl]morpholine-2-carboxamide;

4-[(2-chloro-6-methylpyridin-4-yl)methyl]-N-(3,4-dihydro-2H-1,5-benzodioxepin-7-ylmethyl)-N-isobutyl-morpholine-2-carboxamide;

N-(3,4-dihydro-2H-1,5-benzodioxepin-7-ylmethyl)-N-isobutyl-4-(pyrazolo[1,5-a]pyridin-3-ylmethyl)morpholine-2-carboxamide;

N-(2,3-dihydro-1,4-benzodioxin-6-ylmethyl)-N-isobutyl-4-[(2-methoxypyridin-3-yl)methyl]morpholine-2-carboxamide;

N-(2,3-dihydro-1,4-benzodioxin-6-ylmethyl)-4-[(3-fluoropyridin-4-yl)methyl]-N-isobutylmorpholine-2-carboxamide;

N-(2,3-dihydro-1,4-benzodioxin-6-ylmethyl)-4-(2-fluoro-5-methoxybenzyl)-N-isobutylmorpholine-2-carboxamide;

N-(2,3-dihydro-1,4-benzodioxin-6-ylmethyl)-4-(5-fluoro-2-methoxybenzyl)-N-isobutylmorpholine-2-carboxamide;

N-(2,3-dihydro-1,4-benzodioxin-6-ylmethyl)-4-[(5,7-dimethylpyrazolo[1,5-a]pyrimidin-3-yl)methyl]-N-isobutylmorpholine-2-carboxamide;

N-(3,4-dihydro-2H-1,5-benzodioxepin-7-ylmethyl)-N-isobutyl-4-[(4-methoxypyridin-3-yl)methyl]morpholine-2-carboxamide;

N-(3,4-dihydro-2H-1,5-benzodioxepin-7-ylmethyl)-4-[(5-fluoro-2-methoxypyridin-3-yl)methyl]-N-isobutyl-morpholine-2-carboxamide;

N-(3,4-dihydro-2H-1,5-benzodioxepin-7-ylmethyl)-4-[(3-fluoropyridin-4-yl)methyl]-N-isobutylmorpholine-2-carboxamide;

N-(3,4-dihydro-2H-1,5-benzodioxepin-7-ylmethyl)-4-(2-fluoro-5-methoxybenzyl)-N-isobutylmorpholine-2-carboxamide;

N-(3,4-dihydro-2H-1,5-benzodioxepin-7-ylmethyl)-4-(5-fluoro-2-methoxybenzyl)-N-isobutylmorpholine-2-carboxamide;

N-(3,4-dihydro-2H-1,5-benzodioxepin-7-ylmethyl)-4-[(5,7-dimethylpyrazolo[1,5-a]pyrimidin-3-yl)methyl]-N-isobutylmorpholine-2-carboxamide;

(2R)—N-(3,4-dihydro-2H-1,5-benzodioxepin-7-ylmethyl)-N-isobutyl-4-[(3-methoxypyridin-4-yl)methyl]morpholine-2-carboxamide;

N-(3,4-dihydro-2H-1,5-benzodioxepin-7-ylmethyl)-4-(4-hydroxybutyl)-N-isobutylmorpholine-2-carboxamide;

4-benzyl-N-isobutyl-N-(2,3,4,5-tetrahydro-1,6-benzodioxocin-8-ylmethyl)morpholine-2-carboxamide;

(2R)-4-benzyl-N-isobutyl-N-(2,3,4,5-tetrahydro-1-benzoxepin-7-ylmethyl)morpholine-2-carboxamide;

(2S)—N-(3,4-dihydro-2H-1,5-benzodioxepin-7-ylmethyl)-N-isobutyl-4-[(4-methoxypyridin-3-yl)methyl]morpholine-2-carboxamide;

(2R)—N-(3,4-dihydro-2H-1,5-benzodioxepin-7-ylmethyl)-N-isobutyl-4-[(4-methoxypyridin-3-yl)methyl]morpholine-2-carboxamide;

(2R)—N-(3,4-dihydro-2H-1,5-benzodioxepin-7-ylmethyl)-N-isobutyl-4-[(3-methoxypyrazin-2-yl)methyl]morpholine-2-carboxamide;

(2R)—N-(3,4-dihydro-2H-1,5-benzodioxepin-7-ylmethyl)-N-isobutyl-4-[(2-methoxy-6-methylpyrimidin-4-yl)methyl]morpholine-2-carboxamide;

8-[(4-benzylmorpholin-2-yl)carbonyl]-3,4,7,8,9,10-hexahydro-2H-[1,4]dioxepino[2,3-g]isoquinoline 8-{[4-(2-methoxybenzyl)morpholin-2-yl]carbonyl}-3,4,7,8,9,10-hexahydro-2H-[1,4]dioxepino[2,3-g]isoquinoline (2R)—N-(2,3-dihydro-1,4-benzodioxin-6-ylmethyl)-N-isobutyl-4-(2-methoxybenzyl)morpholine-2-carboxamide;

(2R)—N-(3,4-dihydro-2H-1,5-benzodioxepin-7-ylmethyl)-N-isobutyl-4-(2-methoxybenzyl)morpholine-2-carboxamide;

(2R)-4-[(5-chloro-1,3-dimethyl-1H-pyrazol-4-yl)methyl]-N-(3,4-dihydro-2H-1,5-benzodioxepin-7-ylmethyl)-N-isobutylmorpholine-2-carboxamide;

(2S)-4-[(5-chloro-1,3-dimethyl-1H-pyrazol-4-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-4-[(1,3-dimethyl-1H-pyrazol-4-yl)methyl]-N-isobutyl-morpholine-2-carboxamide;

N-isobutyl-N-(2,3,4,5-tetrahydro-1,6-benzodioxocin-8-ylmethyl)morpholine-2-carboxamide;

N-isobutyl-4-(2-methoxybenzyl)-N-(2,3,4,5-tetrahydro-1,6-benzodioxocin-8-ylmethyl)morpholine-2-carboxamide;

4-[(5-chloro-1,3-dimethyl-1H-pyrazol-4-yl)methyl]-N-isobutyl-N-(2,3,4,5-tetrahydro-1,6-benzodioxocin-8-ylmethyl)morpholine-2-carboxamide;

4-benzyl-N-isobutyl-N-[(3,3,4,4-tetrafluoro-2,3,4,5-tetrahydro-1,6-benzodioxocin-8-yl)methyl]morpholine-2-carboxamide;

(2R)—N-(3,4-dihydro-2H-1,5-benzodioxepin-7-ylmethyl)-N-isobutyl-4-[(4-methoxypyrimidin-5-yl)methyl]morpholine-2-carboxamide;

(2R)—N-(3,4-dihydro-2H-1,5-benzodioxepin-7-ylmethyl)-N-isobutyl-4-[(5-methoxypyridin-3-yl)methyl]morpholine-2-carboxamide;

4-benzyl-N-[(3,3-difluoro-3,4-dihydro-2H-1,5-benzodioxepin-7-yl)methyl]-N-isobutylmorpholine-2-carboxamide;

N-isobutyl-4-(2-methoxybenzyl)-N-(2,3,4,5-tetrahydro-1-benzoxepin-8-ylmethyl)morpholine-2-carboxamide;

4-benzyl-N-isobutyl-N-(6,7,8,9-tetrahydro-5H-benzo[7]annulen-2-ylmethyl)morpholine-2-carboxamide;

N-(3,4-dihydro-2H-1,5-benzodioxepin-7-ylmethyl)-4-[(1,2-dimethyl-1H-indol-3-yl)methyl]-N-isobutylmorpholine-2-carboxamide;

N-(3,4-dihydro-2H-1,5-benzodioxepin-7-ylmethyl)-N-isobutyl-4-[(5-methoxy-1,3-dimethyl-1H-pyrazol-4-yl)methyl]morpholine-2-carboxamide;

4-[(5-chloro-1-methyl-1H-pyrazol-4-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-N-isobutyl-4-{2-[(trifluoromethyl)thio]benzyl}morpholine-2-carboxamide;

4-benzyl-N-isobutyl-N-(2,3,4,5-tetrahydro-1-benzoxepin-8-ylmethyl)morpholine-2-carboxamide;

4-benzyl-N-(3,4-dihydro-2H-chromen-7-ylmethyl)-N-isobutylmorpholine-2-carboxamide;

N-(3,4-dihydro-2H-chromen-7-ylmethyl)-N-isobutyl-4-(2-methoxybenzyl)morpholine-2-carboxamide;

N-(3,4-dihydro-2H-1,5-benzodioxepin-7-ylmethyl)-4-[(2,5-dimethyl-3-furyl)methyl]-N-isobutylmorpholine-2-carboxamide;

N-(2-methylpropyl)-4-(phenylmethyl)-N-[(3,4,5,6-tetrahydro-2H-1,7-benzodioxonin-9-yl)methyl]morpholine-2-carboxamide;

4-benzyl-N-(2,3,4,5,6,7-hexahydro-1,8-benzodioxecin-10-ylmethyl)-N-isobutylmorpholine-2-carboxamide;

4-benzyl-N-isobutyl-N-(spiro[1,5-benzodioxepine-3,3'-oxetan]-7-ylmethyl)morpholine-2-carboxamide;

N-(2,3,4,5,6,7-hexahydro-1,8-benzodioxecin-10-ylmethyl)-N-isobutyl-4-(2-methoxybenzyl)morpholine-2-carboxamide;

N-isobutyl-4-(2-methoxybenzyl)-N-(spiro[1,5-benzodioxepine-3,3'-oxetan]-7-ylmethyl)morpholine-2-carboxamide;

N-(3,4-dihydro-2H-1,5-benzodioxepin-7-ylmethyl)-N-isobutyl-4-[(1-methyl-1H-indol-3-yl)methyl]morpholine-2-carboxamide;

4-[(2-chloro-1-methyl-1H-indol-3-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-N-isobutyl-4-[(2-methylimidazo[1,2-a]pyridin-3-yl)methyl]morpholine-2-carboxamide;

4-benzyl-N-(6,11-dihydrodibenzo[b,f][1,4]dioxocin-2-ylmethyl)-N-isobutylmorpholine-2-carboxamide;

N-isobutyl-4-(2-methoxybenzyl)-N-(3,4,5,6-tetrahydro-2H-1,7-benzodioxonin-9-ylmethyl)morpholine-2-carboxamide;

N-(6,11-dihydrodibenzo[b,f][1,4]dioxocin-2-ylmethyl)-N-isobutyl-4-(2-methoxybenzyl)morpholine-2-carboxamide;

N-(3,4-dihydro-2H-1,5-benzodioxepin-7-ylmethyl)-N-isobutyl-4-(pyridin-3-ylmethyl)morpholine-2-carboxamide;

4-[(6-chloroimidazo[2,1-b][1,3]thiazol-5-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-N-isobutyl-4-(pyridin-4-ylmethyl)morpholine-2-carboxamide;

N-(3,4-dihydro-2H-1,5-benzodioxepin-7-ylmethyl)-4-(2,5-dimethoxybenzyl)-N-isobutylmorpholine-2-carboxamide;

4-(1,3-benzodioxol-4-ylmethyl)-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-4-(2,3-dihydro-1,4-benzodioxin-5-ylmethyl)-N-isobutylmorpholine-2-carboxamide;

4-(3,4-dihydro-2H-1,5-benzodioxepin-6-ylmethyl)-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-N-isobutyl-4-[(1,3,5-trimethyl-1H-pyrazol-4-yl)methyl]morpholine-2-carboxamide;

N-(3,4-dihydro-2H-1,5-benzodioxepin-7-ylmethyl)-N-isobutyl-4-[(6-methylpyridin-2-yl)methyl]morpholine-2-carboxamide;

N-(3,4-dihydro-2H-1,5-benzodioxepin-7-ylmethyl)-4-[(3,5-dimethylisoxazol-4-yl)methyl]-N-isobutylmorpholine-2-carboxamide;

N-(3,4-dihydro-2H-1,5-benzodioxepin-7-ylmethyl)-4-(2,3-dimethoxybenzyl)-N-isobutylmorpholine-2-carboxamide;

N-(3,4-dihydro-2H-1,5-benzodioxepin-7-ylmethyl)-4-(2,6-dimethoxybenzyl)-N-isobutylmorpholine-2-carboxamide;

N-(3,4-dihydro-2H-1,5-benzodioxepin-7-ylmethyl)-4-(2-fluoro-3-methoxybenzyl)-N-isobutylmorpholine-2-carboxamide;

4-[(2-chloropyridin-3-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-N-isobutyl-4-[(6-methoxypyridin-3-yl)methyl]morpholine-2-carboxamide;

N-(3,4-dihydro-2H-1,5-benzodioxepin-7-ylmethyl)-4-(2-ethoxybenzyl)-N-isobutylmorpholine-2-carboxamide;

4-[(6-chloropyridin-3-yl)methyl]-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-4-(4-fluoro-3-methoxybenzyl)-N-isobutylmorpholine-2-carboxamide;

N-(3,4-dihydro-2H-1,5-benzodioxepin-7-ylmethyl)-N-isobutyl-4-[(2-methoxypyridin-3-yl)methyl]morpholine-2-carboxamide;

N-(3,4-dihydro-2H-1,5-benzodioxepin-7-ylmethyl)-N-isobutyl-4-[2-(trifluoromethoxy)benzyl]morpholine-2-carboxamide;

N-(3,4-dihydro-2H-1,5-benzodioxepin-7-ylmethyl)-4-(3-ethoxybenzyl)-N-isobutylmorpholine-2-carboxamide;

N-(3,4-dihydro-2H-1,5-benzodioxepin-7-ylmethyl)-4-(2-fluoro-6-methoxybenzyl)-N-isobutylmorpholine-2-carboxamide;

N-(3,4-dihydro-2H-1,5-benzodioxepin-7-ylmethyl)-N-isobutyl-4-(1,6-naphthyridin-8-ylmethyl)morpholine-2-carboxamide;

4-benzyl-N-isobutyl-N-[(2,2,3,3-tetrafluoro-2,3-dihydro-1,4-benzodioxin-5-yl)methyl]morpholine-2-carboxamide;

(2R)—N-[(3-fluoro-3,4-dihydro-2H-1,5-benzodioxepin-7-yl)methyl]-N-isobutyl-4-(2-methoxybenzyl)morpholine-2-carboxamide;

(2R)—N-{[3-(benzyloxy)-3,4-dihydro-2H-1,5-benzodioxepin-7-yl]methyl}-N-isobutyl-4-(2-methoxybenzyl)morpholine-2-carboxamide;

(2R)—N-{[(3R)-3-hydroxy-3,4-dihydro-2H-1,5-benzodioxepin-7-yl]methyl}-N-isobutyl-4-(2-methoxybenzyl)morpholine-2-carboxamide;

(2R)—N-{[(3S)-3-hydroxy-3,4-dihydro-2H-1,5-benzodioxepin-7-yl]methyl}-N-isobutyl-4-(2-methoxybenzyl)morpholine-2-carboxamide;

4-[(5-chloro-1,3-dimethyl-1H-pyrazol-4-yl)methyl]-N-isobutyl-N-(2,3,4,5-tetrahydro-1-benzoxepin-7-ylmethyl)morpholine-2-carboxamide;

N-isobutyl-4-(2-methoxybenzyl)-N-(2,3,4,5-tetrahydro-1-benzoxepin-7-ylmethyl)morpholine-2-carboxamide;

4-benzyl-N-(3,4-dihydro-2H-1,5-benzodioxepin-6-ylmethyl)-N-isobutylmorpholine-2-carboxamide;

4-benzyl-N-isobutyl-N-[(3-methyl-3,4-dihydro-2H-1,5-benzodioxepin-7-yl)methyl]morpholine-2-carboxamide;

4-benzyl-N-[(9-hydroxy-6,7,8,9-tetrahydro-5H-benzo[7]annulen-2-yl)methyl]-N-isobutylmorpholine-2-carboxamide;

4-benzyl-N-isobutyl-N-[(9-methoxy-6,7,8,9-tetrahydro-5H-benzo[7]annulen-2-yl)methyl]morpholine-2-carboxamide;

N-[(9-hydroxy-6,7,8,9-tetrahydro-5H-benzo[7]annulen-2-yl)methyl]-N-isobutyl-4-(2-methoxybenzyl)morpholine-2-carboxamide;

N-isobutyl-4-(2-methoxybenzyl)-N-[(9-methoxy-6,7,8,9-tetrahydro-5H-benzo[7]annulen-2-yl)methyl]morpholine-2-carboxamide;

N-(3,4-dihydro-2H-1,5-benzodioxepin-7-ylmethyl)-N-isobutyl-4-(3-methoxy-4-methylbenzyl)morpholine-2-carboxamide;

N-(3,4-dihydro-2H-1,5-benzodioxepin-7-ylmethyl)-4-(4-fluoro-2-methoxybenzyl)-N-isobutylmorpholine-2-carboxamide;

N-(3,4-dihydro-2H-1,5-benzodioxepin-7-ylmethyl)-N-isobutyl-4-(5-isopropyl-2-methoxybenzyl)morpholine-2-carboxamide;

N-(3,4-dihydro-2H-1,5-benzodioxepin-7-ylmethyl)-4-(2,3-dihydro-1-benzofuran-7-ylmethyl)-N-isobutylmorpholine-2-carboxamide;

4-(4-chloro-2-fluoro-5-methoxybenzyl)-N-(3,4-dihydro-2H-1,5-benzodioxepin-7-ylmethyl)-N-isobutylmorpholine-2-carboxamide;

N-(3,4-dihydro-2H-1,5-benzodioxepin-7-ylmethyl)-4-[(2-hydroxypyridin-4-yl)methyl]-N-isobutylmorpholine-2-carboxamide;

N-(3,4-dihydro-2H-1,5-benzodioxepin-7-ylmethyl)-N-isobutyl-4-[3-(trifluoromethoxy)benzyl]morpholine-2-carboxamide;

N-(3,4-dihydro-2H-1,5-benzodioxepin-7-ylmethyl)-N-isobutyl-4-[(2-methylimidazo[1,2-a]pyrimidin-3-yl)methyl]morpholine-2-carboxamide;

N-(3,4-dihydro-2H-1,5-benzodioxepin-7-ylmethyl)-N-isobutyl-4-(pyridazin-4-ylmethyl)morpholine-2-carboxamide;

N-(3,4-dihydro-2H-1,5-benzodioxepin-7-ylmethyl)-N-isobutyl-4-[(3-methylpyridazin-4-yl)methyl]morpholine-2-carboxamide;

4-benzyl-N-(3,4-dihydro-2H-1,5-benzodioxepin-7-ylmethyl)-N-isobutyl-2-methylmorpholine-2-carboxamide;

4-benzyl-N-(2,3-dihydro-1H-inden-5-ylmethyl)-N-isobutylmorpholine-2-carboxamide;

(2R)—N-(3,4-dihydro-2H-chromen-7-ylmethyl)-N-isobutyl-4-(2-methoxybenzyl)morpholine-2-carboxamide;

N-isobutyl-4-(2-methoxybenzyl)-N-(6,7,8,9-tetrahydro-5H-benzo[7]annulen-2-ylmethyl)morpholine-2-carboxamide;

N-(3,4-dihydro-2H-1,5-benzodioxepin-7-ylmethyl)-4-(2-hydroxybenzyl)-N-isobutylmorpholine-2-carboxamide;

N-(3,4-dihydro-2H-1,5-benzodioxepin-7-ylmethyl)-4-(3-fluoro-2-methoxybenzyl)-N-isobutylmorpholine-2-carboxamide;

(2R)—N-(2,3-dihydro-1,4-benzodioxin-6-ylmethyl)-4-(2,3-dihydro-1-benzofuran-7-ylmethyl)-N-isobutylmorpholine-2-carboxamide;

(2R)—N-(2,3-dihydro-1,4-benzodioxin-6-ylmethyl)-4-(4-fluoro-2-methoxybenzyl)-N-isobutylmorpholine-2-carboxamide;

N-(3,4-dihydro-2H-chromen-6-ylmethyl)-N-isobutyl-4-(2-methoxybenzyl)morpholine-2-carboxamide;

(2R)—N-[3-(hydroxymethyl)-2,3-dihydro-1,4-benzodioxin-6-yl]methyl-N-isobutyl-4-(2-methoxybenzyl)morpholine-2-carboxamide;

(−)-(2R)—N-(3,4-dihydro-2H-1,5-benzodioxepin-7-ylmethyl)-4-(4-fluoro-3-methoxybenzyl)-N-isobutylmorpholine-2-carboxamide;

(−)-(2R)-(3,4-dihydro-2H-1,5-benzodioxepin-7-ylmethyl)-4-(2-fluoro-5-methoxybenzyl)-N-isobutylmorpholine-2-carboxamide;

(−)-(2R)-4-(2-fluoro-5-methoxybenzyl)-N-isobutyl-N-(2,3,4,5-tetrahydro-1-benzoxepin-8-ylmethyl)morpholine-2-carboxamide;

(−)-(2R)-4-[(2-chloro-6-methylpyridin-4-yl)methyl]-N-(3,4-dihydro-2H-1,5-benzodioxepin-7-ylmethyl)-N-isobutylmorpholine-2-carboxamide;

(−)-(2R)—N-(3,4-dihydro-2H-1,5-benzodioxepin-7-ylmethyl)-N-isobutyl-4-(quinolin-8-ylmethyl)morpholine-2-carboxamide;

(−)-(2R)—N-(3,4-dihydro-2H-1,5-benzodioxepin-7-ylmethyl)-4-(3-fluoro-2-hydroxybenzyl)-N-isobutylmorpholine-2-carboxamide;

(−)-(2R)—N-(3,4-dihydro-2H-1,5-benzodioxepin-7-ylmethyl)-4-(3-hydroxybenzyl)-N-isobutylmorpholine-2-carboxamide;

(−)-(2R)—N-(3,4-dihydro-2H-1,5-benzodioxepin-7-ylmethyl)-4-(2-hydroxy-5-methoxybenzyl)-N-isobutylmorpholine-2-carboxamide;

(−)-(2R)—N-(3,4-dihydro-2H-1,5-benzodioxepin-7-ylmethyl)-4-{[3-hydroxy-5-(hydroxymethyl)-2-methylpyridin-4-yl]methyl}-N-isobutylmorpholine-2-carboxamide;

(2R)—N-isobutyl-4-(3-methoxy-4-methylbenzyl)-N-(quinolin-6-ylmethyl)morpholine-2-carboxamide;

(2R)—N-isobutyl-4-(2-methoxy-4-methylbenzyl)-N-(quinolin-6-ylmethyl)morpholine-2-carboxamide;

(2R)-4-(2,3-dihydro-1-benzofuran-7-ylmethyl)-N-isobutyl-N-(quinolin-6-ylmethyl)morpholine-2-carboxamide;

(2R)-4-(2-hydroxybenzyl)-N-isobutyl-N-(quinolin-6-ylmethyl)morpholine-2-carboxamide;

(2R)-4-(4-chloro-2-fluoro-5-methoxybenzyl)-N-isobutyl-N-(quinolin-6-ylmethyl)morpholine-2-carboxamide;

(2R)-4-(4-fluoro-2-methoxybenzyl)-N-isobutyl-N-(quinolin-6-ylmethyl)morpholine-2-carboxamide;

(2R)-4-(2-fluoro-6-methoxybenzyl)-N-isobutyl-N-(quinolin-6-ylmethyl)morpholine-2-carboxamide;

(2R)-4-(3-ethoxybenzyl)-N-isobutyl-N-(quinolin-6-ylmethyl)morpholine-2-carboxamide;

(2R)-4-(4-fluoro-3-methoxybenzyl)-N-isobutyl-N-(quinolin-6-ylmethyl)morpholine-2-carboxamide;

(2R)-4-(2-ethoxybenzyl)-N-isobutyl-N-(quinolin-6-ylmethyl)morpholine-2-carboxamide;

(2R)-4-[(2-chloropyridin-3-yl)methyl]-N-isobutyl-N-(quinolin-6-ylmethyl)morpholine-2-carboxamide;

(2R)-4-(2-fluoro-3-methoxybenzyl)-N-isobutyl-N-(quinolin-6-ylmethyl)morpholine-2-carboxamide;

(2R)-4-(2,6-dimethoxybenzyl)-N-isobutyl-N-(quinolin-6-ylmethyl)morpholine-2-carboxamide;

(2R)-4-(2,3-dimethoxybenzyl)-N-isobutyl-N-(quinolin-6-ylmethyl)morpholine-2-carboxamide;

(2R)-4-[(3,5-dimethylisoxazol-4-yl)methyl]-N-isobutyl-N-(quinolin-6-ylmethyl)morpholine-2-carboxamide;

(2R)—N-isobutyl-4-[(6-methylpyridin-2-yl)methyl]-N-(quinolin-6-ylmethyl)morpholine-2-carboxamide;

(2R)—N-isobutyl-N-(quinolin-6-ylmethyl)-4-[(1,3,5-trimethyl-1H-pyrazol-4-yl)methyl]morpholine-2-carboxamide;

(2R)-4-(3,4-dihydro-2H-1,5-benzodioxepin-6-ylmethyl)-N-isobutyl-N-(quinolin-6-ylmethyl)morpholine-2-carboxamide;

(2R)-4-(2,3-dihydro-1,4-benzodioxin-5-ylmethyl)-N-isobutyl-N-(quinolin-6-ylmethyl)morpholine-2-carboxamide;

(2R)-4-(1,3-benzodioxol-4-ylmethyl)-N-isobutyl-N-(quinolin-6-ylmethyl)morpholine-2-carboxamide;

(2R)-4-(2,5-dimethoxybenzyl)-N-isobutyl-N-(quinolin-6-ylmethyl)morpholine-2-carboxamide;

(2R)-4-[(6-chloroimidazo[2,1-b][1,3]thiazol-5-yl)methyl]-N-isobutyl-N-(quinolin-6-ylmethyl)morpholine-2-carboxamide;

(2R)-4-[(2-chloro-1-methyl-1H-indol-3-yl)methyl]-N-isobutyl-N-(quinolin-6-ylmethyl)morpholine-2-carboxamide;

(2R)—N-isobutyl-4-[(1-methyl-1H-pyrazol-4-yl)methyl]-N-(quinolin-6-ylmethyl)morpholine-2-carboxamide;

(2R)-4-(4-chlorobenzyl)-N-isobutyl-N-(quinolin-6-ylmethyl)morpholine-2-carboxamide (2R)-4-[(2-chloro-6-methylpyridin-4-yl)methyl]-N-isobutyl-N-(quinolin-6-ylmethyl)morpholine-2-carboxamide;

(2R)-4-[(1,3-dimethyl-1H-pyrazol-4-yl)methyl]-N-isobutyl-N-(quinolin-6-ylmethyl)morpholine-2-carboxamide;

(2R)-4-(3-chlorobenzyl)-N-isobutyl-N-(quinolin-6-ylmethyl)morpholine-2-carboxamide;

(2R)-4-(2,4-difluorobenzyl)-N-isobutyl-N-(quinolin-6-ylmethyl)morpholine-2-carboxamide;

(2R)-4-(2-fluorobenzyl)-N-isobutyl-N-(quinolin-6-ylmethyl)morpholine-2-carboxamide;

(2R)-4-[(5-fluoro-2-methoxypyridin-3-yl)methyl]-N-isobutyl-N-(quinolin-6-ylmethyl)morpholine-2-carboxamide;

(2R)-4-(5-fluoro-2-methoxybenzyl)-N-isobutyl-N-(quinolin-6-ylmethyl)morpholine-2-carboxamide;

(2R)-4-(2-fluoro-5-methoxybenzyl)-N-isobutyl-N-(quinolin-6-ylmethyl)morpholine-2-carboxamide;

(2R)—N-isobutyl-4-[(2-methoxypyridin-3-yl)methyl]-N-(quinolin-6-ylmethyl)morpholine-2-carboxamide;

(2R)-4-[(4-bromo-2-thienyl)methyl]-N-isobutyl-N-(quinolin-6-ylmethyl)morpholine-2-carboxamide;

(2R)-4-[(1,5-dimethyl-1H-pyrazol-4-yl)methyl]-N-isobutyl-N-(quinolin-6-ylmethyl)morpholine-2-carboxamide;

(2R)—N-isobutyl-4-(3-methoxybenzyl)-N-(quinolin-6-ylmethyl)morpholine-2-carboxamide;

(2R)-4-(3,4-dimethylbenzyl)-N-isobutyl-N-(quinolin-6-ylmethyl)morpholine-2-carboxamide;

(2R)—N-isobutyl-N-(quinolin-6-ylmethyl)-4-[(1,3,5-trimethyl-1H-pyrazol-4-yl)methyl]morpholine-2-carboxamide;

(2R)—N-isobutyl-4-[(5-methyl-2-thienyl)methyl]-N-(quinolin-6-ylmethyl)morpholine-2-carboxamide;

(2R)—N-isobutyl-4-(2-methylbenzyl)-N-(quinolin-6-ylmethyl)morpholine-2-carboxamide;

(2R)—N-isobutyl-4-(pyrazolo[1,5-a]pyridin-7-ylmethyl)-N-(quinolin-6-ylmethyl)morpholine-2-carboxamide;

(2R)-4-benzyl-N-isobutyl-N-(quinolin-6-ylmethyl)morpholine-2-carboxamide;

or a pharmaceutically acceptable salt thereof.

18. A pharmaceutical composition which comprises an inert carrier and a compound of claim 1 or a pharmaceutically acceptable salt thereof.

19. A method for treating a syndrome or disorder selected from: non-24-hour sleep-wake syndrome; rapid time-zone change syndrome; work-shift syndrome; delayed phase sleep syndrome; advanced sleep phase syndrome; irregular sleep-wake pattern syndrome; syndrome associated with decreased amplitude; seasonal affective disorder; and a condition due to a drug which cause reductions in REM sleep as a side effect, in a mammalian patient in need thereof which comprises administering to the patient a therapeutically effective amount of the compound of claim 1 or a pharmaceutically acceptable salt thereof.

\* \* \* \* \*